United States Patent
Rimestad et al.

(10) Patent No.: US 11,942,220 B2
(45) Date of Patent: Mar. 26, 2024

(54) METHODS AND APPARATUS FOR ASSESSING EMBRYO DEVELOPMENT

(71) Applicant: VITROLIFE A/S, Viby (DK)

(72) Inventors: Jens Rimestad, Skødstrup (DK); Jørgen Berntsen, Viborg (DK); Michael Sass Hansen, København S (DK); Sebastian Gerrit Jan Brandes Kraaijenzank, København Ø (DK)

(73) Assignee: VITROLIFE A/S, Viby (DK)

( * ) Notice: Subject to any disclaimer, the term of this patent is extended or adjusted under 35 U.S.C. 154(b) by 688 days.

(21) Appl. No.: 17/251,143

(22) PCT Filed: May 29, 2019

(86) PCT No.: PCT/EP2019/064052
§ 371 (c)(1),
(2) Date: Dec. 10, 2020

(87) PCT Pub. No.: WO2020/001914
PCT Pub. Date: Jan. 2, 2020

(65) Prior Publication Data
US 2021/0249135 A1    Aug. 12, 2021

(30) Foreign Application Priority Data
Jun. 28, 2018  (GB) .................................... 1810634

(51) Int. Cl.
*G16H 50/20* (2018.01)
*G06T 7/194* (2017.01)
*G06T 7/33* (2017.01)

(52) U.S. Cl.
CPC .......... *G16H 50/20* (2018.01); *G06T 3/4046* (2013.01); *G06T 7/194* (2017.01); *G06T 7/33* (2017.01);
(Continued)

(58) Field of Classification Search
CPC ....... G16H 50/20; G06T 3/4046; G06T 7/194; G06T 7/33; G06T 2207/20081;
(Continued)

(56) References Cited

U.S. PATENT DOCUMENTS

2014/0247972 A1  9/2014 Wang et al.
2015/0268227 A1  9/2015 Tan et al.

FOREIGN PATENT DOCUMENTS

CN        105408746    *  3/2016  ............. G01N 33/50
WO        2007/144001 A2   12/2007
(Continued)

OTHER PUBLICATIONS

International Search Report dated Sep. 12, 2019 in corresponding International Application No. PCT/EP2019/064052.
(Continued)

*Primary Examiner* — Jerome Grant, II
(74) *Attorney, Agent, or Firm* — Honigman LLP

(57) ABSTRACT

A method of processing a series of images of an embryo to determine estimated timings of developmental events for the embryo, wherein the method comprises: determining feature information for each image, the feature information for each image representing the content of the image; establishing machine learned classifiers for associating each image with a respective likelihood of the image being associated with one or more developmental events based on the feature information for the image; applying the machine learned classifiers to the feature information for each image to determine a respective likelihood of the image being associated with one or more developmental events, and determining estimated timings for the plurality of developmental events for the embryo from the respective likelihoods of the respective images being associated with respective ones of the plurality of developmental events. The method may further comprise determining an indication of a confidence estimate for the timings.

21 Claims, 21 Drawing Sheets

(52) U.S. Cl.
CPC ............... *G06T 2207/20081* (2013.01); *G06T 2207/20084* (2013.01); *G06T 2207/20132* (2013.01); *G06T 2207/30044* (2013.01)

(58) Field of Classification Search
CPC . G06T 2207/20084; G06T 2207/20132; G06T 2207/30044; G06V 20/69
USPC ........................................................ 382/128
See application file for complete search history.

(56) References Cited

FOREIGN PATENT DOCUMENTS

| WO | WO2020012616 | * | 7/2018 | ........... G06T 7/0012 |
| WO | WO2020157761 | * | 8/2020 | ............... G06T 7/00 |

OTHER PUBLICATIONS

Written Opinion of the International Searching Authority dated Sep. 12, 2019 in corresponding International Application No. PCT/EP2019/064052.

Aisha Sajjad Khan: "Automated monitoring of early stage human embryonic cells in time-lapse microscopy images", Sep. 1, 2016 (Sep. 1, 2016), XP055618995.

* cited by examiner

METHODS AND APPARATUS FOR ASSESSING EMBRYO DEVELOPMENT

PRIORITY CLAIM

This application is a National Phase application filed under 35 USC § 371 of International Application No. PCT/EP2019/064052, filed on May 29, 2019, which claims priority to United Kingdom Patent Application No. 1810634.4, filed Jun. 28, 2018, each of which is incorporated by reference in its entirety.

BACKGROUND OF THE INVENTION

The present disclosure relates to methods and apparatus for assessing embryo development. In particular, some embodiments relate to methods and apparatus for establishing values for a plurality of parameters (variables/indicators) relating to the development of an embryo, for example, timings for certain cell division events.

Infertility affects more than 80 million people worldwide. It is estimated that 10% of all couples experience primary or secondary infertility. In vitro fertilization (IVF) is an elective medical treatment that may provide a couple who has been otherwise unable to conceive a chance to establish a pregnancy. It is a process in which eggs (oocytes) are taken from a woman's ovaries and then fertilized with sperm in the laboratory. It will be appreciated that donor oocytes and/or donor sperm may be used. The embryos created in this process are then placed into the uterus for potential implantation. In between fertilization (insemination) and transfer the embryos are typically stored in an incubation chamber of an incubator for 2-6 days during which time they may be regularly monitored, for example through imaging, to assess their development. Conditions within the incubator, such as temperature and atmospheric composition, are controlled, generally with a view to emulating the conditions in the oviduct and uterus.

In a typical IVF cycle a number of eggs from a single patient will be fertilized and the resulting embryos incubated. However, it is usual for not all incubated embryos to be transferred to the patient's uterus. This is to reduce the risk of potentially dangerous multiple births. Embryos will typically be selected for transfer on the basis of an assessment of the development potential of the embryos that have been incubated. Embryos determined to have the greatest potential for developing into a live birth will be preferentially selected over other embryos in their cohort. Accordingly, an important aspect of IVF treatment is assessing development potential of the embryos comprising a cohort, i.e. determining embryo quality where embryo quality is indicative of a prediction representing the likelihood of an embryo successfully implanting, developing in the uterus after transfer and leading to the birth of a healthy baby.

A powerful tool for assessing embryo quality is time-lapse embryo imaging. Time-lapse embryo imaging involves obtaining images of embryos during their development. This can allow the timings of various developmental events, such as cell divisions, to be established. These timings may sometimes be referred to as morphokinetic parameters for the embryo. Studies have shown how the timings and durations of various embryonic development events can be correlated with development potential for an embryo. For example, a relatively early time of division from one cell to two cells has been found to be an indicator of a good quality embryo. Other morphokinetic parameters, for example the degree of synchronicity in the two divisions when dividing from two cells to four cells, are also found to be sensitive to embryo quality. More generally, there have been proposed various approaches for assessing the development potential of an embryo from parameters relating to the embryo's in-vitro development. Consequently it can be important when assessing embryo quality using time-lapse imaging to establish values for various parameters relating to the timings of various embryo development events and/or other characteristics relating to the development of the embryo, for example in terms of cell-uniformity (evenness) at different stages, the appearance of pro-nuclei (PN), and the presence of multi-nucleation (MN). To establish values for parameters relating to embryo development from a series of time-lapse images a user will typically view the series of time-lapse images as a movie to identify the images (and hence timings) associated with events of interest and to identify images in which other characteristics (such as unevenness, PN appearance, and MN) can be assessed. This process of establishing values for parameters of interest from a time-lapse series of images is sometimes called annotation Annotation is generally performed manually by skilled embryologists and can take a relatively long time to perform. This is because in addition to making the relevant clinical assessments for the respective parameters of interest, the user needs to navigate through what can be a relatively long series of images, and furthermore will typically do this for a number of different embryos for each patient. To help address this, there have been proposals for automated annotation techniques, for example in US20140247972A1 [1].

Accordingly there is a desire for new schemes which can establish values for morphokinetic parameters relating to the development of an embryo from a series of images.

SUMMARY OF THE INVENTION

According to a first aspect of certain embodiments there is provided a computer-implemented method of processing a time series of images of an embryo to determine estimated timings for a plurality of developmental events for the embryo, wherein the method comprises: determining feature information for each of the images, the feature information for each image representing the content of the image; establishing machine learned classifiers for associating each of the images with a respective likelihood of the image being associated with one or more of the plurality of developmental events based on the feature information for the image; applying the machine learned classifiers to the feature information for each of the images to determine a respective likelihood of the image being associated with one or more of the plurality of developmental events; and determining estimated timings for the plurality of developmental events for the embryo from the respective likelihoods of the respective images being associated with respective ones of the plurality of developmental events.

In some examples the feature information for each image comprises information abstracted from the content of the image. For example, the feature information for each image may comprise a representation of a frequency distribution of signal values for pixels comprising the image.

In some examples the feature information for each image is abstracted using one or more approaches selected from the group comprising: (i) a scale invariant feature transform approach; (ii) a machine learned feature clustering approach; (iii) a machine learned neural network approach.

In some examples the feature information for each image is the image itself.

In some examples the step of determining feature information for each of the images includes cropping the images.

In some examples the step of determining feature information for each of the images includes rescaling the images.

Some examples further comprise segmenting the images to classify pixels in the images as corresponding to the embryo or background, and wherein the feature information for each of the images is determined by preferentially using the pixels classified as corresponding to the embryo over the pixels classified as corresponding to the background.

In some examples the plurality of developmental events for the embryo comprise one or more developmental events selected from the group comprising: (i) any cleavage event; (ii) cleavage to a 2-blastomere embryo; (iii) cleavage to a 3-blastomere embryo; (iv) cleavage to a 4-blastomere embryo; (v) cleavage to a 5-blastomere embryo; (vi) cleavage to a 6-blastomere embryo; (vii) cleavage to a 7-blastomere embryo; (viii) cleavage to an 8-blastomere embryo; (ix) cleavage to an 9 or more blastomere embryo; (x) fading of pronuclei; (xi) start of compaction; (xii) formation of morula; (xiii) initial differentiation of trophectoderm; (xiv) start of blastulation; (xv) formation of a blastocyst; (xvi) initial differentiation of inner cell mass; (xvii) onset of expansion of a blastocyst; (xviii) hatching of a blastocyst; (xix) appearance of first polar body; NO appearance of second polar body; (xxi) appearance of first pronuclei; (xxii) appearance of second pronuclei; (xxiii) time of pronuclei alignment; (xiv) start of blastocyst collapse; and (xv) start of blastocyst re-expansion.

In some examples the step of determining estimated timings for the plurality of developmental events for the embryo is performed using a dynamic programming approach.

In some examples the dynamic programming approach comprises a Viterbi algorithm.

In some examples the step of determining estimated timings for the plurality of developmental events for the embryo further comprises determining a confidence estimate for respective ones of the estimated timings. In some cases the confidence estimate for respective ones of the estimated timings may be determined based on one or more of the estimated timings; feature information; an estimated development event likelihood.

In some examples the time series of images of the embryo comprise a subset of images of the embryo selected from a larger number of images of the embryo.

In some examples each image of the embryo comprises a plurality of frames representing the embryo at substantially the same stage of its development.

In some examples the plurality of frames correspond to representations of the embryo in different focal planes and/or different colours.

Some examples further comprise providing output signalling representing the estimated timings.

Some examples further comprise determining a development potential for the embryo using the estimated timings.

According to a further aspect of certain embodiments there is provided a non-transitory computer program product bearing machine readable instructions for carrying out the method of the first aspect of the invention.

According to a further aspect of certain embodiments there is provided a computer apparatus for processing a time series of images of an embryo to determine estimated timings for a plurality of developmental events for the embryo, wherein the computer apparatus comprises a processor element configured to: determine feature information for each of the images, the feature information for each image representing the content of the image; establish machine learned classifiers for associating each of the images with a respective likelihood of the image being associated with one or more of the plurality of developmental events based on the feature information for the image; apply the machine learned classifiers to the feature information for each of the images to determine a respective likelihood of the image being associated with one or more of the plurality of developmental events; and determine estimated timings for the plurality of developmental events for the embryo from the respective likelihoods of the respective images being associated with respective ones of the plurality of developmental events.

BRIEF DESCRIPTION OF THE DRAWINGS

The disclosure is now described by way of example only with reference to the following drawings in which.

DETAILED DESCRIPTION

Figure 1:
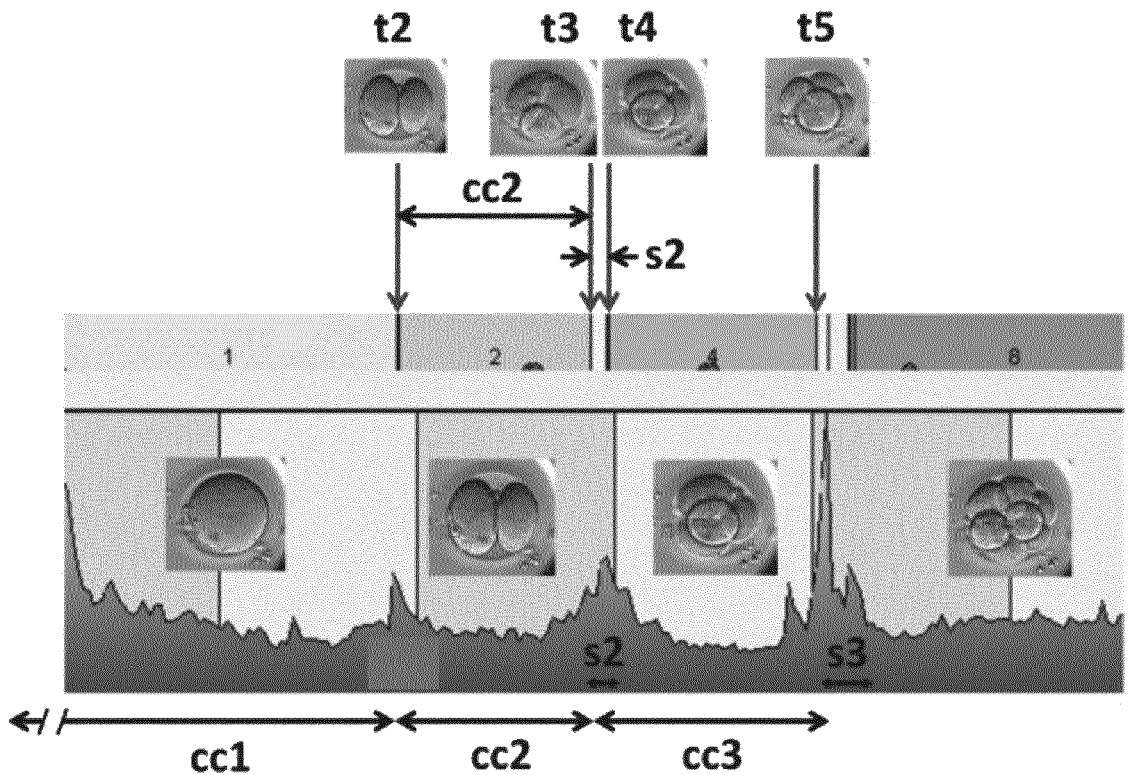
FIG. 1 schematically represents some terminology as used herein for an embryo cleavage pattern showing cleavage times (t2 to t5), duration of cell cycles (cc1 to cc3), and synchronies (s2 and s3) in relation to example images of an embryo.

Unless the context demands otherwise, the terms used herein should be interpreted in accordance with their meanings as commonly understood by one of ordinary skill in the art to which this disclosure belongs. Some terms may be used herein in accordance with the following definitions (unless the context demands another meaning).

Cleavage time (cell division time/transition time) is defined as the first observed timepoint relative to a defined start point (zero time) when newly formed blastomeres are completely separated by confluent cell membranes, the cleavage time is therefore the time of completion of a blastomere cleavage. In the present context the times are usually expressed as hours post the time of insemination (e.g. the time of Intra-Cytoplasmic Sperm Injection (ICSI), also called microinjection). However, it could also be post the time of mixing of sperm and oocyte (in traditional IVF) or post the time where the successful fusion of gametes to form a new organism (the zygote) is observed for the first time, i.e. exclusion of the second polar body. Similarly, it could be post the time for pronuclear appearance or fading/disappearance or other significant developmental parameter. Cleavage times may thus be defined as follows:

$t_2$: Time of cleavage to 2 blastomere embryo
$t_3$: Time of cleavage to 3 blastomere embryo
$t_4$: Time of cleavage to 4 blastomere embryo
$t_5$: Time of cleavage to 5 blastomere embryo
$t_6$: Time of cleavage to 6 blastomere embryo
$t_7$: Time of cleavage to 7 blastomere embryo
$t_8$: Time of cleavage to 8 blastomere embryo
$t_9$: Time of cleavage to 9 blastomere embryo
$t_n$: Time of cleavage to n blastomere embryo The first cell cycle duration $cc1$ is the period between fertilization and the cleavage time $t_2$ that provides the first pair of daughter cells (i.e. the first second-generation cells). The second cell cycle duration $cc2$ is the period between the cleavage time $t_2$ that provides the first pair of daughter cells and the cleavage time $t_3$ that provides the first pair of granddaughter cells (i.e. the first third-generation cells). The third cell cycle duration $cc3$ is the period between the cleavage time $t_3$ that provides the first pair of granddaughter cells and the cleavage time $t_5$ that provides the first pair of great-granddaughter cells (i.e. the first fourth-generation cells). The fourth cell cycle duration $cc4$ is the period between the cleavage time $t_5$ that provides the first pair of great-granddaughter cells and the cleavage time $t_9$ that provides the first pair of great-great-granddaughter cells (i.e. the first fifth-generation cells).

These cell cycle durations are thus based on the fastest of the blastomeres to divide for each new generation. However, there are additional cell cycle durations associated with division of slower blastomeres.

For example, in addition to cell cycle duration $cc2$ there is a cell cycle duration $cc2b$ corresponding to the period between the cleavage time $t_2$ that provides the first pair of daughter cells and the cleavage time $t_4$ that provides the second pair of granddaughter cells. In this regard cell cycle duration $cc2$ may also be referred to as cell cycle duration $cc2a$ for simplicity in terminology.

Furthermore, in addition to cell cycle duration $cc3$ there is a cell cycle duration $cc3b$ corresponding to the period between the cleavage time $t_3$ that provides the first pair of granddaughter cells and the cleavage time $t_6$ that provides the second pair of great-granddaughter cells. There is also a cell cycle duration $cc3c$ corresponding to the period between the cleavage time $t_4$ that provides the second pair of granddaughter cells and the cleavage time $t_7$ that provides the third pair of great-granddaughter cells. There is also a cell cycle duration $cc3d$ corresponding to the period between the cleavage time $t_4$ that provides the second pair of granddaughter cells and the cleavage time $t_8$ that provides the fourth pair of great-granddaughter cells. In this regard cell cycle duration $cc3$ may also be referred to as cell cycle duration $cc3a$ for consistency in terminology.

Thus, duration of cell cycles is defined as follows:
$cc1 = t_2$: First cell cycle.
$cc2$ (also referred to $cc2a$) $= t_3 - t_2$: Second cell cycle, duration of period as 2 blastomere embryo.
$cc2b = t_4 - t_2$: Second cell cycle for both blastomeres, duration of period as 2 and 3 blastomere embryo.
$cc3$ (also referred to $cc3a$) $= t_5 - t_3$: Third cell cycle, duration of period as 3 and 4 blastomere embryo.
$cc2\_3 = t_5 - t_2$: Second and third cell cycle, duration of period as 2, 3 and 4 blastomere embryo (i.e. $cc2 + cc3$).
$cc4 = t_9 - t_5$: Fourth cell cycle, duration of period as 5, 6, 7 and 8 blastomere embryo.

Synchronicities are defined as follows:
$s2 = t_4 - t_3$: Synchrony in division from 2 blastomere embryo to 4 blastomere embryo.
$s3 = t_8 - t_5$: Synchrony in division from 4 blastomere embryo to 8 blastomere embryo.
$s3a = t_6 - t_5$; $s3b = t_7 - t_6$; $s3c = t_8 - t_7$: Duration of the individual cell divisions involved in the development from 4 blastomere embryo to 8 blastomere embryo.

cc3b, cc3c, cc3d=t6-t3; t7-t4; and t8-t4 respectively: Third cell cycle for slower blastomeres, duration of period as a 3, 4, and 5 blastomere embryo; as a 4, 5 and 6 blastomere embryo, and as a 4, 5, 6 and 7 blastomere embryo respectively.

Figure 2:
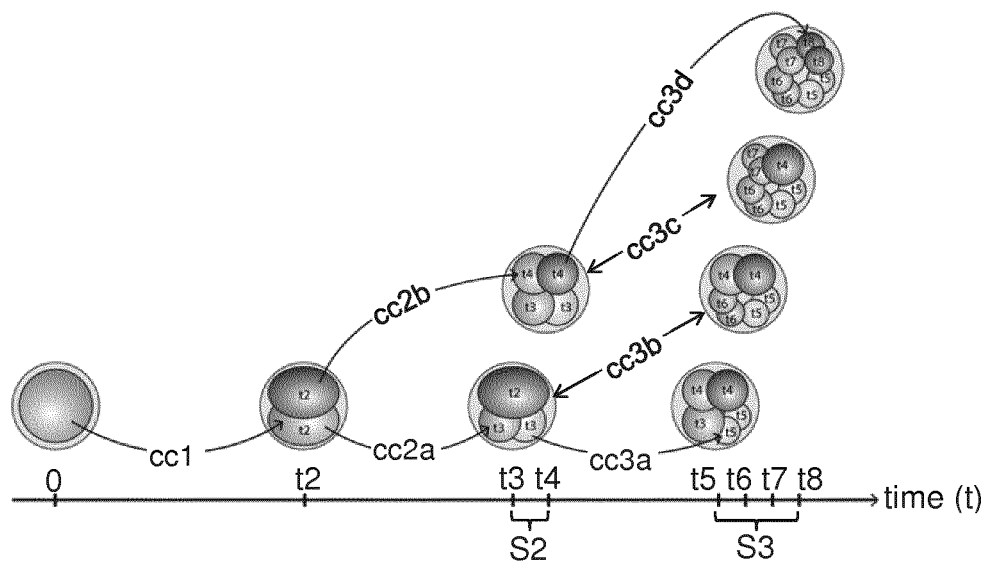
FIG. 2 schematically represents an embryo at different embryo developmental events from fertilisation (at time t=0) and at cleavage times t2-t8 with some associated aspects of timing terminology.

FIGS. 1 and 2 schematically represent some aspects of the terminology used herein regarding the timings and durations of some embryo developmental events such as discussed above. FIG. 1 shows a number of images of an embryo at various stages of development and indicates various timings associated with various developmental events, such as t2, t3, t4, t5, cc1, cc2 (which may also be referred to herein as cc2a), cc3 (which may also be referred to herein as cc3a), s2 and s3. FIG. 2 schematically represents from left to right the development of the embryo through the one, two, three, four, five, six, seven and eight blastomere stages. The times t2 to t8 at which the respective cell division stage are complete is schematically marked along the bottom axis. FIG. 2 also schematically indicates the cell cycle durations cc1, cc2a, cc2b, cc3a, cc3b, cc3c and cc3d and synchronicities S2 and S3.

Cleavage period is defined as the period of time from the first observation of indentations in the cell membrane (indicating onset of cytoplasmic cleavage) to when the cytoplasmic cell cleavage is complete so that the blastomeres are completely separated by confluent cell membranes. This may also termed the duration of cytokinesis.

Fertilization and cleavage may in some respects be considered to be the primary morphological events of an embryo, at least until the 8 blastomere stage or until the start of compaction. Cleavage time, cell cycle, synchrony of division and cleavage period are examples of morphological embryo parameters that can be defined from these primary morphological events and each of these morphological embryo parameters may be defined as the duration of a time period between two morphological events, e.g. measured in hours.

As already mentioned, it is known to establish a measure of a development potential for an embryo from various parameters associated with its development, such as parameters corresponding to (or based on) the timings discussed above, and in order to do this, values for the relevant parameters of interest may be determined from time-lapse images of the embryo as it develops through the relevant stages.

Embryo quality is a measure of the ability of an embryo to successfully implant and develop in the uterus after transfer. Embryos of high quality have a higher probability of successfully implanting and developing in the uterus to a healthy baby after transfer than low quality embryos. However, even a high quality embryo is not a guarantee for implantation as the actual transfer and the woman's receptivity influences the final result.

Viability and quality may be used interchangeably. Embryo quality (or viability) measurement is a parameter intended to reflect the quality (or viability) of an embryo such that embryos with certain values of the quality parameter (e.g. high or low values depending on how the parameter is defined) have a high probability of being of high quality (or viability), and low probability of being low quality (or viability). Whereas embryos with certain other values for the quality (or viability) parameter have a low probability of having a high quality (or viability) and a high probability of being low quality (or viability)

The term "developmental potential" may be used to reflect an estimated likelihood of an embryo to develop to blastocyst stage, to implant, to result in pregnancy, and/or to result in a live-born baby. Developmental features such as the formation of gestational sacs (GS) and onset of featal heartbeat are known to be related to the developmental potential. In some embodiments the development potential may be a determination of embryo quality. Developmental potential may be equated with embryo quality. An embryo having a positive developmental potential (i.e. a good (high) embryo quality) is one that is more likely develop to blastocyst stage and/or result in successful implantation and/or develop in the embryo in the uterus after transfer and/or result in pregnancy and/or result in a live-born baby as compared to an embryo having a negative developmental potential (or poor (low) embryo quality).

Thus embryos determined to be of good (high) quality are determined to have a higher probability of successfully implanting and/or of developing in the uterus after transfer compared with low quality embryos. However, it will be appreciated a high quality embryo is not a guarantee for implantation as the actual transfer and the woman's receptivity highly influences the final result.

In some cases the term "embryo" may be used to describe a fertilized oocyte after implantation in the uterus until 8 weeks after fertilization, at which stage it become a fetus. According to this definition the fertilized oocyte is often called a pre-embryo or zygote until implantation occurs. However, the term "embryo" as used herein will have a broader definition, which includes the pre-embryo phase. The term "embryo" as used herein encompasses all developmental stages from the fertilization of the oocyte through morula, blastocyst stages, hatching and implantation. Accordingly, the term embryo may be herein to denote each of the stages fertilized oocyte, zygote, 2-cell, 4-cell, 8-cell, 16-cell, compaction, morula, blastocyst, expanded blastocyst and hatched blastocyst, as well as all stages in between (e.g. 3-cell or 5-cell).

An embryo is approximately spherical and is composed of one or more cells (blastomeres) surrounded by a gelatine-like shell, the acellular matrix known as the zona pellucida. The zona pellucida performs a variety of functions until the embryo hatches, and is a good landmark for embryo evaluation. The zona pellucida is spherical and translucent, and should be clearly distinguishable from cellular debris.

An embryo is formed when an oocyte is fertilized by fusion or injection of a sperm cell (spermatozoa). The term embryo is traditionally used also after hatching (i.e. rupture of zona pelucida) and the ensuing implantation. For humans the fertilized oocyte is traditionally called a zygote or an embryo for the first 8 weeks. After that (i.e. after eight weeks and when all major organs have been formed) it is called a fetus. However the distinction between zygote, embryo and fetus is not generally well defined. The terms embryo and zygote may be used herein interchangeably.

An embryo that is analysed in accordance with embodiments of the disclosure such as described herein may be previously frozen, e.g. embryos cryopreserved immediately after fertilization (e.g. at the 1-cell stage) and then thawed. Alternatively, they may be freshly prepared, e.g. embryos that are freshly prepared from oocytes by IVF or ICSI techniques for example. It will be appreciated that in so far as an embryo's development has been halted by freezing, the timings of developmental events after fertilization may be defined by ignoring the time between freezing and thawing. Alternatively, a starting time may be defined as one of the first developmental events, such as exclusion of second polarbody or appearance/fading of pronuclei, post thawing.

Fertilization may be considered to be the time point where the sperm cell is recognized and accepted by the oocyte. The sperm cell triggers egg activation after the meiotic cycle of the oocyte has been suspended in metaphase of the second meiotic division. This results in the production and extrusion of the second polar body. Some hours after fusion of sperm and ovum, DNA synthesis begins. Male and female pronuclei (PN) appear. The PN move to the center of the egg and the membranes breakdown and the PN disappear (fade). This combination of the two genomes is called syngamy. Hereafter, the cell divisions begin.

The time when the pronuclei disappear may be referred to as tPNf. The terms "fade(d)" and "disappear(ed)" in relation to the pro-nuclei (PN) may be used herein interchangeably.

During embryonic development, blastomere numbers increase geometrically (1-2-4-8-16- etc.). Synchronous cell cleavage is generally maintained to the 8-cell stage or later, until compaction in human embryos. After that, cell cleavage becomes asynchronous and finally individual cells possess their own cell cycle. Human embryos produced during infertility treatment can be transferred to the recipient before 8-blastomere stage. In some cases human embryos are also cultivated to the blastocyst stage before transfer. This is preferably done when many good quality embryos are available or prolonged incubation is necessary to await the result of a pre-implantation genetic diagnosis (PGD). However, there is a tendency towards prolonged incubation as incubation technology improves.

Some example implementations of embodiments of the disclosure may be used to establish blastocyst related parameters.

A blastocyst quality criterion/measure is an example of an embryo quality criterion/measure. The blastocyst quality criteria may, for example, relate to the development of the embryo from compaction, i.e. initial compaction, to the hatched blastocyst. Compaction is a process wherein an intensification of the contacts between the blastomeres with tight junction and desmosomes result in reduction of the intercellular space and a blurring of the cell contours. Before compaction the blastomeres of the embryo can be followed individually and before compaction the embryo development follows a route of distinct and mostly synchronous cell divisions that can be observed by the naked eye and readily annotated. After compaction the embryo development is characterized by a more or less continuous development from morula to blastocyst, where individual blastomeres become difficult to track, but a number of stages may nonetheless be characterised by establishing values for parameters associated with these stages by visual inspection of images obtained for the relevant development stages.

Start of compaction (SC) describes the first time a compaction between two or more blastomeres is observed. Thus, SC marks the initiation of the compaction process.

Morula (M) is associated with the first time where no plasma-membranes between blastomeres are visible. When the compaction process is complete no plasma-membranes between any of the blastomeres forming the compaction are visible and the embryo can be defined as a morula. Most often Morula is seen after the third synchrony period S3 (i.e. after t8) close to, or right in the beginning, of the fourth synchrony period S4 (i.e. at t9), but may be earlier. Rarely do embryos cleave to 16 cells or more before compaction is initiated in human embryos.

Initial differentiation of trophectoderm (IDT) is defined as the first time where distinct trophectoderm cells are recognized. Start of blastulation (SB) is defined as the first time a fluid-filled cavity, the blastocoel, can be observed. It is also referred to as "Onset of cavitation". It describes the initiation of the transition period between the morula stage and the blastocyst stage of the embryo. Embryos often remain in this transition stage for a period of time before entering the actual blastocyst stage. The onset of cavitation usually appears immediately after differentiation of the trophectoderm cells. The outer layer of the morula with contact to the outside environment begins to actively pump salt and water into the intercellular space, as a result of which a cavity (the blastocoel) begins to form.

The full Blastocyst (B) may be defined as where there is a clear distinction between trophectoderm and inner cell mass cells. Alternatively, it may be defined in relation to the expansion of the blastocyst, for example, as a point immediately preceding the first interaction of the blastocyst with the zona pellucida (i.e. where the developing blastocyst begins to push against the zona pellucida).

Initial differentiation of inner cell mass (IDICM) defined as the first time the inner cell mass can be recognized. IDICM describes the initiation of inner cell mass development. An eccentrically placed cluster of cell connected of gab junction where the boundaries between the cells seem not well defined.

Onset of expansion of the blastocyst (EB) may be defined based on one or more parameters associated with the zona pellucida. Since expansion is a gradual process, a quantifiable definition for EB may be taken as the point at which the thickness of the zona pellucida for a given embryo has reached half the original thickness. This may be determined by measurement at different times during development.

Hatching blastocyst (HB) may be defined as the first time a trophectoderm cell has escaped/penetrated the zona pellucida or a certain fraction have hatched.

Fully hatched blastocyst (FH) is defined as when hatching is completed with shedding of the zona pellucida.

Various timings associated with blastocyst development may be defined as follows:

tM=Time from insemination to formation of morula (hours)

tSB=Time from insemination to start of blastulation (hours)

tB=Time from insemination to formation of full blastocyst (hours)

tEB=Time from insemination to formation of expanded blastocyst (hours)

tHB=Time from insemination to hatching blastocyst (hours)

Such timings also represent parameters of interest for which values may be established in accordance with some embodiments of the disclosure as described herein.

Figure 3:
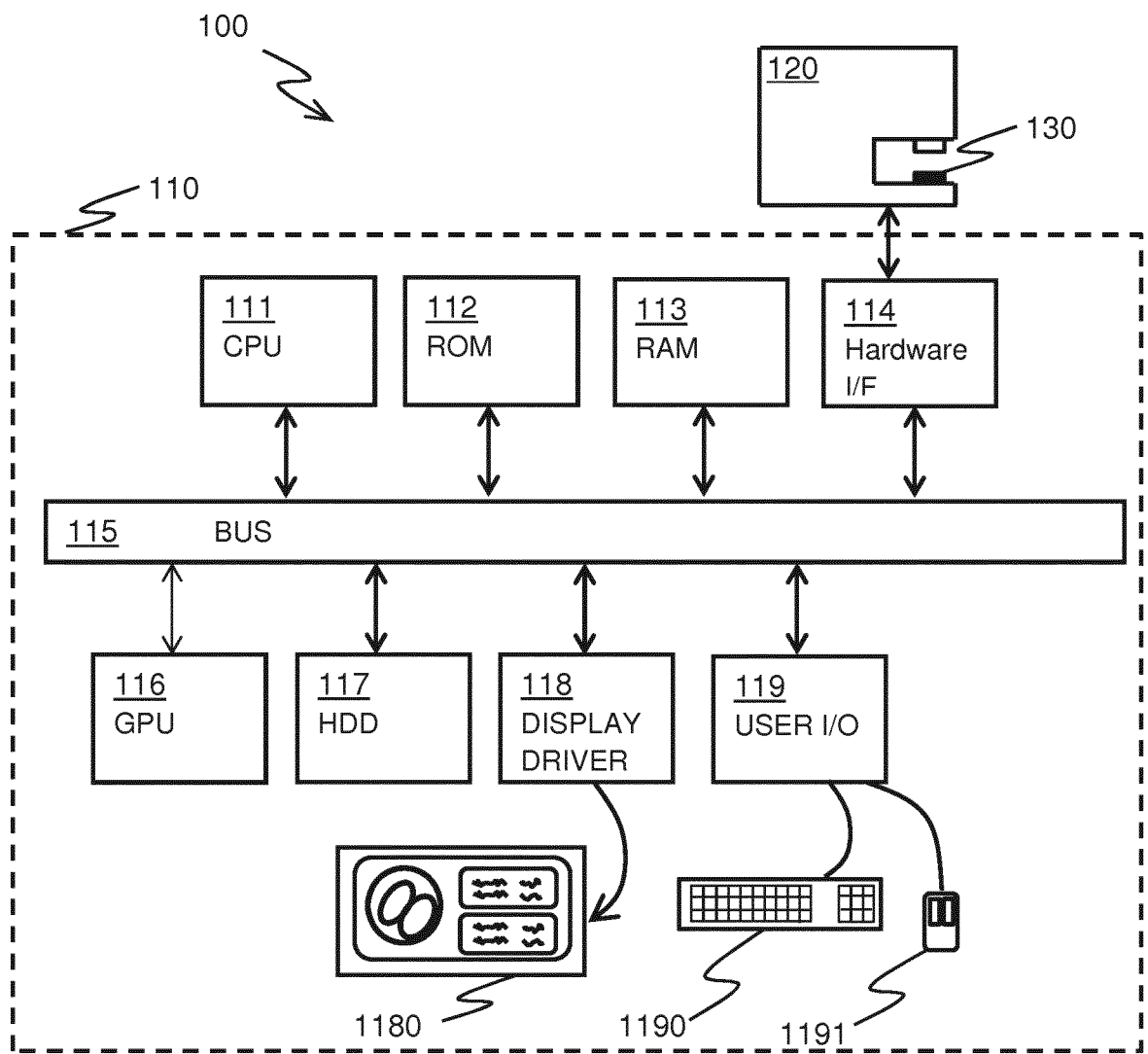
FIG. 3 schematically represents an apparatus for establishing values for parameters relating to the development of one or more embryos in accordance with some embodiments of the disclosure.

FIG. 3 schematically represents an apparatus 100 for establishing values for parameters relating to the development of an embryo 130 (for instance, parameters relating to morphokinetic events associated with the embryo) in accordance with certain embodiments of the disclosure. The apparatus 100 comprises a general purpose computer 110 coupled to an embryo imaging system 120. The embryo imaging system 120 may be generally conventional and is configured to obtain images of an embryo 130 at various stages of development in accordance with established techniques. Thus, the embryo imaging system 120 may be configured to acquire phase contrast images, Hoffman modulation contrast images, dark field images, bright field images, polarisation images, fluorescence images, confocal microscopy images, light sheet images, tomographic images, or any suitable combination thereof. As will be appreciated, many imaging modalities are known in the art, and the specific choice is not significant. What is in some cases significant is that the embryo imaging system 120 produces image information relating to one or more embryos 130 which contains information about morphological features of the one or more embryos. The images acquired by the embryo imaging system may be colour or grey-scale, and conversion of acquired images between different colour spaces may be carried out, for example via circuitry associated with the embryo imaging system, or by components of the general purpose computer 110.

It will be appreciated that in general the embryo imaging system 120 will typically be configured to obtain images of a plurality of embryos, rather than just a single embryo, over a monitoring period. For example, a typical study may involve the analysis of a number of embryos. For instance, in some embodiments, a set of 1 to 20 embryos deriving from a single individual may be contained within a single culture dish/tray/slide. The imaging system 120 may be configured to hold a plurality of such slides. For example, more than 1 slide, more than 5 slides, more than 10 slides, more than 20 slides, or more than 50 slides may be housed simultaneously within the imaging system 120. The embryo imaging system may be configured to record images of each embryo (potentially with images being taken in multiple focal planes) one at a time before moving on to image the next embryo. Once all embryos have been imaged, which might, for example, take 5 minutes, the cycle of imaging the individual embryos may be repeated to provide respective images for the respective embryos for the next time point.

The general purpose computer 110 is adapted (programmed) to execute a method for establishing values for a plurality of parameters of interest relating to the development of an embryo from a series of images of the embryo obtained at different times during its development as described further herein.

Thus the computer system 110 is configured to perform processing of embryo image data in accordance with an embodiment of the disclosure. The computer 110 includes a central processing unit (CPU) 111, a read only memory (ROM) 112, a random access memory (RAM) 113, a hard disk drive 117, a hardware interface 114, a display driver 118 and display screen 1180 and a user input/output (IO) circuit 119 with a keyboard 1190 and mouse 1191. These devices are connected via a common bus 115. The computer 110 also includes a graphics card 116 connected via the common bus 115. The graphics card includes a graphics processing unit (GPU) and random access memory tightly coupled to the GPU (GPU memory). The embryo imaging system 120 is communicatively coupled to the computer 110 via the hardware interface 114 in accordance with conventional technical techniques.

The CPU 111 may execute program instructions stored within the ROM 112, the RAM 113 or the hard disk drive 117 to carry out processing of embryo image data that may be stored within the RAM 113 or the hard disk drive 117. The RAM 113 and hard disk drive 117 are collectively referred to as the system memory. In some implementations, processing in accordance with embodiments of the disclosure may be based on embryo images obtained by the computer 110 directly from the imaging system 120. In other implementations, processing in accordance with embodiments of the disclosure may be based on embryo images previously obtained and stored in a memory of the computer 110, e.g. in RAM 113 or HDD 117 (i.e. the embryo imaging system 120 itself is not a required element of embodiments of the disclosure). In other examples, embryo images may be transferred to the computer system 110 via a network connection (for example to the internet or a local area network) or connection of external storage media (for example an external HDD, flash drive or optical storage media) via hardware interface 114. Aspects of the computer 110 may largely be conventional except that the CPU 111 and or GPU 116 are configured to run a program, which may for example be stored in RAM 113, ROM 112 or HDD 117, to perform processing in accordance with certain embodiments of the disclosure as described herein. In some embodiments the program is configured to implement one or more machine learning approaches.

Figure 4:
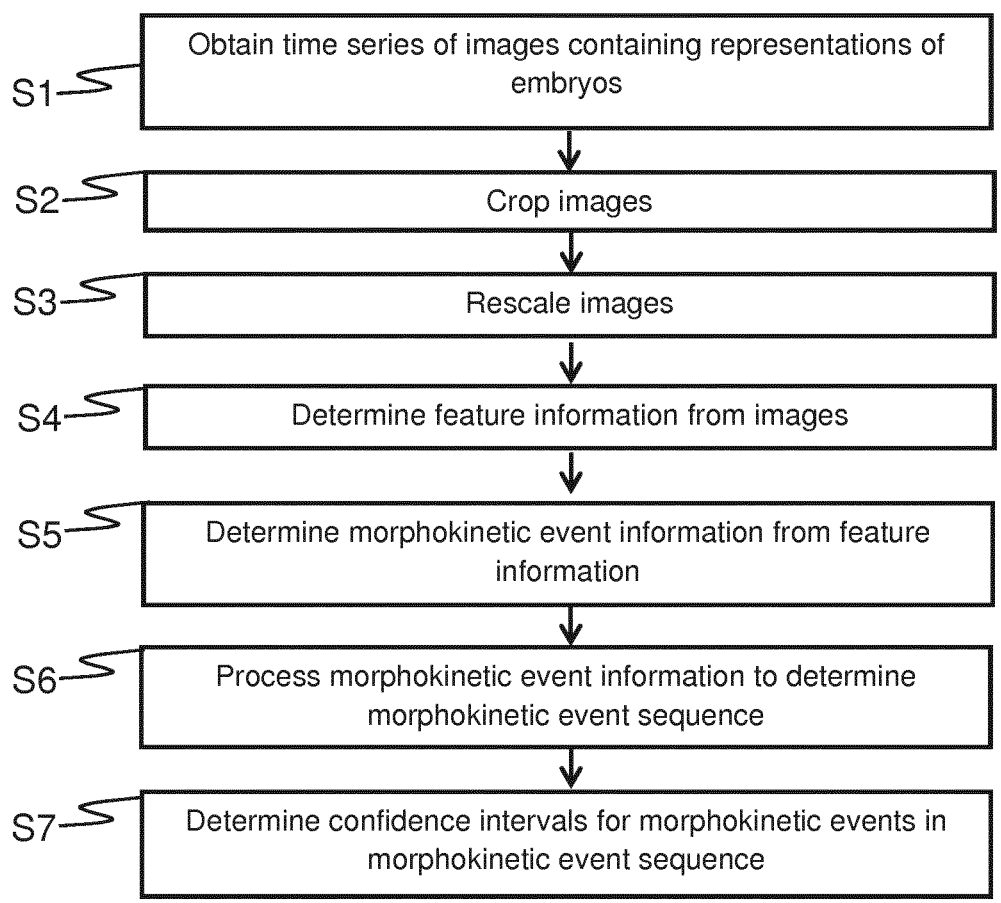
FIG. 4 schematically represents a method for establishing values for parameters relating to the development of one or more embryos in accordance with an embodiment of the disclosure.

FIG. 4 is a flow diagram which schematically represents a method of establishing values for a plurality of parameters of interest from a series of images of an embryo, said images being obtained at different times during its development (i.e. comprising a time lapse series), in accordance with some embodiments of the disclosure. It will be appreciated not all the steps discussed herein will be implemented in all implementations of approaches in accordance with embodiments of the disclosure.

Thus, in step S1 a series of images is obtained, for instance, using embryo imaging system 120, or reading previously acquired images from a storage medium such as HDD 117, RAM 113 or ROM 112. The images are characterised in that they contain representations of one or more embryos, and that the set of images forms a temporal sequence (i.e. a time lapse sequence), such that the acquisition time of each successive image in the time series is separated from that of the preceding image by a finite interval of time. For example, the times of acquisition of successive images in the series may be separated by an interval of at least one minute, such as at least 10 minutes, such as at least 15 minutes, such as at least 20 minutes, such as at least 30 minutes, such as at least 60 minutes. A series of images with these characteristics may be referred to herein as a time series, a time sequence, a time lapse sequence, or a time lapse dataset.

In step S2, one or more initial images in a time series of images (e.g. raw or pre-processed images) are cropped to generate a corresponding time series of one or more cropped images based on each respective first image, such that a number of pixels in the respective cropped images is lower than that of the respective initial images.

In step S3, one or more cropped images from a time series of cropped images is rescaled. The rescaling process generates a time series of rescaled images based on the time series of cropped images, such that one or both of the width and height of the respective rescaled images, expressed for instance as a number of pixels, is increased or decreased relative to the corresponding value in the respective cropped images.

In step S4, feature information is determined on the basis of one or more images from the time series of rescaled images. A discrete instance of feature information may be associated with each discrete image, and feature information determined on the basis of an image may be referred to herein as an instance of feature information associated with that image. Feature information associated with an image may be characterised in that it relates to features in the image from which it is derived. These features may comprise morphokinetic descriptions and/or features derived using image analysis/computer vision approaches. The features may relate to embryo developmental events, but may be more abstract features, such as relating to statistical analyses of the images, such as a measure of the degree of variation in pixel values or a measure of contrasts in the image. Thus, in some embodiments, feature information may represent an abstracted and/or higher-level representation of features comprising an image. In other embodiments, an instance of feature information associated with an image may comprise the image itself (i.e. the feature information may comprise an array of pixel values corresponding to the image itself). The format used to denote and store an instance of feature information may be a vector or array of numeric values, an image format, or any suitable format for defining and storing information. A discrete instance of feature information may be determined for each respective image in a time series of images, such that the instances of feature information form a time series which is related to the time series of images, being determined based on the time series of images. As the skilled person will appreciate, instances of feature information may be derived from images acquired and processed in accordance with step S1 with or without steps S2 and S3 or other further processing.

In step S5, morphokinetic event information is determined on the basis of a time series of instances of feature information, such as a time series of feature information determined in step S4. Morphokinetic event information is information about morphokinetic events and/or morphokinetic stages relating to embryo development, and may include numeric parameters relating to, for example, a cleavage time, a cleavage period, a cell cycle duration, a cell stage duration, or any other parameter known for describing morphokinetic events and/or stages of embryo development. In some instances, an instance of morphokinetic event information determined for a given instance of feature information may comprise one or more likelihood values respectively assigned to one or more morphokinetic parameters, whereby each of said likelihood values indicates the likelihood that the respective morphokinetic parameter is associated with the embryo as represented by the given instance of feature information. Thus for a time series of instances of feature information such as described with reference to step S4, a time series of instances of morphokinetic event information may be determined in step S5.

In step S6, instances of morphokinetic event information from a time series of instances of morphokinetic event information (such as described with respect to step S5) are processed to determine a morphokinetic event sequence. A morphokinetic event sequence is information relating to a sequence of morphokinetic events, and may comprise information about types of events/cycles/stages associated with embryo development, along with respective timing information. For example, in one embodiment, a morphokinetic event sequence comprises information about timings of embryo transition events. For example, a morphokinetic event sequence may comprise a sequence of cleavage events and timings, such as a determination of values for cleavage times t2, t3, t4, t5, t6, t7, t8, t9 and more generally tn. Other morphokinetic events determined in step S6 may include start of compaction (SC), fading of pronuclei (tPNf), morula (M), initial differentiation of trophectoderm (IDT), start of blastulation (SB), blastocyst (B), initial differentiation of inner cell mass (IDICM), onset of expansion of the blastocyst (EB), hatching blastocyst (HB), fully hatched blastocyst (FH), appearance of first polar body, appearance of second polar body, appearance of first pronuclei, appearance of second pronuclei, time of pronuclei alignment, start of blastocyst collapse, and start of blastocyst re-expansion.

In one embodiment, the timing information associated with a morphokinetic event is information about an absolute time at which the respective morphokinetic event occurred. In another embodiment the timing information is information about a time interval between two or more morphokinetic events in a morphokinetic event sequence.

In step S7, confidence information is determined for one or more morphokinetic events in a morphokinetic event sequence as described with reference to step S6. The confidence information may comprise a confidence interval or other confidence/likelihood measure associated with each of one or more morphokinetic events comprising a morphokinetic event sequence. What is in some cases significant about the confidence interval for some examples is that it provides a measure of the degree of certainty associated with the determination of the timing of a given morphokinetic event.

A more detailed description of embodiments of the disclosure in accordance with steps S1 to S7 in FIG. 4 is given below.

An embryo 130 in accordance with certain example implementations is monitored regularly using the embryo imaging system 120 in order to obtain a series of time-lapse images (typically the embryo imaging system will obtain a series of time-lapse images for a plurality of embryos, for example for up to 6 or more patients with up to 12 embryos per patient). The embryo may be monitored (imaged) at least once per hour, such as at least twice per hour, such as at least three times per hour, such as at least four times per hour, such as at least six times per hour, such as at least 12 times per hour. The monitoring may be conducted while the embryo is situated in an incubator used for culturing the embryo. This may be carried out through image acquisition of the embryo in accordance with any established time-lapse imaging method known in the art.

The dimensions and characteristics of the acquired images may be selected based on the capabilities of the imaging system, for instance, the properties of the sensor used to collect the images may determine the dimensions of the raw images. For example, in one embodiment a sensor array may acquire images having a width of 1280 pixels and a height of 1024 pixels (i.e. 1280×1024 pixels). In other embodiments, the acquired images may have dimensions of 224× 224 pixels, 500×500 pixels or 800×800 pixels. It will be appreciated that the term 'image' as used herein, and associated with an acquisition time T, may be used to refer to a plurality of frames (i.e. layers or sub-images) significantly associated with the same acquisition time and/or representation of features. Thus, for instance, in some embodiments, an image may comprise n frames/layers acquired at time T and associated with n different colour channels, for example, each of a red channel, blue channel and green channel. In other embodiments, an image may comprise a plurality of frames acquired at different focal planes. As the skilled person will readily appreciate, imaging systems (i.e. microscopes) capable of imaging in more than one focal plane are known in the art. Thus, in one embodiment, an image associated with a given time T may comprise 11 frames acquired at different focal planes and acquired at or around time T. In some embodiments, the plurality of frames comprising an image may be acquired simultaneously (i.e. in parallel), whereas in other embodiments the plurality of frames may be acquired in series. What is in some cases significant is that the frames/layers comprising an image associated with a time Tare significantly associated with the time T such that they can be assumed to be representations of an embryo in the same state (in terms of, for example, embryo features). It will be appreciated that an image may comprise any number of frames associated with different colour channels and/or focal planes. A suitable selection of frames to be used in a given implementation may be determined, for example, using modelling or experimentation (i.e. by assessing the performance of the methods disclosed herein when for different selections of frames). The skilled person will appreciate that many sizes of image may be acquired. What is significant for some implementations is that dimensions, effective resolution, and number of frames of the acquired images are selected such that features relating to embryo developmental events (for example morphokinetic events/cycles/stages) are discernible within each image. It will be appreciated that computer-assisted approaches may be able to discriminate features in images that are not perceptible to human vision. Since the effective resolution and size of the images may influence the computational resources required for image analysis, the selection of suitable image parameters may involve an optimization process. The goal of the optimization process may be to determine an appropriate compromise between the detail of features contained in the acquired images and the computational cost of later image analysis steps, for instance, machine learning approaches used to process said images. This optimization process may involve modelling and/or experimentation.

Figure 5:
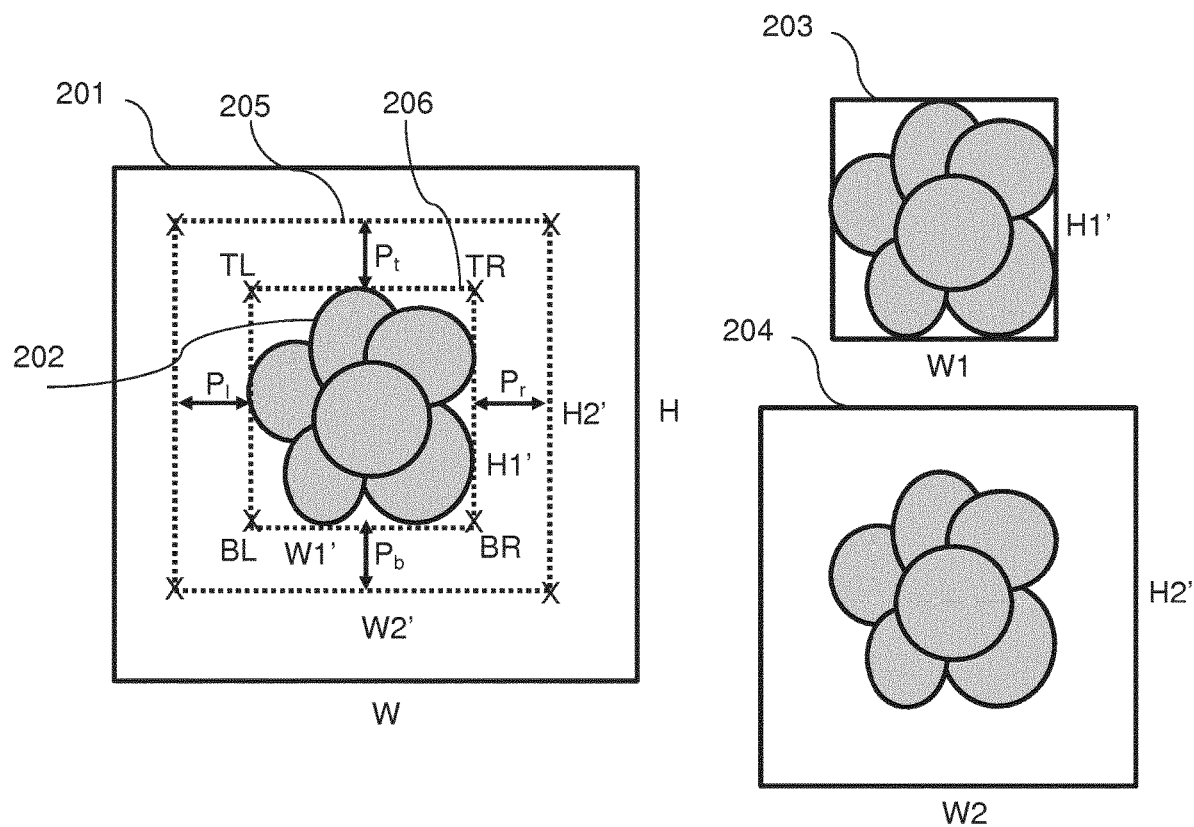
FIG. 5 schematically represents a method for cropping an image of an embryo to reduce the number of pixels comprising the image.

FIG. 5 schematically shows an image 201 containing a representation of an embryo 202, the image 201 having a width W and a height H. Image 201 may be acquired, for example, using imaging apparatus 120. Features relating to the development of embryo 202 are visible in the image in schematic form (for instance the number of cells and the positions of cell boundaries). In some embodiments, a cropping step is applied to image 201, which the skilled person will understand to mean the step of generating a second image based in image 201 but in which a sub-set of pixels from image 201 have been discarded. In FIG. 5, images 203 and 204 schematically represent examples of cropped images derived by applying a cropping step to image 201. In one embodiment image 201 is cropped using a rectangular region of interest (ROI), such as ROIs 205 and 206 in FIG. 5. The geometry and position of a ROI may be defined with respect to four vertices, labelled TL, TR, BL, and BR for clarity, and situated within the borders of the image 201. These vertex labels denote top left, top right, bottom left and bottom right vertices respectively. A ROI used for cropping image 201 is referred to herein as a cropping ROI, and has a width W' and height H', defined, for example, in terms of a number of pixels. By defining the dimensions and position of the cropping ROI relative to the image 201 to be cropped, a defined subset of the pixels in the first image, contained within the boundary of the cropping ROI, can be exported as a second image. A second image generated from a first image using a cropping ROI is referred to herein as a cropped image. Thus, in FIG. 5, cropped image 203 has been generated from image 201 using cropping ROI 206, and cropped image 204 has been generated from image 201 using cropping ROI 205. In one embodiment, a cropped image is generated from a first image 201 such that a representation of an embryo 202 within the first image is entirely conserved in the cropped image. In other words, the cropping ROI used to define the cropped image may substantially enclose within its border the set of pixels in the first image which correspond to embryo features. What is significant about the cropping step in some examples is that a cropped image contains representations of embryo features from a first image, and is smaller than the first image (i.e. having fewer pixels) whilst conserving the effective resolution of the first image. In other words, cropping does not necessarily entail a rescaling of the image.

In one embodiment, one or more of a sequence of images of embryos are cropped via a user-guided process. The user may be an embryologist. A set of images may be acquired using imaging apparatus 120, or read from a data storage apparatus such as HDD 117 or RAM 113. In one embodiment, an image (such as image 201 in FIG. 5) is selected from a set of images and displayed to the user on a graphical display, such as display screen 1180 in FIG. 3. An input device such as input devices 1190 and 1191 in FIG. 3 may then be used to manually define a cropping ROI within the image, for example, by clicking at four positions within the border of image 201 to define four vertices of a cropping ROI using input device 1191. For example, with reference to FIG. 5, the user may determine the positions of the vertices TL, TR, BL and BR by clicking within a representation of image 201 displayed on display screen 1180 (it will be appreciated a rectilinear cropping region may also be defined by a user clicking at just two points, for example at diagonally opposite corners of the desired cropping region). The dimensions of the ROI (i.e. W' and H') may be defined by the user, for example using input device 1190. The position of the cropping ROI may be adjusted, for example using input device 1191, to determine a suitable position within image 201. In some embodiments, the user may set the cropping ROI dimensions (W' and H'), then 'drag' a graphical overlay representing the dimensioned ROI to a position within the border of image 201 such that a representation of an embryo 202 in the image 201 is substantially centered within and enclosed by the boundaries of the cropping ROI.

In some instances, the height H' and width W' of the cropping ROI may be determined by multiplying the dimensions of the image 201 by a scaling factor. For example, in one embodiment the scaling factor is 0.7, and the dimensions of the cropping ROI are determined via the expressions $W'=0.7 \cdot W$ and $H'=0.7 \cdot H$. FIG. 5 schematically shows a cropping ROI 205 whose dimensions have been determined using a scaling factor. This results in a ROI in which a padding distance P exists, being the distance, perpendicular to the side, between a given side of the cropping ROI and the closest pixel from the set of pixels representing the embryo 202. Thus, with reference to FIG. 5, ROI 205 is characterized in that padding distances Pt, Pb, Pr and Pl exist between, respectively, the top, bottom, right and left sides of the ROI and, respectively, the uppermost, lowermost, rightmost and leftmost extents of the set of pixels representing embryo 202. In other embodiments, the padding distances Pt, Pb, Pr and Pl may be set to any suitable values that provide a border of background pixels around the embryo in the cropped image generated from the cropping ROI.

Figure 6:
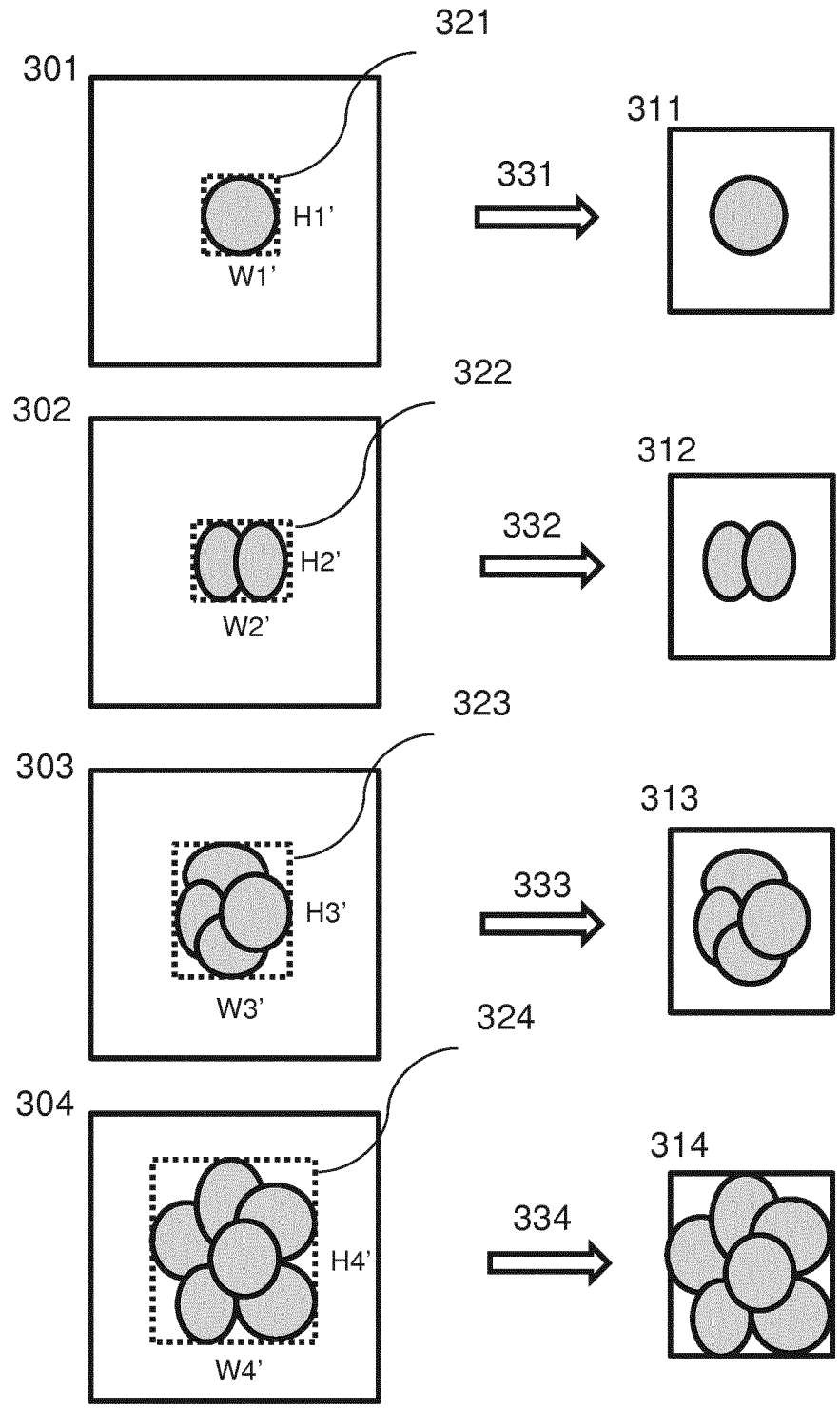
FIG. 6 schematically represents a method for cropping a sequence of images of an embryo acquired at different stages during the development of the embryo.

In another example, the height and width of the cropping ROI are selected by the user following visual inspection of embryo representations in multiple images and/or multiple sequences of images. In this instance, a single set of cropping ROI dimensions W' and H' is conserved across the cropping steps applied to a plurality of images. The dimensions of the cropping ROI may be selected such that all the visible features of the largest embryo observed in the set of images to be cropped lie within the ROI boundary. FIG. 6, which will be understood from FIG. 5, schematically shows a sequence of images of embryos 301, 302, 303 and 304, which are each cropped using a cropping ROI with the same dimensions (i.e. W4' and H4') in respective cropping steps 331, 332, 333 and 334, generating a sequence of respective cropped images 311, 312, 313 and 314. In this instance, the width W' and height H' of an initial cropping ROI in each image is first recorded, said initial cropping ROI being determined by selecting dimensions and position which substantially enclose the representation of the embryo in that image. Thus, for example, for image 301 an initial cropping ROI 321 is determined which substantially encloses the representation of the embryo in image 301. This determination can be made using any suitable technique, such as those discussed in this disclosure. Once an initial cropping ROI width W' and height H' have been determined for all images 301, 302, 303 and 304 in the sequence, the recorded widths and heights of all initial cropping ROIs are assessed to determine the maximum width W' and maximum height H' observed across the entire set of initial cropping ROIs. Thus, in FIG. 6, the initial cropping ROI 324 in image 304 is determined to have both the largest width W' and the largest height H' of any of the cropping ROIs 321, 322, 323 and 324, having a width W4' and height H4'. Thus a final cropping ROI with width W4' and height H4' is defined as the cropping ROI used to crop all images in the series, and is thus used to crop each of the images 301, 302, 304 and 305 in respective cropping steps 331, 332, 333 and 334. Hence, in a cropping step 331, image 301 is cropped using a cropping ROI with width W4' and height H4' to generate cropped image 311. Likewise, in cropping step 332, image 302 is cropped using a cropping ROI with width W4' and height H4' to generate cropped image 312.

In some embodiments, one or more first images from an image sequence may be cropped using an approach in which one or more representations of embryos in the image are first labelled via pixel classification. The goal of this approach is to produce a simplified representation of one or more embryo features in an image, which can be used to determine parameters for defining dimensions and/or position of a cropping ROI. The classification step may involve determining, for instance, that one or more pixels in an image correspond to a representation of an embryo and one or more pixels do not correspond to a representation of an embryo. This form of approach may be referred to as a segmentation approach. In one example of a segmentation approach, two classes are defined to describe image pixels, an 'embryo' class for pixels corresponding to embryo features, and a 'background' class for pixels not corresponding to embryo features. Thus, with reference to FIG. 5, a segmentation approach may assign all pixels in image 201 associated with features of the embryo 202 to an 'embryo' class, and all remaining pixels not assigned to the 'embryo' class to a 'background' class.

Examples of segmentation methods known in the art include manual annotation methods, threshold-based methods, histogram-based methods, clustering methods, region-growing methods, watershed methods, model-based methods, edge-detection methods, and machine-learning methods. However, as will be appreciated, the most suitable method may depend on specific properties of the images to be segmented, and upon constraints imposed by time and available computational resources, such as, for example, the computational resources of computer system 110 (such as the memory of RAM 113 and HDD 117, and the processing capabilities of CPU 111 and/or GPU 116).

In one embodiment, a user assigns pixels to one or more classes by manual annotation. The user may be an embryologist. An image, such as image 201, containing a representation of an embryo 202, may be displayed on a graphical display such as display 1180 in FIG. 3, and an input device such as input devices 1190 and 1191 used to assign one or more pixels to one or more classes. In one embodiment, a user may use an input device to define a closed polyline approximating the outline of the embryo representation in the image. The path of the polyline may thus approximate the visible interface between the set of pixels representing an embryo in the image and the set of pixels representing the non-embryo background. The user may then use an operator defined within computer 110 to assign all pixels enclosed within the closed polyline to an 'embryo' class, and all other pixels to a 'background' class. This information about the pixel classes may be referred to as label information for a given image. In one embodiment, label information may comprise an image with the same dimensions as the image from which it is derived, and in which pixels assigned to the 'embryo' class are assigned a first value (e.g. '1') and pixels assigned to the 'background' class are assigned a second value (e.g. '0'). This may be referred to as a mask image, or a label-field image. Alternatively, label information may comprise a data structure associated with the image, such as a vector or array in which pixel coordinates are associated with a label indicating a class to which they are assigned.

In another embodiment, pixels may be assigned to an embryo class and a background class using an automated computer implemented approach, such as a histogram-based approach. In one embodiment, a histogram of pixel intensity is derived for an image 201, which is information about a distribution of pixels with respect to a pixel intensity range for the image. The intensity range may be the range of intensity values between the intensity of the lowest intensity pixel within the image and that of the highest intensity pixel within the image. The value associated with a given intensity or range of intensity is the frequency of pixels in the image corresponding to that intensity value or range of intensity values. Such a distribution may be characterized by having one or more peaks. In one instance, there may be two peaks, one of which is significantly associated with embryo pixels and the other of which is significantly associated with background pixels. A suitable method may be used to determine a threshold value, which can be considered a separation value between a range of pixel intensity significantly associated with embryo pixels and a range of pixel intensity significantly associated with background pixels. Many approaches to determining a threshold value from a histogram are known in the art, including Otsu's method, Shanbhag's method and various minimum error methods. Via such a method, one or more (e.g. all) the pixels in the image may be classified on the basis of whether their intensity values fall above or below this threshold value.

In some embodiments, a machine learning approach is used for segmentation of embryo representations within images. As the skilled person will appreciate, a number of machine learning approaches are known in the art which can be applied to image segmentation tasks, including support vector machines, graphical models, random forest classifiers, clustering approaches and neural network approaches. The term 'machine learning algorithm' may herein be used interchangeably with 'machine learning approach', and will be understood as referring in many cases to any approach, method, or system which takes one or more inputs, processes the input to produce one or more outputs, and is able to modify some aspect of the processing based on an assessment of the validity of the output relative to a target (i.e. in some instances the approach may be considered to be iteratively trainable). The target may be defined on the basis of label information associated with the one or more training inputs. The operators comprising the approach may comprise mathematical functions, for example computer-vision operators, kernel-based operators, statistical operators, summation functions, convolution/deconvolution operators, pooling operators, and activation functions. Any number of operators may be connected together such that one or more outputs of a first operator are provided as inputs to one or more second operators. The machine learning approach may also comprise fixed or modifiable parameters such as weighting coefficients or biasing coefficients which can be used to modify the behavior of operators comprising the approach, and/or modify inputs and outputs as they are passed between operators. It will be appreciated that what is significant about certain machine learning approaches is that performance of a task, applied to one or more inputs, can be improved by modification of the approach without the requirement to explicitly program all the steps and/or parameters of the task. A machine learning approach may be considered a heuristic or non-handcrafted approach.

In some embodiments the machine learning task comprises the classification of pixels from an input image into one of two classes, denoted the 'embryo' class and the 'background' class (i.e. embryo segmentation). The input for the machine learning task is an image of an embryo, or other information about the spatial location and/or intensity of pixels comprising an image of an embryo. The output of the machine learning approach may be a binary indication defined for one or more respective input pixels, in which '1' indicates that the respective pixel is considered to belong to the embryo class, and '0' indicates that the respective pixel is considered to belong to the background class.

Figure 7:
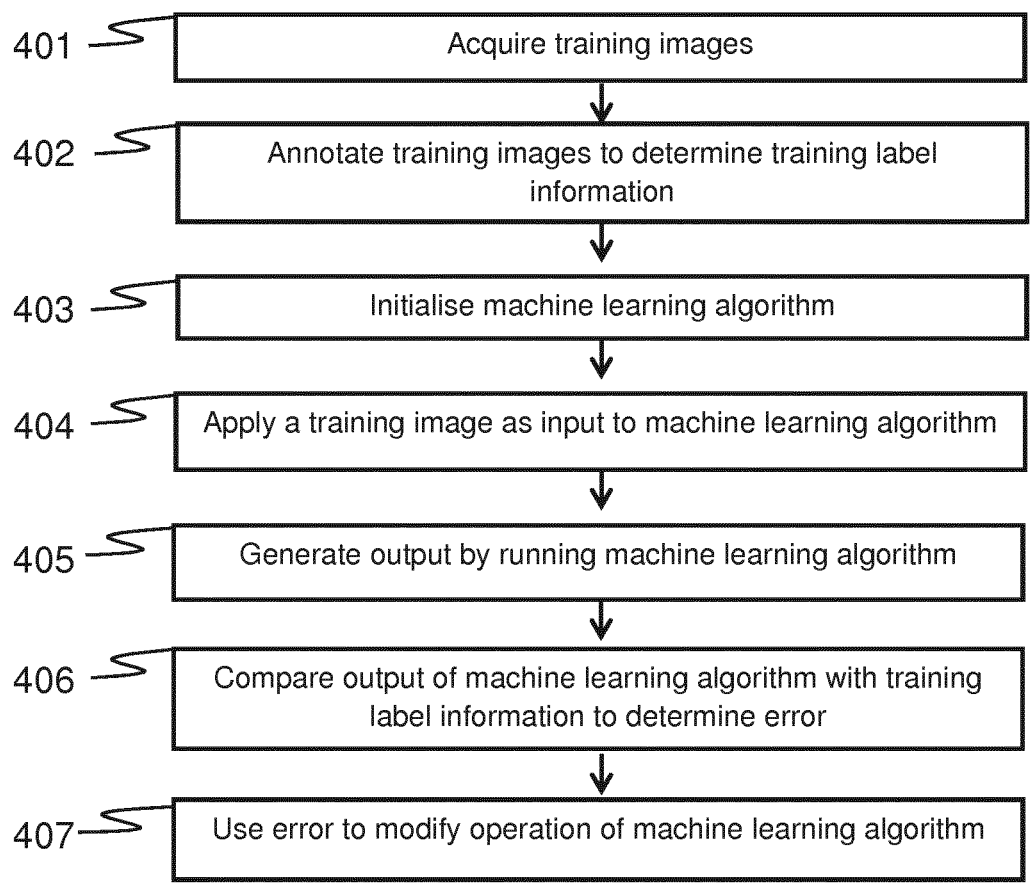
FIG. 7 schematically represents a method for configuring a machine learning approach for use in classifying pixels in an image of an embryo.
Figure 8:
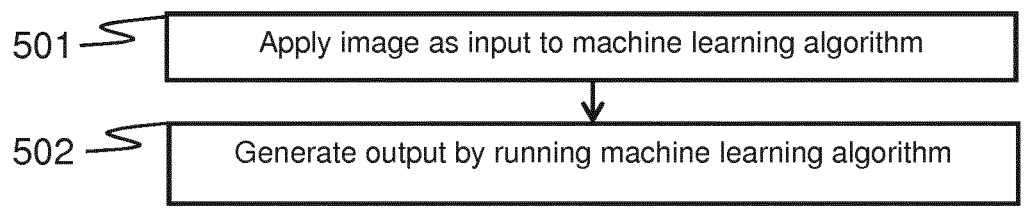
FIG. 8 schematically represents a method for classifying pixels in an image of an embryo using a machine learning approach.

FIGS. 7 and 8 schematically show approaches to segmentation of images using a machine learning approach in accordance with an embodiment of the present disclosure.

Figure 9:
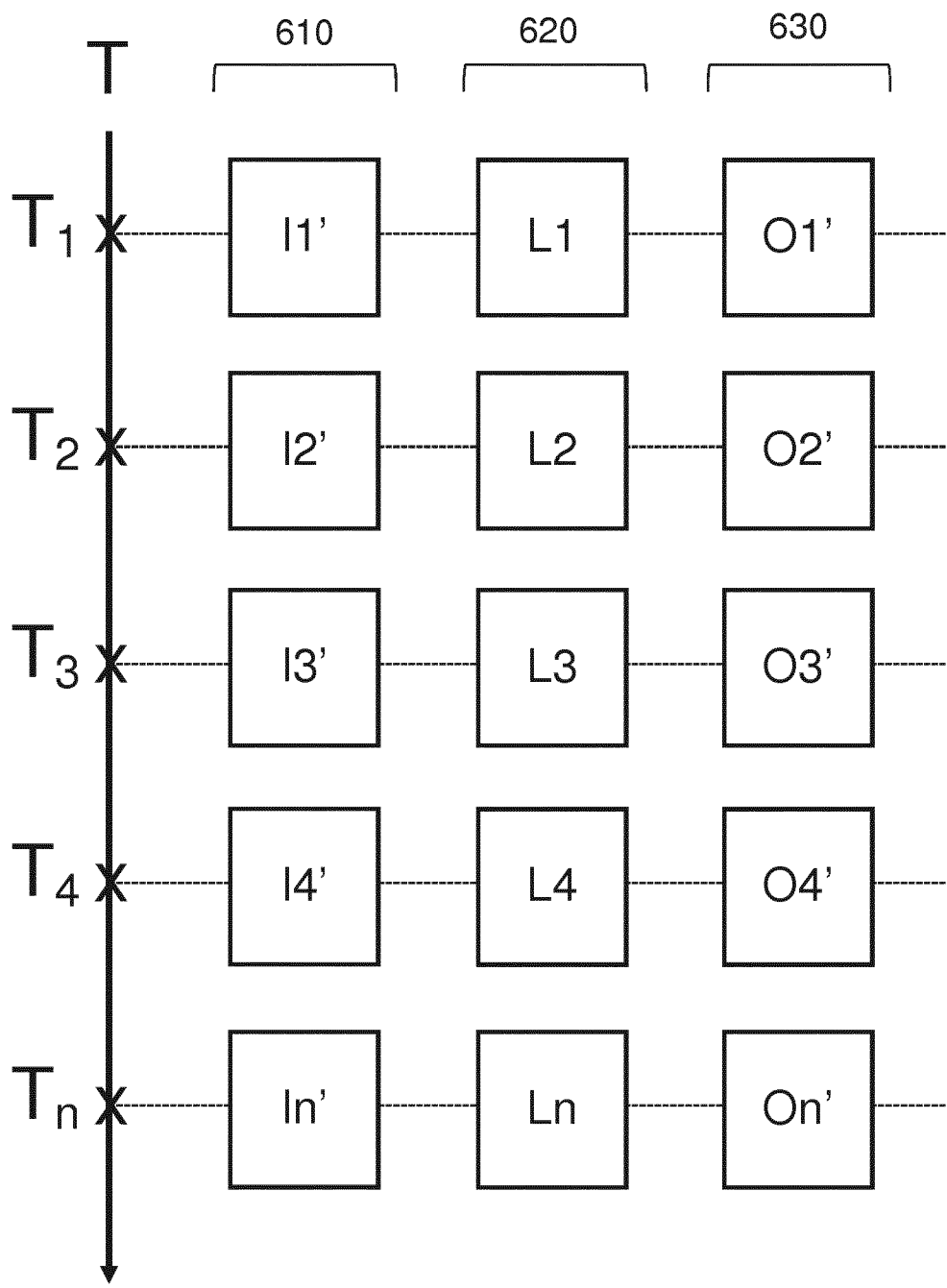
FIG. 9 schematically represents a time series of training images of embryos and associated time series of training label information and machine learning outputs.

Thus in step 401, a set of training images is acquired which may comprise a set of images of embryos acquired under similar conditions to a time series of images to be segmented using the machine learning approach. These images may have been acquired using an imaging apparatus such as apparatus 120 in FIG. 3. In FIG. 9, a set 610 of n training images (I1' to In') is shown schematically. The prime symbol indicates that the image is a training image used during the preparation (i.e. training) of the machine learning approach. Dashed lines in FIG. 9 indicate the association of each training image I' to a time of acquisition, such that, for example, training image I1' is associated with acquisition time T1. Though the set of training images 610 comprises a time lapse sequence of images at different stages of embryo development, it is not necessary that all the training images comprise images of the same embryo, or are acquired at specific times or time spacings.

In step 402, each training image I' is annotated to associate it with training label information L indicating a target class associated with one or more pixels in the respective training image. In FIG. 9, a set 620 of n training images (L1 to Ln) is shown schematically. Dashed lines indicate the association of each instance of training label information L to a training image I' and an acquisition time T, such that, for example, training label information L2 is associated with training image I2' acquired at T2. The combination of a set of training images 610 and set of instances of training label information 620 associated with each respective training image may be termed a training dataset. The training label information may be related to a task the machine learning approach is configured to perform. For instance, if the objective (i.e. task) of the machine learning approach is to assign each of a set of pixels comprising an input image to one of two target classes, a training dataset may comprise one or more input training images I', each of which has associated training label information L indicating to which of the target classes each (or at least some) of the pixels comprising the respective training image I' belongs.

Thus in one embodiment, the training dataset comprises a plurality of training images 610 containing representations of embryos, and an instance of training label information associated with each of the training images I' 610 indicating which pixels of I' are assigned to the embryo class, and which pixels from I' are assigned to the background class. The association of training label information L with a training image I' may be called annotation. Annotation may be carried out manually by a user, for example, an embryologist, using a general purpose computer such as computer 110, having a graphical user interface such as display screen 1180 and one or more input devices such as devices 1190 and 1191. In one scenario, an embryologist may display an image of an embryo, such as image 201 shown schematically in FIG. 5, on a graphical user interface. If the target of the machine learning algorithm is to assign pixels to either the 'embryo' class or the 'background' class, the embryologist may use a manual, semi-automated or automated segmentation approach such as described above to assign one or more pixels in a training image to either the embryo class or the background class. Resulting data assigning a class to one or more pixels in a training image belongs may be considered to comprise an instance of training label information L associated with a given training image I'. The training label information may be stored in a suitable data structure, for example an image, a vector or an array of numeric values. In one embodiment the training label information comprises an image with the same dimensions as the training image to which it corresponds, and in which pixels corresponding to embryo features in the training image are assigned the value '1' and pixels corresponding to the background are assigned the value '0'. In another embodiment, a 3×n array may be used to store training label information, where n is the number of annotated pixels, and wherein for the nth row of the array, the first column cell indicates the x coordinate of the nth pixel, the second column cell indicates the y coordinate of the nth pixel, the third column cell contains '1' or a '0' indicating whether the nth pixel is assigned to the 'embryo' class (e.g. indicated by a '1') or the 'background' class (e.g. indicated by a '0'). Of course other data structures may be used. For example, a 2×m array may be used to indicate the x- and y-coordinates of m pixels assigned to one class, with it being assumed all the other pixels are assigned to the other class. Thus, the specific format of the training label information is not significant, what is in some cases significant about the annotation of training images is that the training label information provides information about a target state for a classification of at least some of the pixels in an image. Thus the skilled person will appreciate that a training dataset may comprise any number of training images containing representations of one or more embryos, and associated training label data which provides class information about pixels in the training images. Such information can be acquired using any know approaches for image acquisition and segmentation. For example, in other embodiments, the annotation may be carried out using an automated- or semi-automated image segmentation technique such as those described above.

In step 403, the machine learning approach is initialised. In some embodiments the machine learning approach comprises using a support vector machine. In some embodiments the machine learning approach comprises a graphical model such as a Markov random-field model or a Bayesian model. In some embodiments the machine learning approach comprises the use of feature quantification combined with a random-forest classifier. In some embodiments the machine learning approach comprises a feature clustering approach, such as K-means clustering. In some embodiments the machine learning approach comprises an artificial neural network. The machine learning approach may be configured to be implemented on a general purpose computer such as the general purpose computer 110 shown in FIG. 3. The machine learning algorithm may be configured to run on a CPU, such as CPU 111 shown in FIG. 3, or a GPU such as GPU 116 shown in FIG. 3. The skilled person will recognise that the machine learning approach may be configured to run within any suitable machine learning framework known in the art, such as TensorFlow, Theano, Torch, Caffe, or the Waikato Environment for Knowledge Analysis. Alternatively the approach may be programmed by the using a suitable programming language, for example, Python or C++. The machine learning approach may be configured to run on CPU 111 or GPU 116 of general purpose computer 110 shown in FIG. 110.

Also in step 403, a configuration of operators, functions, weights, biases, and other parameters relating to the operation of the machine learning approach may be selected. For example, in one embodiment the machine learning approach comprises an artificial neural network, and the configuration of the approach may comprise selecting a number of layers, selecting a number of nodes per layer, selecting and configuring activation functions, selecting and configuring weighting coefficients (or 'weights') selecting and configuring biasing coefficients (or 'biases'), selecting and configuring convolution operators, selecting and configuring pooling operators, selecting and configuring sub-sampling operators, selecting and configuring rectifying operators, selecting and configuring one or more classification layers. Suitable operators and parameters values may be selected, for example, based on experimentation or modelling.

The configuration of the machine learning approach in step 403 will generally be conducted such that the output of the machine learning approach is related to the task/objective of the machine learning approach. For example, in one embodiment the task is to classify input pixels from an input image to determine with which of one or more target classes each pixel should be associated. Thus in this embodiment, the machine learning approach may be configured such that the output comprises likelihood information associated with each input pixel, and wherein the likelihood information is information about a likelihood of the pixel belonging to each of the one or more target classes.

Steps 404, 405, 406 and 407 comprise a training stage, which may be iterated over a plurality of times in order to train the machine learning approach to carry out the task to a desired level of performance. In some embodiments, the objective of the training task is to minimize (reduce to a desired threshold) the error between the label information associated with an input image, and the output generated by applying the machine learning approach to the input image. The error may be minimized with respect to a plurality of training stages applied to a single input training image, or a plurality of training stages applied to a plurality of input training images.

Figure 10:
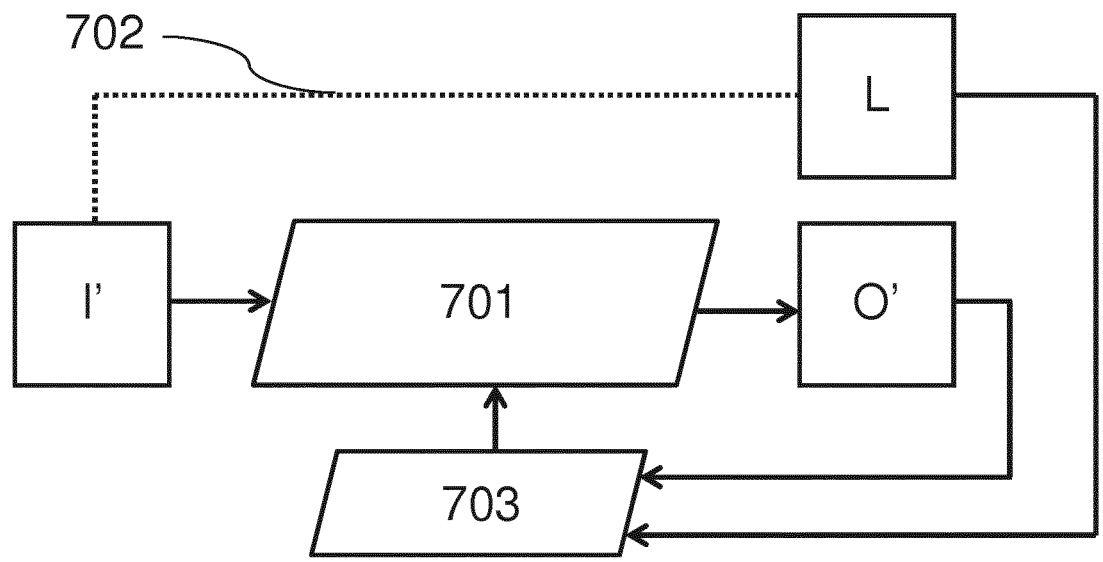
FIG. 10 schematically represents a method for training a machine learning approach to classify image pixels.

Thus in step 404, a training image is selected from a set of training images acquired in step 401 (such as set 610 in FIG. 9), and applied as an input to the machine learning approach. For example, in one embodiment the machine learning approach is a convolutional neural network (CNN), and the training image is supplied as an input to the input layer of the CNN. FIG. 10 schematically shows a training image I' being applied as an input to machine learning approach 701.

In step 405, an output is generated by applying the machine learning approach to the input image. FIG. 10 schematically shows an output O' generated by machine learning approach (algorithm) 701 on the basis of input image I'. In one embodiment the machine learning approach 701 comprises a CNN (for example, a U-NET) and the output O' comprises a 2D array of values (i.e. an image) with the same dimensions as the input image I'. Each pixel in the output O' has been assigned a class estimate value by the machine learning approach 701. For example, the class estimate value may be a numeric value between '0' and '1', where the value is related to a probability that the pixel is determined to be associated with either the embryo class or the background class. For example, a value of '0.1' may indicate a relatively high probability that the pixel is associated with the background class, and a value of '0.9' may indicate a relatively high probability that the pixel is associated with the embryo class. A value of '0.5' may indicate an even probability of the pixel belonging to either class. The particular choice of format for the output is not particularly significant and what is in some cases significant about the output is that it provides information on the likelihood of each of a set of input pixels belonging to each of one or more target classes regardless of how the output is formatted/structured.

In step 406, the output O' is compared to label information L associated with the input training image I'. The objective of this comparison is to determine how closely the output O' of the machine learning approach 701 matches the label information L. In one embodiment, this comparison is used to determine an instance of error information, which is information quantifying the magnitude/degree of difference between the output and the label information. This comparison may be achieved in any manner known to the skilled person, for example, through use of an appropriate error function such as a cross-correlation function. FIG. 10 schematically shows training label information L (associated with input image I' as denoted by a dashed line 702) and output O' from machine learning approach 701 being provided as inputs to a comparison step 703.

In step 407, the error information determined in step 406 is used to modify the operation of the machine learning approach 701. FIG. 10 schematically shows the output of a comparison 703 between training label information L and output O' being used as an input to modify the machine learning approach 701. The modification is carried out with the aim that re-applying steps 404, 405 and 406 using the same training image I' and the modified machine learning approach 701 results in a lower error between the output O' and the label information L, as determined by comparison 703. For example, the machine learning approach 701 may comprise a plurality of operators and a plurality of parameters, and these may be adjusted during step 407. In one embodiment, the machine learning approach comprises one or more decision trees, and parameters associated with one or more of the decision trees may be adjusted during step 407. In another embodiment, the machine learning approach comprises a neural network (e.g. a UNET), and a gradient descent or other backpropagation approach is used to update weight values associated with the hidden layers of the neural network on the basis of the error information.

As the skilled person will appreciate, what is significant about the training stage is not a particular training method or algorithm, but that the method chosen for training is able to modify some characteristic of the machine learning approach/algorithm in order to enable the algorithm to generate an output O' for a given input training image I' which more closely approximates the training label data L for that input (i.e. reduces a measure of error between label information L and output O'). Furthermore, in some implementations the machine learning approach used may be an unsupervised machine learning approach, such as an autoencoder approach or a semi-supervised machine learning approach.

Steps 404 to 407 may collectively be referred to as a training stage, and a plurality of successive training stages may be carried out until the machine learning approach is considered to be fully trained. A determination of the state of training may be based on the change in error (i.e. error between label information L and output O') over successive training stages. For example, iteration through successive training stages may continue until a change in the measure of error with successive iterations effectively reaches zero. In other examples, iteration through successive training stages may continue until the change in the measure of error with successive iterations drops below a predetermined threshold. The condition whereby the change has reduced to a suitably low value may be referred to herein as a training stop condition. The determination of whether a stop condition is reached may be achieved, for example, by differentiating over the output error with respect to training stage in order to quantify the change in error value over training stage. In some embodiments, a predetermined number of training stages is defined, and if the change in error does not reach a stop condition within the given number of stages, a further set of stages is defined and training continues. However, if the stop condition is reached within the predetermined number of training stages, training may in some instances be considered to be complete. The determination of when to stop training the machine learning approach (i.e. cease applying training stages) may alternatively or in addition be based on the results of a validation stage. The validation stage will be recognized from the training stage, and may use a validation dataset, which may be acquired in the same manner as the training dataset (i.e. comprising one or more images of embryos with associated label information) but which does not comprise data used in the training of the machine learning approach. The validation stage may be differentiated from the training stage described above in that following comparison of the output to the label information in comparison step 703, the error is not used to modify the operation of the machine learning approach 701, but is used to check the accuracy of the machine learning output O' relative to the label information L. Hence, in one embodiment, the performance of the partially or fully trained machine learning approach is quantified by incorporating a validation stage at various intervals during training, in which the partially trained machine learning approach is applied to one or more validation images and a level of error is determined on the basis of a comparison between the output of the machine learning approach for each validation image and the label information associated with each validation image. The error may be determined on a pixel-wise basis and summated, for example, over an entire image, or over an entire set of images. At each validation stage, the resulting error value may be compared to some threshold value, and training may continue until the error value as determined during a validation stage, is below the threshold value. In some instances, a validation stage may comprise a part of a training stage, in that the error determined in comparison step 703 is used to check the accuracy of the machine learning output O' relative to the label information L and make a decision about whether to continue training. In some embodiments, a validation stage may be incorporated following a predetermined number of training stages. In other embodiments, a validation stage may be introduced once the training is considered to be complete on the basis of the change in error with successive training stages effectively reaching zero or falling below a predetermined threshold. In other embodiments, where no validation data is present, k-fold cross validation may be performed. Thus the training data may be split into k equally sized parts (portions/splits) and k−1 parts may be used for training and the 1 remaining part may be used for validation. Training may then be repeated multiple times with different parts being selected for validation each time to obtain a mean/average error for the data.

Figure 11:
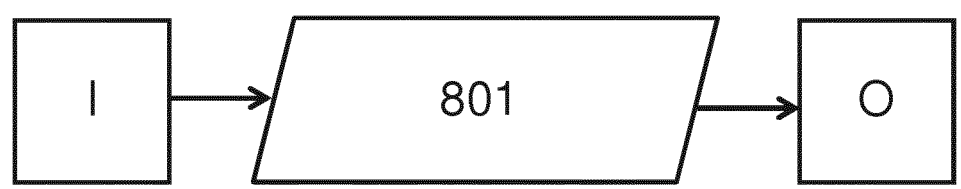
FIG. 11 schematically represents a method for applying a machine learning approach to classify pixels comprising an image of an embryo.
Figure 12:
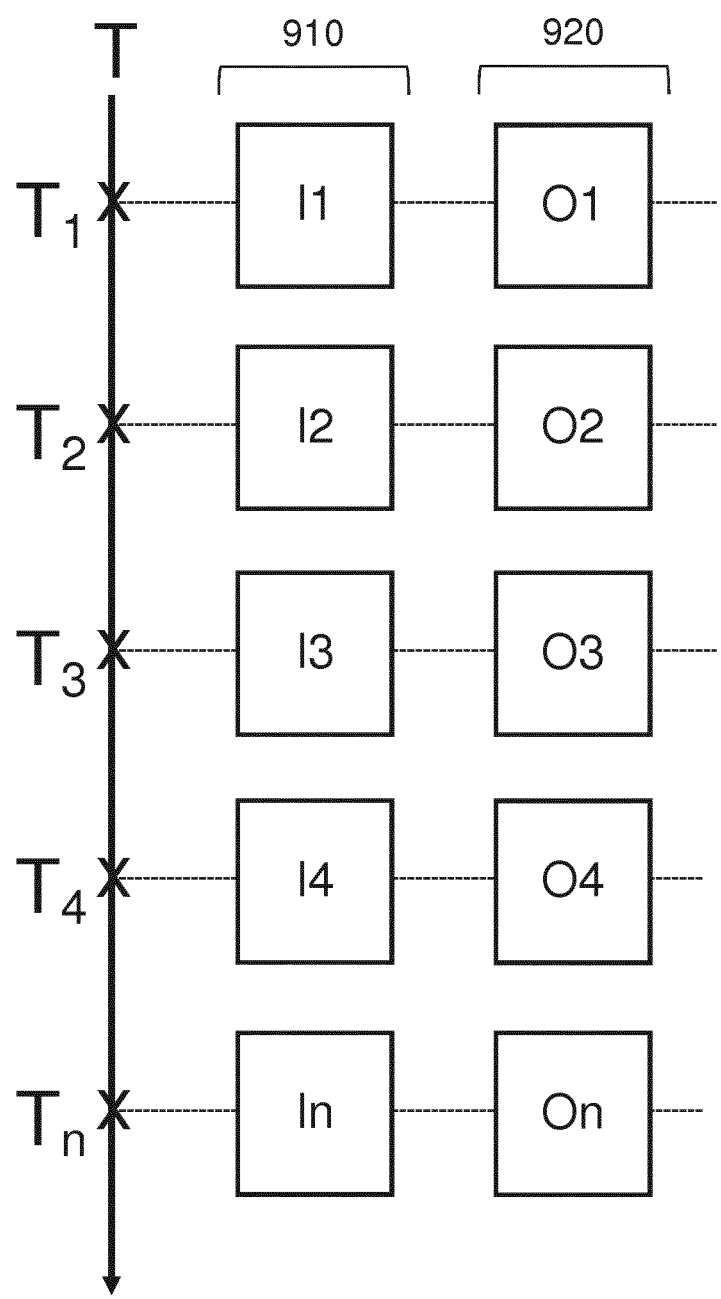
FIG. 12 schematically represents a time series of input images of embryos, with an associated time series of output images in which pixels have been classified by a machine learning approach.

Following training of the machine learning approach, and with reference to the schematic representation shown in FIG. 11, the trained machine learning approach 801 may be applied to an input image I to generate an output O, which may be considered to comprise a segmented version of the input image I. The likelihood value associated with each pixel in the output O may be used to determine a discrete class identity for each pixel. For instance, for a given pixel, if the likelihood value is between 0.5 and 1 the pixel may be assigned to the embryo class, and if the likelihood value is between 0 and 0.5, the pixel may be assigned to the background class. If the likelihood value is exactly 0.5, the pixel may be arbitrarily assigned to either class. Thus what is significant about this stage is that in some examples the output O is converted to a segmented image in which pixel values are classified with respect to the target classes. With reference to the schematic approach shown in FIG. 8, in step 501, an image from a time series of images such as the time series acquired in step S2 of FIG. 4 is applied as an input to the trained machine learning approach. In step 502, the trained machine learning approach is applied to determine an output O on the basis of the input image I. In this way, any number of input images can be processed. FIG. 12 schematically shows a time series of input images 910 and a time series of corresponding output images 920, wherein a given output image On in the sequence 920 is generated from a respective input image In in the sequence 910 via the application of a segmentation approach such as those described above.

A segmented image of an embryo (such as an image On in FIG. 12) may thus be used to determine suitable dimensions and positions for a cropping ROI to be used for cropping the unsegmented input image, such as an image In from sequence 910. Hence, an embryo label field (i.e. set of pixels determined to correspond to embryo features) may be used to determine geometric information useful for defining a suitable cropping ROI in the unsegmented image from which the label field has been determined. For example, an embryo label field may be used to determine information such as an embryo centroid (i.e. a centre of rotation/geometric centre of mass of the set of embryo pixels in an image), and a maximum dimension of the embryo representation in the horizontal and vertical axes. The maximum width of the embryo label field may be termed WE' and the height may be termed HE'. In one embodiment, the size and position of a cropping ROI are selected to define the smallest ROI which entirely encloses a label field corresponding to a representation of an embryo in the image. Thus the dimensions of this label field may be WE'×HE'.

In some embodiments, a cropping ROI is automatically determined for each image whereby the dimensions and position of the cropping ROI are optimised to minimize the ROI size (in terms of total pixel count, and/or dimensions in one or both of the orthogonal image axes) whilst fully enclosing the embryo label field within the boundary of the cropping ROI. In one embodiment, the x coordinates of the TL and BL vertices are set to the x coordinate of the left-most pixel in the embryo label field. Similarly, the x coordinates of the TR and BR vertices are set to the x coordinate of the right-most pixel in the embryo label field. The y coordinates of the TL and TR vertices are set to the y coordinate of the uppermost pixel in the embryo label field. They coordinates of the BL and BR vertices are set to the y coordinate of the lowermost pixel in the embryo label field. The geometric information for the cropping ROI may then be stored for each image, for example, by recording the vertices of the ROI.

As described above with reference to FIG. 6, a single set of cropping ROI dimensions (i.e. W' and H') may be defined which is applied to determine a cropping ROI for each image in a sequence, such as a sequence of images 910 shown schematically in FIG. 12.

Next, a cropping ROI position may be determined for each image. The purpose of this step is to determine where in each image to situate the cropping ROI so as to substantially or fully enclose all the pixels in the embryo label field. For example, an x and y coordinate in each image may be determined at which the centroid of the cropping ROI should be set in order to generate a cropped image. In one instance, a user may manually define a position for the cropping ROI in each image in the sequence, for example, by using an input device to drag a representation of the cropping ROI overlaid over the image, and repositioning it until the embryo appears on visual inspection to be enclosed within the boundary of the cropping ROI. In another embodiment, the location of the cropping ROI, for example an x and y coordinate for locating the cropping ROI centroid, may be determined using an automated approach. For example, coordinates may be computed which represent a centroid of the embryo in the image. This could be achieved using any approach known to the skilled person, including, for example, integrating over the area of the embryo in x and y directions. In one embodiment, the centroid of the cropping ROI is positioned at the embryo centroid determined for each image, and each image cropped using the ROI.

It will be appreciated that image cropping is optional, and in some embodiments a cropping step may be omitted. Furthermore, it will be appreciated that where an image comprises a plurality of frames, the cropping step may generally be applied in the same manner to each of the frames comprising the image, in order to maintain a condition in which all frames of a cropped image share the same dimensions.

In step S3 of FIG. 4, a scaling step is applied to adjust the image size prior to subsequent steps. This can, for example, enable more efficient storage and/or analysis of images. If an image cropping step is used, as described in step S2 above, downscaling may be carried out subsequent to the cropping operation, in order to maintain a higher effective resolution for the embryo(s) in the resulting scaled images. Many approaches to downscaling of images are known in the art, and it will be appreciated that any method or algorithm can be used for downscaling which enables the effective resolution of the images to be reduced. For example, an algorithm implementing bilinear, bicubic or Lanczos interpolation could be used. It will be appreciated when selecting a downscaling approach that it is in some cases desirable to use a method which preserves image feature information (e.g. edges) and does not unduly introduce artifacts (e.g. noise, smoothing). A suitable downscaling method may be selected by applying different downscaling methods to copies of the same image, and comparing image quality features for the different downscaled output images (e.g. using measures of contrast and image sharpness as a basis for comparison). A degree of downscaling (i.e. a scaling factor) may be selected which generates images with a suitable size for subsequent image analysis processes, for example having regard to the computing power available. For example, in some embodiments, the images may be downscaled to reduce their size by a factor of 2 in both dimensions (i.e. x and y axes). In one embodiment, images with an original size of 500×500 pixels are downscaled to produce images with a size of 224×224 pixels. As described elsewhere herein, an image may in some embodiments comprise a plurality of frames/layers. For example, an image may comprise 3 frames, respectively constituting red, green and blue colour channels. In another example, an image may comprise a number of frames representing the embryo at one stage in development, but acquired using different focal planes. For instance, an image might comprise 11 frames, each of which comprises image data acquired at a different focal plane. It will be appreciated that where an image comprises a plurality of frames, a downscaling operation will in most instances be applied to all frames such that each frame comprising a rescaled multi-frame image shares the same dimensions. In some embodiments, a multi-frame image may be rescaled to reduce the number of frames, for example by averaging pixel values across one or more frames to generate a new rescaled image with a smaller number of frames. Images may be downscaled by the same factor in both orthogonal image axes, however in some instances a different scaling factor may be used to scale images in the x and y dimensions. It may be desirable to use a single scaling factor (S) which produces rescaled images whose width and height are proper factors of the width and height of the original image. In other words, if the width and height of the unscaled image are W1 and H1 respectively, and the width and height of the scaled image are W2 and H2 respectively, such that W2=S·W1 and H2=S·W2, it may be desirable to select a scaling factor S such that W1 mod(W2)=0 and H1 mod(H2)=0.

It will be appreciated that an image scaling step is optional, and in some embodiments a scaling step may be omitted.

Figure 13:
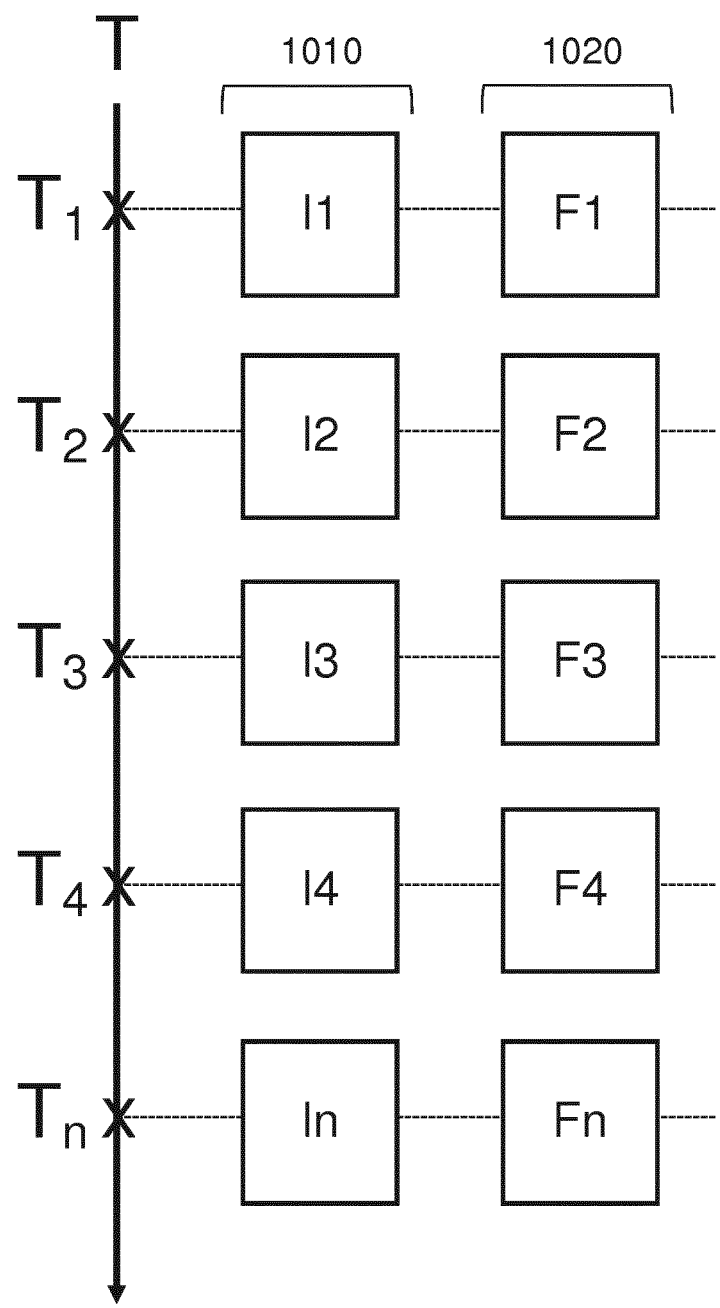
FIG. 13 schematically represents a time series of input images of embryos, with an associated time series of instances of feature information.

In step S4 of FIG. 4, feature information is determined on the basis of images comprising a time series of images such as those acquired in accordance with step S1, and optionally cropped and scaled in accordance with steps S2 and S3. Feature information will be understood to be a general description for information relating to features within an image, such as an image of an embryo. Thus, as shown schematically in FIG. 13, a time series of images 1010 may be associated with a time series of instances of feature information 1020, wherein each image I in time series 1010, acquired at time T, is associated with a corresponding instance of feature information F in series 1020. In one embodiment, the feature information F for an image I comprises the image I itself (for example, a 2D array of pixel intensity values, or an image comprising a plurality of frames/layers, each of which comprises a 2D array of pixel intensity values). In this instance, feature extraction step S4 in FIG. 4 comprises passing an image I to the next step S5, wherein it may be referred to as feature information F. In other instances, feature information F for an image I comprises a higher-level description relating to features in the image I, for example, a vector of values wherein the values are related to characteristics of features in the image I. What is in some cases significant about the feature determination step S4 is that the feature information F determined for an image I may comprise a means of representing the image I in a simpler and/or less memory-intensive form, in which information about features in the image I is nonetheless conserved. For instance, an image I of 224×224 pixels (i.e. ~5×10$^4$ values) may be used to determine feature information F comprising a 512-dimensional vector, wherein the values in the vector are related to characteristics of features in the image I. These features may in some instances be considered as features at a higher- or abstracted-level from the pixel level.

In one embodiment, feature information F comprises information determined from a histogram of pixel intensity associated with an image I (and in particular for the pixels classified as corresponding to the embryo in implementations in which a segmentation step has been applied). In one example, 256 evenly-spaced bins are used to describe an intensity range encompassing the intensity distribution of the pixels/subset of pixels classified as representing the embryo in the image I, and a value is determined for each bin indicating a frequency of pixels whose intensity values fall into the intensity range associated with said bin. Feature information F for the image I in this instance may comprise a 256-dimensional vector, with one dimension being associated with each bin, wherein the value assigned to each dimension indicates the frequency of pixels for the associated bin.

In another embodiment, hand-crafted image descriptors are used to generate feature information F. As the skilled person will readily understand, there are a large number of hand-crafted descriptors which may be used to describe features in an image. In one embodiment, the feature information may be based on descriptors derived using a scale invariant feature transform such as a keypoint or patch descriptor (e.g. a descriptor based on a Harris corner detector).

In another embodiment, feature information F is determined for an image I using a machine learning approach. A machine learning approach to determining feature information may comprise using a decision tree, a graphical model, a fast-forest algorithm, a support vector machine, a clustering method or an artificial neural network approach. The approach produces feature information F which may be considered an abstracted representation of features in an input image I.

One embodiment of a machine learning approach comprises a feature quantification step, a feature clustering step, and an image classification step. This may be referred to as a 'tag-of-words' or a 'codebook' approach. One or more images, such as a set of images 910, may be described using a plurality of keypoint/patch descriptors, wherein each descriptor comprises a vector containing feature information associated with a subregion of an image. For example, a keypoint/patch descriptor may be a 128-dimensional vector. A plurality of keypoint/patch descriptors is determined for each of the one or more images. The set of keypoint/patch descriptors determined from the one or more images may then be sorted into clusters, for example, using a K-means clustering approach. In one example, the keypoint/patch descriptors are 128-dimensional vectors, and K-means clustering is used to determine n clusters defined in 128-dimensional space. A centroid is computed for each of the n clusters (which may represent an average computed from the set of vectors comprising the cluster), and the vector representing each centroid is then referred to as a codeword for the associated cluster. The set of n codewords corresponding to the n clusters is referred to as a codebook. Each codeword in the codebook may be referred to via a codeword ID. In this manner, a codebook may be determined from a set of keypoint/patch descriptors derived from a large number of images, for example, a set 1010 comprising a time series of images I1 to In, such as shown schematically in FIG. 13, and wherein each image contains a representation of one or more embryos.

Once a codebook has been derived, based on keypoint/patch descriptors from a plurality of images, feature information F for a single image I may be determined by deriving a number m of keypoint/patch descriptors for the image. The m descriptors may be sorted to determine for each descriptor the closest of the n codewords in the codebook (i.e. the codeword vector most closely approximating the descriptor). In this way, a 2×n array may be determined, in which the first value of each row is a codeword ID and the second value is the frequency of the m keypoint/patch descriptors which are determined to be closest to that codeword. It will be understood that the result of this process represents in effect a histogram of frequency for the codebook. The array of codeword frequencies for an image may be called a bag-of-words or a bag-of-features for the image. A bag-of-words or bag-of-features for an image, determined in this manner, may be used as feature information for the image.

Figure 14:
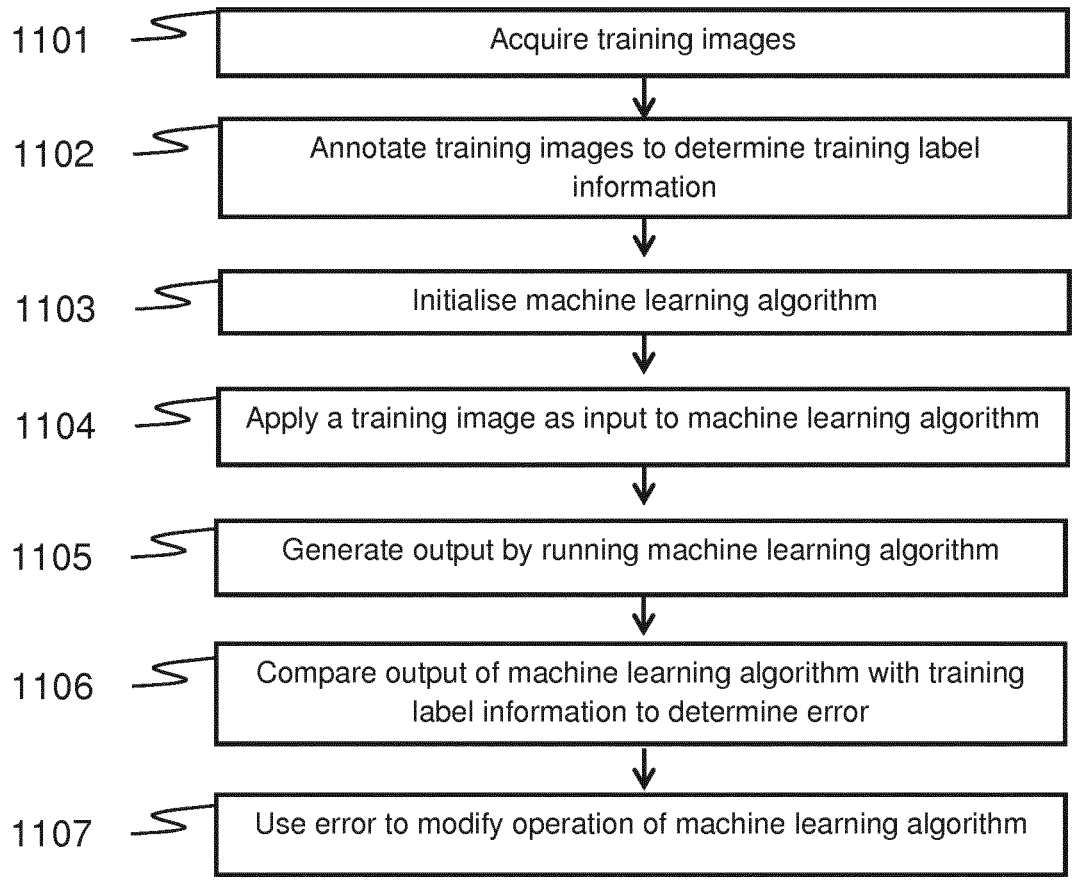
FIG. 14 schematically represents a method for configuring a machine learning approach for use in generating feature information from an image of an embryo.
Figure 15:
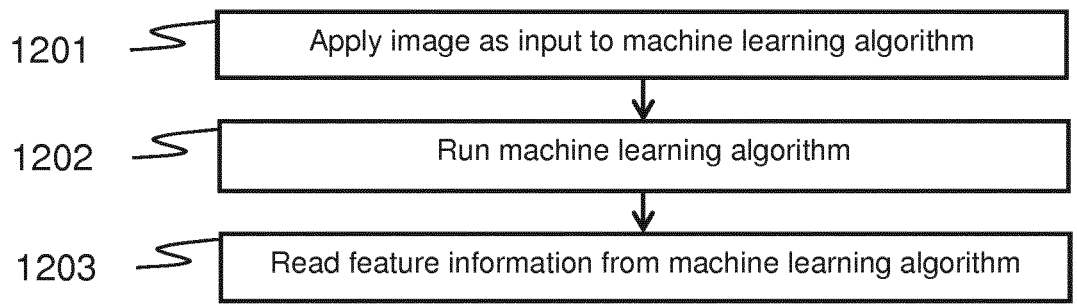
FIG. 15 schematically represents a method for generating feature information from an image of an embryo using a machine learning approach.

In other embodiments, feature information may be derived using other machine learning approaches, for example, neural network approaches. FIGS. 14 and 15, which are in some respects similar and will be understood from FIGS. 7 and 8, schematically show approaches to determining feature information from images using a machine learning approach.

Figure 16:
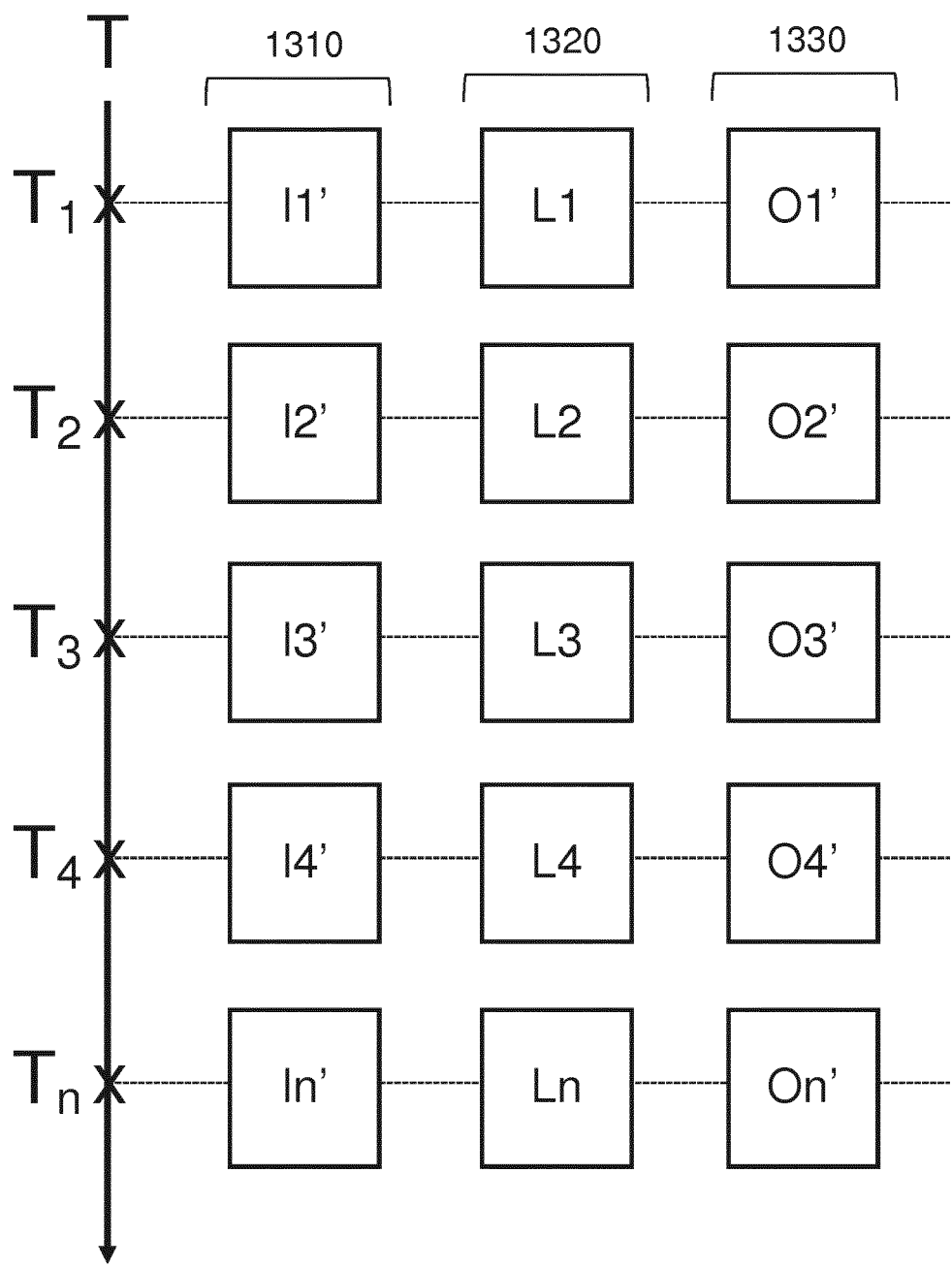
FIG. 16 schematically represents a time series of training images of embryos, with associated time series of training label information and machine learning outputs.

Thus in step 1101 of FIG. 14, a set of training images is acquired. The training images may comprise a series of images acquired using approaches described in relation to step S1. The training images may be cropped and scaled according to the approaches described in relation to steps S2 and S3. In FIG. 16, a set 1310 of n training images (I1' to In') is shown schematically. Dashed lines indicate the association of each training image to a time of acquisition t, such that, for example, training image I1' is associated with acquisition time T1.

In step 1102 training images, such as images I' in set 1310, are annotated to associate each training image with an instance of training label information, which is information about one or more classes associated with the image. In FIG. 16, a set 1320 of n instances of training label information (L1 to Ln) is shown schematically. In FIG. 16, dashed lines indicate the association of each instance of training label information to a training image I' and an acquisition time T, such that, for example, training label information L2 is associated with training image I2' acquired at time T2. The combination of a plurality of training images 1310 and associated training label information 1320 may be termed a training dataset. The training label information may comprise information about one or more classes which represent higher-level information that can be used to characterize an embryo. An instance of higher level information may comprise, for example, a description of an embryo developmental event, for instance, a description of a morphokinetic parameter, cycle, state, stage or event. For example, the training images in set 1310 may contain representations of embryos, and an instance of training label information L associated with a given training image I' may comprise information about one or more transition probabilities for an embryo represented in the training image. In this embodiment, the training label information may comprise a plurality of classes indicative of different transition events, such as a cleavage from a 1-blastomere embryo to a 2-blastomere embryo, such as a cleavage from a 2-blastomere embryo to a 3-blastomere embryo, and so on, i.e. cleavage from an n-blastomere embryo to an n+1-blastomere embryo.

Assigned to each class is a likelihood value indicating a probability that the embryo represented in the training image is associated with the transition event represented by said class.

In another embodiment, the training label information L may comprise a single value indicating a general transition probability, wherein the value indicates the likelihood that embryo represented in an associated training image I' is associated with any transition event from a plurality of possible transition events. In one example, the value may be assigned a value of '1' if the embryo in the training image I' is highly associated with a transition event (for instance, features indicative of an intra-cell-division state are observable in the training image), and the value may be assigned a value of '0' if the embryo represented in the training image is not associated with a transition event (i.e. the embryo is not considered to be in a state of transition at time T).

It will be appreciated that for some implementations what is significant about label information L is that it comprises information about one or more high-level developmental features which are determined to be useful for distinguishing between different embryos and/or the same embryo at different stages of development. Each of the classes comprising the label information may relate to any parameter associated with embryo development, such as an embryo cycle, stage or event. Hence classes can be associated with cell cycles, cell division events, and other events, such as start of compaction (SC), fading of pronuclei (tPNf), morula (M), initial differentiation of trophectoderm (IDT), start of blastulation (SB), blastocyst (B), initial differentiation of inner cell mass (IDICM), onset of expansion of the blastocyst (EB), hatching blastocyst (HB), fully hatched blastocyst (FH), appearance of first polar body, appearance of second polar body, appearance of first pronuclei, appearance of second pronuclei, time of pronuclei alignment, start of blastocyst collapse, and start of blastocyst re-expansion.

The association of training label information L with a training image I' is referred to herein as annotation. Annotation may be carried out by a user, for example, an embryologist, using a general purpose computer such as computer 110, having a graphical user interface such as display 1180 and one or more input devices such as devices 1190 and 1191. In one embodiment, an image is acquired, for example using imaging apparatus 120, or by reading stored data from HDD 117, and displayed on display 1180. For example, the image may be a training image I' from a set of images 1310 as shown schematically in FIG. 16. The user determines one or more values relating to one or more morphokinetic parameters associated with the embryo. These values are each assigned to a respective class for the morphokinetic parameter. For example, a morphokinetic parameter determined during annotation may be a general transition probability, which is a likelihood value indicating that the embryo displayed to the user is in a state of transition from any one stage/cycle/state to another stage/cycle/state. The determination of the morphokinetic parameter for a given image may involve the user reviewing images prior to and subsequent to the position of said image in the time series. Once a likelihood value for the general transition probability has been determined for the training image I', this information may be defined as training label information L for the training image, and may be stored in a suitable data structure, for example a vector or array of numeric values. For example, the training label information L for each image may comprise a 1-dimensional vector containing a single value which ranges from '1', which indicates the highest transition probability, to '0', which indicates the lowest transition probability.

In another embodiment, training label information comprises an n-dimensional vector, in which discrete likelihood values are defined for each of n morphokinetic descriptors. For example, the training label information L for an image I' of an embryo may comprise an 8-dimensional vector, where each of the 8 values in the vector represents the likelihood of the embryo being associated with one of 8 respective transition events (e.g. a cleavage event between two cell cycles). In this instance, annotation of a training image comprises assigning likelihood values to each of the transition events, for example, using the approach described above. In some instances, the value for the event deemed to be most strongly associated with the training image is set to '1', and the values associated with all other events are all set to '0'. This representation may be referred to as a 'one-hot' vector.

What is in some cases significant about the annotation of training images is that the training label information provides information about a target state for a classification. A classification in this context will be understood as meaning the association of an input training image to one or more classes, for example, by assigning likelihoods that the image should be considered as being associated with each of the classes. Thus the skilled person will appreciate that the training data may comprise any images which contain a representation of one or more embryos, and training label data which provide information (for example class likelihood information) about the images which is useful for differentiating between different embryo stages. Such information can be acquired using any approaches in the prior art that are suitable for image acquisition and annotation.

In other embodiments, which may be termed unsupervised approaches, training label information may not comprise class information generated by annotation. In one embodiment the label information for a training image used to train a machine learning approach comprises a copy of the training image itself. This form of machine learning approach, where the input is also used as training label information, may be referred to as an autoencoder approach.

In one embodiment of an autoencoder approach, the machine learning approach comprises a neural network configured to take an image as an input, and generate an output image with the same dimensions as the input. Thus an input image may be input to an input layer of the neural network, and an output image may be output from an output layer. The neural network may have a series of intervening layers which may be referred to as hidden layers. The hidden layers may comprise operators including activation functions, summation functions, pooling functions, convolutional functions, de-convolutional functions, weighting functions and biasing functions. Each layer may comprise a plurality of nodes, each of which may be associated with one or more operators. The output from a node in a layer n may be passed as an input to one or more nodes in a layer n+1. Hence, the layers may be interconnected, with outputs from a layer being passed as inputs to a subsequent layer.

In one embodiment, a neural network is a so-called convolutional neural network (CNN) configured to comprise a series of convolutional and pooling layers (i.e. layers comprising convolutional and pooling filters) which produce a progressively more compact and abstract representation of the input image (for instance, in terms of a discrete number of values encoding the data), followed by a series of deconvolutional layers, which deconvolve the compact representation such that an output with the same dimensions as the original input image is output from the output layer. Training of the neural network thus described may proceed by using the input image itself as training label information, such that the target of the training stage is to adjust the network so that the output approximates the input (for example, having closely matching intensity values for corresponding pixels or groups of pixels as compared between the input and output images).

In step 1103 the machine learning approach is initialised. In some embodiments the machine learning approach comprises a support vector machine. In some embodiments the machine learning approach comprises a graphical model such as a Markov random field model or a Bayesian model. In some embodiments the machine learning approach comprises using feature quantification combined with a random-forest classifier. In some embodiments the machine learning approach comprises a clustering approach, such as K-means clustering. In some embodiments the machine learning approach comprises an artificial neural network. The machine learning approach may be configured to run on CPU 111 or GPU 116 of a general purpose computer such as computer 110 shown in FIG. 110. The skilled person will recognise that the machine learning approach may be configured to run within a framework known in the art, such as those provided by TensorFlow, Theano, Torch, Caffe, or the Waikato Environment for Knowledge Analysis. In one embodiment, the machine learning approach is configured to run within the MobileNet architecture. Alternatively the approach may be programmed using a suitable programming language, for example, Python or C++.

Also in step 1103, an initial configuration of operators, functions, weights, biases, and other parameters relating to the operation of the machine learning approach may be selected. For example, in one embodiment the machine learning approach comprises an artificial neural network, and the configuration of the approach may comprise selecting a number of layers, selecting a number of nodes per layer, selecting and configuring activation functions, selecting and configuring weighting coefficients (or 'weights') selecting and configuring biasing coefficients (or 'biases'), selecting and configuring convolution/deconvolution operators, selecting and configuring pooling operators, selecting and configuring sub-sampling operators, selecting and configuring rectifying operators, and selecting and configuring one or more classification layers. Suitable operators and parameters values may be selected, for example, based on experimentation or modelling.

The configuration of the machine learning approach in step 1003 will be conducted such that the output of the machine learning approach is related to the objective/task of the machine learning approach. In other words, the output of the machine learning approach may be in a format which enables it to be compared to training label information associated with a training input. For example, if training label information is an n-dimensional vector of values ranging from '0' to '1', the machine learning approach may be configured to generate an output for each input image which is an n-dimensional vector of values ranging from '0' to '1'.

Steps 1104, 1105, 1106 and 1107 comprise a training stage, which may be iterated over a plurality of times in order to train the machine learning approach to carry out the task to an appropriate level of performance. In some embodiments, the objective of the training stage is to minimize the error between the label information associated with an input training image, and the output generated by applying the machine learning approach to the input training image. The error may be minimized with respect to a plurality of training stages applied to a single input training image, or a plurality of training stages applied to a plurality of input training images.

Figure 17:
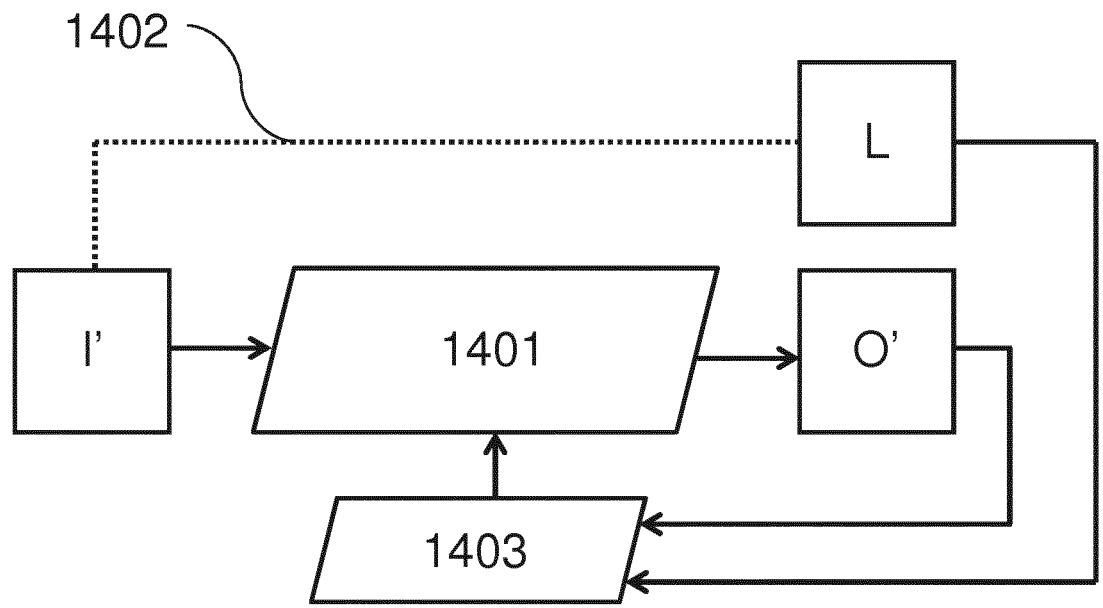
FIG. 17 schematically represents a method for training a machine learning approach to determine feature information on the basis of an input image of an embryo.

Thus in step 1104, a training image I' is selected from set of training images such as those acquired in step 401 of FIG. 7, and is applied as an input to the initialised machine learning approach. For example, in one embodiment the machine learning approach is a convolutional neural network (CNN), and the training image is supplied as an input to the input layer of the CNN. FIG. 17 schematically shows a training image I' being applied as an input to machine learning approach 1401.

In step 1105, an output O' is generated by applying the machine learning approach to the input training image I'. FIG. 17 schematically shows an output O' generated by machine learning approach 1401 on the basis of input training image I'. In one embodiment the approach 1401 comprises a convolutional neural network (CNN), and the output O' comprises a vector of likelihood values each of which is associated with a target class. For example, a likelihood value for a class may be a numeric value between '0' and '1', where the value is related to a probability that the input training image I' contains a representation of an embryo that is associated with a morphokinetic stage, event, or cycle represented by said class. The particular choice of data format for the output is not particularly significant. Rather what is significant about the output O' in some cases is that it provides information on the likelihood of a representation of an embryo in the input training image I' being associated with each of one or more target classes.

In step 1106, the output O' is compared to label information L associated with the input training image. The objective of this comparison is to determine how closely the output O' of the machine learning approach matches the label information L. In one embodiment, this comparison is used to determine an instance of error information, which is information quantifying the degree of difference between the output and the label information. This may be achieved in any manner known to the skilled person, for example, through use of an appropriate error function such as a cross-correlation function. FIG. 17 schematically shows training label information L (associated with input training image I' as denoted by a dashed line 1402) and output O' from machine learning approach 1401 being provided as inputs to a comparison step 1403.

In step 1107, the error information determined in step 1106 is used to modify the operation of the machine learning approach 1401. FIG. 17 schematically shows the output of a comparison 1403 between training label information L and output O' being used as an input to modify the machine learning approach 1401. The modification is carried out such that re-applying steps 1104, 1105 and 1106 using the same training image I' and the modified machine learning approach 1401 will result in a lower error between the output O' and the label information L, as determined by comparison 1403. For example, the machine learning approach 1401 may comprise a plurality of operators and a plurality of parameters (for example, weighting coefficients), and any combination of these may be adjusted during step 1107. In one embodiment, the machine learning approach comprises one or more decision trees, and parameters associated with one or more decision trees may be adjusted during step 1107. In another embodiment, the machine learning approach comprises a convolutional neural network, and a gradient descent approach is used to update weights associated with the hidden layers of the neural network on the basis of error information determined by comparison 1403.

As will be appreciated, what is significant in some cases about the training stage is not a particular training method or algorithm, but that the method chosen for training is able to modify some characteristic of the neural network in order to enable the network to generate an output for a given input image which more closely approximates the training label data for that input (i.e. reduces a measure of error between label information L and output O'). Furthermore, in some implementations the machine learning approach used may be an unsupervised machine learning approach, such as an autoencoder approach or a semi-supervised machine learning approach.

Steps 1104 to 1107 may collectively be referred to as a training stage, and a plurality of successive training stages may be carried out until the machine learning approach is considered to be fully trained. A determination of the state of training may be based on the change in error (i.e. error between label information L and output O') over successive training stages. For example, iteration through successive training stages may continue until a change in the measure of error with successive iterations effectively reaches zero. In other examples, iteration through successive training stages may continue until the change in the measure of error with successive iterations drops below a predetermined threshold. The condition whereby the change has reduced to a suitably low value may be referred to herein as a training stop condition. The determination of whether a stop condition is reached may be achieved, for example, by differentiating over the output error with respect to training stage number in order to quantify the change in error value over training stage. In some embodiments, a predetermined number of training stages is defined, and if the change in error does not reach a stop condition within the given number of stages, a further set of stages is defined and training continues. However, if the stop condition is reached within the predetermined number of training stages, training may in some instances be considered to be complete. Determination of the state of the training (and a determination of when to cease applying training stages to modify the machine learning approach) may alternatively or in addition be determined by one or more validation stages. The validation stage will be recognized from the training stage, and may use a validation dataset, which may be acquired in the same manner as the training dataset (i.e. comprising one or more images of embryos with associated label information) but which does not comprise data used in the training of the machine learning approach. The validation stage may be differentiated from the training stage described above in that following comparison of the output to the label information in comparison step 703, the error is not used to modify the operation of the machine learning approach 701, but is used to check the accuracy of the machine learning output O' relative to the label information L. Hence, in one embodiment, the performance of the partially or fully trained machine learning approach is quantified by incorporating a validation stage at various intervals during training, in which the partially trained machine learning approach is applied to one or more validation images and a level of error is determined on the basis of a comparison between the output of the machine learning approach for each validation image and the label information associated with each validation image. A determination of the state of training of the machine learning approach may be made based on a level of error of a single input validation image, or be based on an average over levels of error for a plurality of input validation images. At each validation stage, the resulting error value may be compared to some threshold value, and training may continue until the error value as determined during a validation stage, is below the threshold value. In some instances, a validation stage may comprise a part of a training stage, in that the error determined in comparison step 703 is used to check the accuracy of the machine learning output O' relative to the label information L and make a decision about whether to continue training. In some embodiments, a validation stage may be incorporated following a predetermined number of training stages. In other embodiments, a validation stage may be introduced once the training is considered to be complete on the basis of the change in error with successive training stages effectively reaching zero or falling below a predetermined threshold.

Figure 18:
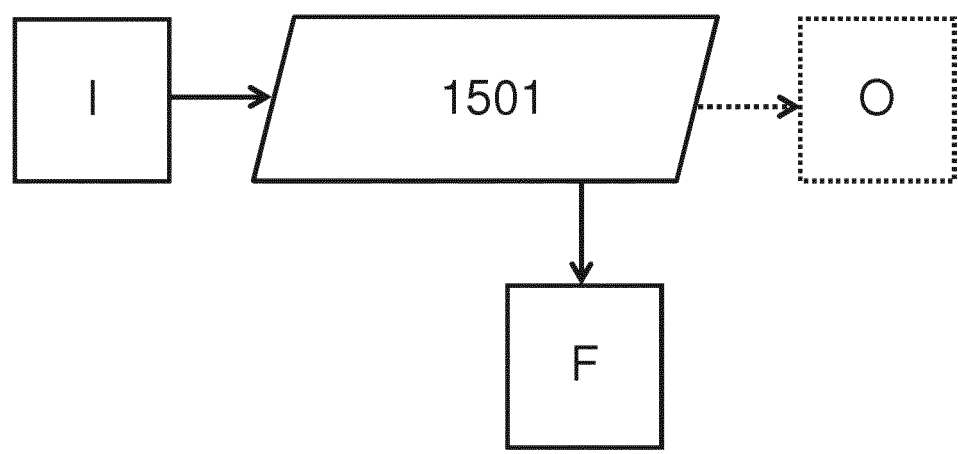
FIG. 18 schematically represents a method for applying a machine learning approach to determine feature information on the basis of an input image of an embryo.

Once the machine learning approach 1401 is trained, feature information may be extracted by applying the trained machine learning approach to one or more input images. What can be considered in some cases significant about this approach is that feature information F comprises one or more values (for example, a vector or array of values) sampled from a stage of information processing in the machine learning approach that is prior to the stage at which output O' is generated. For example, FIG. 18, which is in some respects similar to and will be understood from FIG. 17, schematically shows a feature information determination approach in which a trained machine learning approach (algorithm) 1501 takes an image I as an input (wherein the image may comprise only the pixels classified as embryo if segmentation/masking has been applied, and may have been cropped and or scaled if this has been applied) and outputs feature information F without being required to complete the full set of processing operations required to generate an output O'.

The machine learning approach 1501 may comprise an algorithm in which information is passed among and modified by a hierarchy of operators. In one embodiment the machine learning approach 1501 is an artificial neural network (for example, a convolutional neural network), comprising a plurality of interconnected layers between which information is passed. The configuration of layers may comprise an input layer (where an image I' is input to the network, as shown in FIG. 17), and an output layer (where an output O' is output from the network, as shown in FIG. 17), and one or more intervening 'hidden layers' between which information is passed. Each of the hidden layers may comprise various operators and associated parameters (i.e. variables or coefficients) which modify information as it passes through the layers. Thus in one embodiment, feature information F comprises information extracted from one or more hidden layers of the neural network during information processing. In other words, feature information in this instance may be comprised of a plurality of numeric values acquired by reading outputs of a plurality of operators at one or more intermediate stages in the processing path between the input layer and the output layer. Thus, in one embodiment, feature information for a given input image is generated by reading numeric values associated with operations at a hidden layer in the neural network that is situated k layers prior to the output layer. In some instances, one or more numeric values may be read from the output of a node, neuron or unit in one or more hidden layers. One or more numeric values may be read from a vector, an array, a tensor, or other data structure used to store intermediate information associated with processing operations between the input and output layers. In one embodiment, feature information is output from a hidden layer having 512 nodes. The output value of each of the nodes is read, and the values stored, for example in RAM 113, ROM 112, or HDD 117, using any appropriate data structure. In one embodiment, the output values of the nodes in the hidden layer are placed into a 512-dimensional vector.

As the skilled person will appreciate, feature information may be produced using any combination of values read from outputs of nodes in different hidden layers of a neural network. In one embodiment, the feature information comprises output values sampled from a subset of nodes at a single hidden layer of the network. In another embodiment, the feature information comprises output values sampled from across a plurality of hidden layers of the network.

What is in some cases significant about this approach is that feature information can be generated from an input image using a fully- or partially-trained neural network, wherein the feature information is not determined from the numeric values output at the output layer of the neural network. Thus, with reference to the schematic shown in FIG. 15, in step 1201, an image from a series of images such as the time series acquired in step S2 of FIG. 4 is applied as an input to the trained machine learning approach. In step 1202, the trained machine learning approach is fully or partially operated to process the input image. In step 1203, feature information F is read from the machine learning approach. As the skilled person will appreciate, though an image processed in this way will often be sampled from a time lapse sequence, this is not essential to the feature information determination process.

Figure 19:
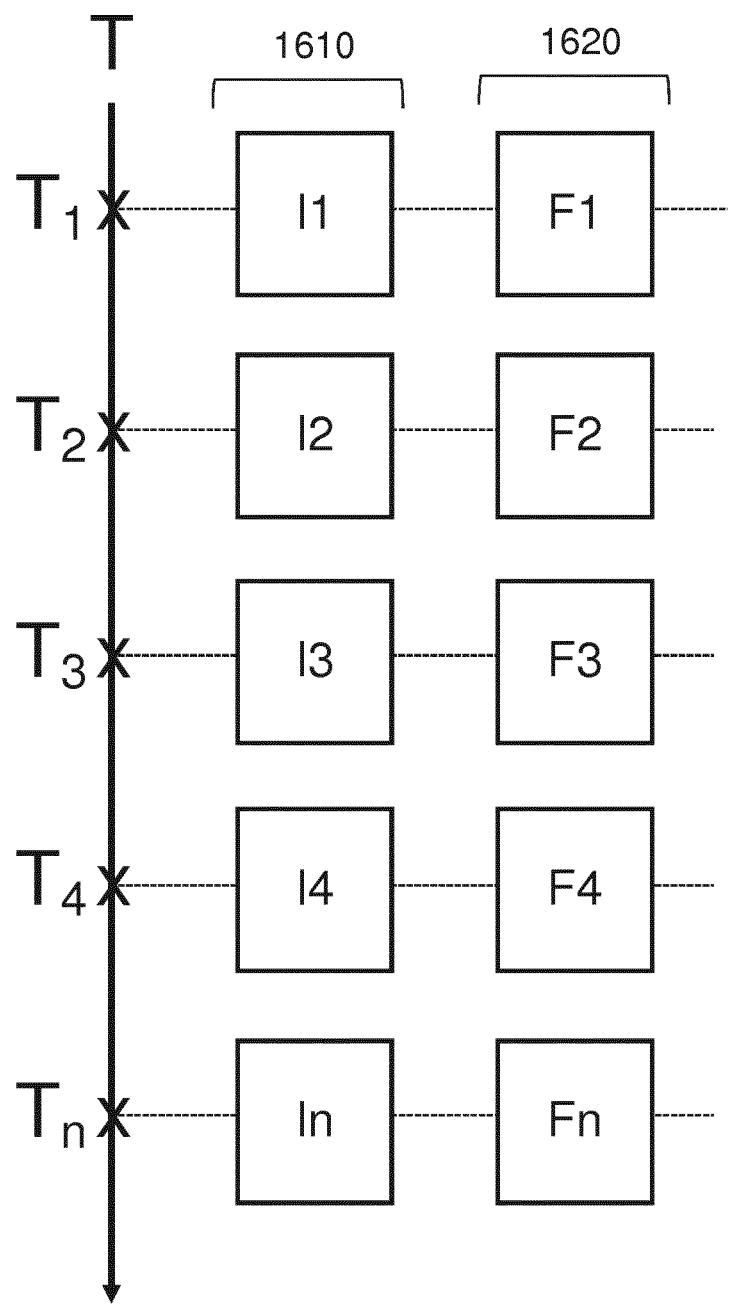
FIG. 19 schematically represents a time series of input images of embryos, with an associated time series of feature information.

In this manner, a sequence of n images can be used to generate a sequence of n feature descriptions (feature information vectors), by processing each image in the sequence using the machine learning approach and thus determining corresponding instance feature information. For example, a time lapse sequence of images of embryo can be used to generate a corresponding time lapse sequence of instances of feature information. For example, in one embodiment, a time lapse sequence of instances of feature information comprising n 512-dimension feature vectors is determined from a sequence of n input images of embryos using a convolutional neural network configured as described herein. In FIG. 19, a set 1620 of n instances of feature information (F1 to Fn) is shown schematically. In FIG. 19, dashed lines indicate the association of each instance of feature information to an input image I and an acquisition time T, such that, for example, feature information F2 is associated with image F2 acquired at time T2, having been determined on the basis of image F2 using a machine learning approach as described herein.

In step S6 of FIG. 4, information is determined relating to estimates of morphokinetic stages, cycles, and/or states, on the basis of feature information determined in step S5. The term morphokinetic event may be used interchangeably with the terms embryonic development event and embryo developmental event, and will be understood as referring to a temporal change in one or more developmental features of an embryo. For instance, a morphokinetic event may be a cleavage event between cell cycles, the start of compaction (SC), the fading of pronuclei (tPNf), the formation of morula (M), the initial differentiation of trophectoderm (IDT), the start of blastulation (SB), the formation of a blastocyst (B), the initial differentiation of inner cell mass (IDICM), the onset of expansion of a blastocyst (EB), the hatching of a blastocyst (HB), the fully hatched blastocyst (FH), appearance of first polar body, appearance of second polar body, appearance of first pronuclei, appearance of second pronuclei, time of pronuclei alignment, start of blastocyst collapse, or start of blastocyst re-expansion. Thus, the skilled person will understand that a morphokinetic event may refer to any change characteristic of the development of an embryo. Estimated times at which morphokinetic events are determined to occur may be referred to as 'event times'. One or more event times may be estimable for a given morphokinetic event, and may comprise an estimated time at which a change in state, appearance, cycle, stage, or other dynamic characteristic of the embryo is determined to have occurred.

The skilled person will appreciate that an event time may be defined with respect to various frames of reference. For example, FIG. 19 schematically shows a time series of images 1610, wherein each successive image I has been acquired at a time T. Thus, for example, the time series begins at time T1 with the acquisition of image I1, and continues through to time Tn with the acquisition of image In. Images such as those comprising the series 1610 may be acquired using approach outlined with respect to step S1 of FIG. 4. With respect to the time series 1610, an 'event time' can be quantified with respect to an image number in the sequence, or with respect to the timeline, or with respect to another suitable reference frame.

In one embodiment, a series of images 1610 comprises 100 images acquired with an inter-acquisition spacing (i.e. Tn-Tn−1) of 15 minutes, wherein the initial image is acquired at time T1, which corresponds in this instance to 12.00 GMT (an arbitrarily chosen time for the sake of example), which in this example is also taken to be the time of Intra-Cytoplasmic Sperm Injection (i.e. fertilisation). Using an appropriate approach (for instance, a machine learning approach) a morphokinetic event is determined to be most closely associated with a given image or sub-set of images. In one example, a cell cleavage event is determined, which on the basis of characteristics of the set of images 1610 is considered to be best represented by certain features of the embryo as represented in the 25th image of the sequence. For example, features associated with the cleavage event may be represented in the $24^{th}$ $25^{th}$ and 26th images of the sequence, but on the basis of this example approach of the kind outlined in this application, the 25th image, as the middle image, is determined to be most strongly associated with the cleavage event. Alternatively, features related to the event itself may not be represented in any of the images, but the 25th and 26th images may represent the first and second images respectively of a pair of images which show the pre- and post-event state. Thus, in one embodiment, the time of acquisition of the 25th image (i.e. T25) may be considered to be the time which most closely corresponds to the cleavage event. Thus an event time for the cleavage event may be expressed with reference to the image position in the sequence, for example, 'image 25'. Alternatively a duration elapsed between the beginning of sequence acquisition and the 25th image may be computed (i.e. T25−T1), which in this instance would be 360 minutes (i.e. 24 intervals of 15 minutes). Alternatively the time may be expressed in terms of the absolute time at which the $25^{th}$ image was acquired, for example, 18:00 GMT.

The skilled person will appreciate that an event time determined from features in a time series of images may be determined using an interpolation approach. For example, if it is determined that an image In acquired at time Tn represents an embryo in an early stage of a certain morphokinetic event, and image In+1 acquired at time Tn+1 represents an embryo in a late stage of the morphokinetic event, a suitable determination of the morphokinetic event time may be determined to lie between the acquisition times Tn and Tn+1. Thus, determination of an event time may be carried out on the basis of interpolation between times Tn and Tn+1.

What is in some cases significant about this step is that morphokinetic event times are determined based on one or more instances of feature information from a time sequence of feature information associated with (i.e. determined on the basis of) a time sequence of images of embryos. The feature information may be derived from images using approaches described herein in relation to steps S1 to S5 of FIG. 4. In FIG. 19, a set 1620 of n instances of feature information (F1 to Fn) is shown schematically. In FIG. 19, dashed lines indicate the association of each instance of feature information F to an image I and an acquisition time T, such that, for example, feature information F2 is associated with image I2 acquired at time T2. As described above, in some instances feature information Fn associated with image In comprises image information In. Thus in some embodiments, feature information series 1620 may be considered to comprise image series 1610.

According to certain embodiments, a sequence of instances of feature information such as sequence 1620 is used as an input to a morphokinetic parameter estimation process, the output of which is an instance of output information O for each instance of input feature information F, and wherein output information O comprises information relating to one or more morphokinetic parameters, being parameters relating to embryo development events such as morphokinetic events, stages or cycles. The morphokinetic parameter estimation process may comprise any approach in which one or more instances of feature information F can be supplied as an input, and output information O relating to one or more morphokinetic parameters is generated as an output. Output information O may herein be referred to as morphokinetic event information.

Figure 20:
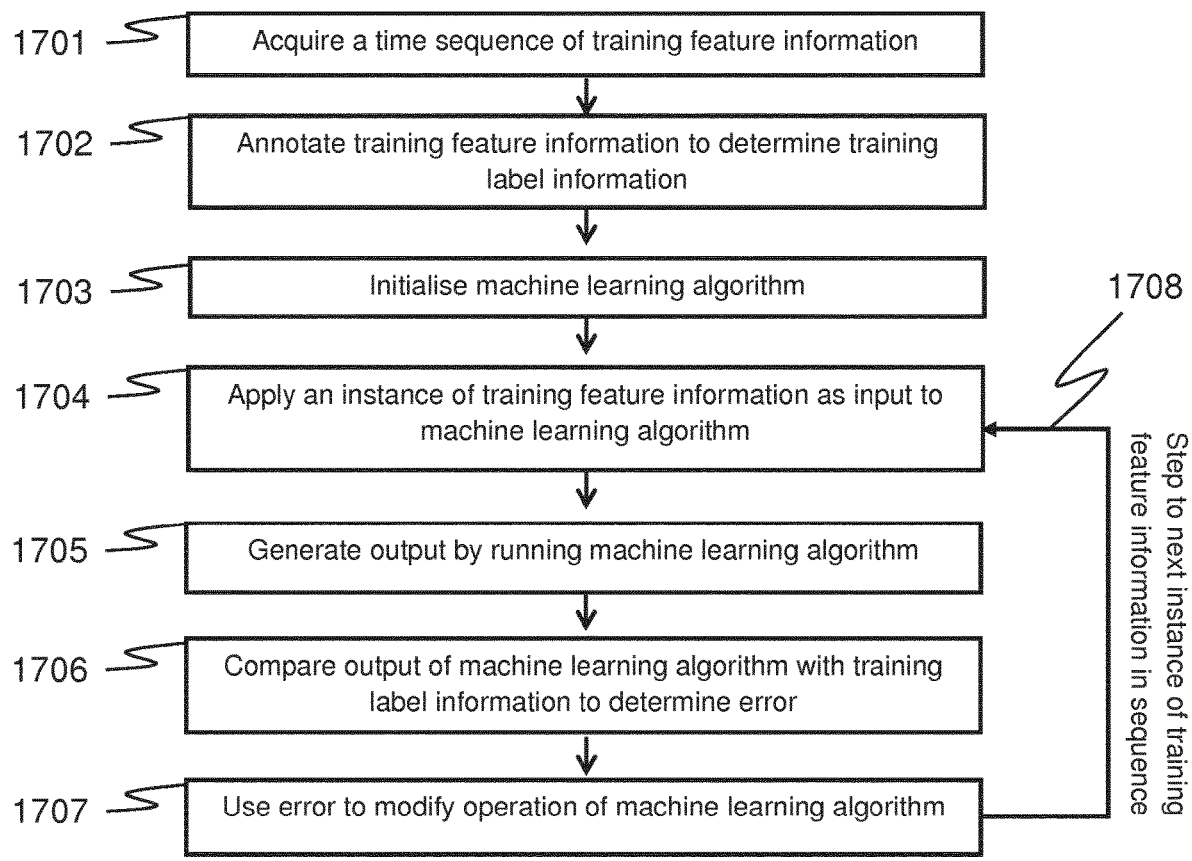
FIG. 20 schematically represents a method for configuring a machine learning approach for use in determining morphokinetic event information on the basis of a time series of feature information.
Figure 21:
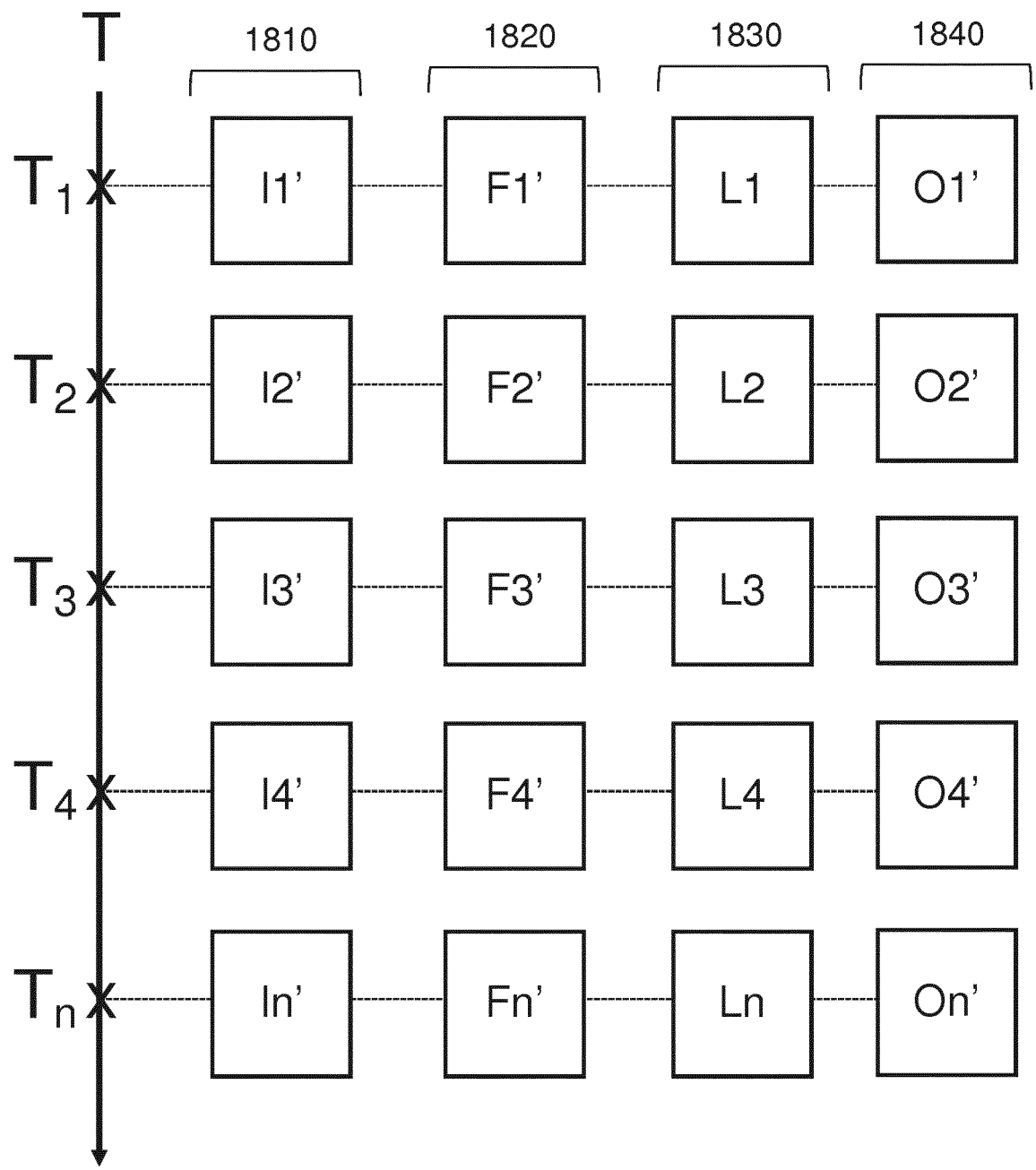
FIG. 21 schematically represents a time series of training images of embryos, with associated time series of training feature information, label information, and machine learning outputs.

Thus in step 1701 of FIG. 20, a set of instances of training feature information is acquired. The training feature information may comprise a series of instances of feature information acquired using approaches described herein in relation to steps S1 to S5 of FIG. 4. In FIG. 21, a set 1820 of n instances of training feature information (F1' to Fn') is shown schematically. Dashed lines indicate the association of each instance of training feature information F' to a time of acquisition T, such that, for example, training feature information F1' is associated with image I1' acquired at time T1. In one embodiment, the set of training feature information 1820 is determined from a set of training images 1810 using a machine learning approach as described herein, for example a convolutional neural network approach. In other embodiments, training feature information series 1820 may comprise training image series 1810.

In step 1702 each instance of training feature information F' is annotated to associate it with training label information L, which is information about one or more classes associated with the training feature information F'. In FIG. 21, a set 1830 of n instances of training label information (L1 to Ln) is shown schematically. In FIG. 21, dashed lines indicate the association of each instance of training label information L to an instance of training feature information F', an image I' and an acquisition time T, such that, for example, training label information L2 is associated with training feature information F2' determined on the basis of image I2' acquired at time T2. The combination of a plurality of instances of training feature information 1820 and a plurality of instances of training label information 1830 associated with the instances of training feature information may be termed a training dataset. The training label information of the training dataset may comprise information about one or more morphokinetic events associated with embryo development. An instance of training label information associated with an instance of training feature information may comprise, for example, at least one class relating to a morphokinetic event, and an associated likelihood value for each class indicating a likelihood that the embryo associated with the training feature information is associated with the morphokinetic event indicated by the class.

For example, an instance of training feature information F' from sequence 1820 in FIG. 21 may be associated with a training image I' of an embryo, having been determined from the training image I' via a feature information determination step, such as described herein in relation to step S5 of FIG. 4. An instance of training label information L associated with an instance of training feature information F' may comprise information about one or more transition probabilities associated with an embryo represented in the image I' from which the instance of training feature information F' has been determined. Thus, for example, an instance of training label information Ln' might comprise a plurality of k likelihood values respectively associated with k classes, wherein each class is associated with a respective morphokinetic event. Each likelihood value k indicates the likelihood that an embryo represented in training image In' is associated with the respective class (and thus morphokinetic event/developmental event). In some embodiments, an image highly associated with a morphokinetic event may be considered to be an image immediately preceding or immediately following the event. This may particularly be the case if the time interval between image acquisitions is long compared to the time duration of a given morphokinetic event, such that features associated with the progression of the event are typically not captured in any of the images (i.e. they occur between the images). In such a case, a certain image in a time series may be considered as the earliest representation of an embryo in the series in which the event is considered to have occurred. The preceding image may be considered as the latest image in the series in which the event is not considered to have occurred. In such an instance, one of these two images may be considered to be the image in series 1810 most representative of the given event. Accordingly, the likelihood value for that event/class in the associated training label information L may be assigned a relatively high value for said class compared to the training label information L for this class for the other images in the series 1810.

In one embodiment, an instance of training label information L comprises a plurality of classes indicative of one or more different transition events, such as a cleavage from a 1-blastomere embryo to a 2-blastomere embryo, such as a cleavage from a 2-blastomere embryo to a 3-blastomere embryo, and so on, i.e., more generally cleavage from an n-blastomere embryo to an n+1-blastomere embryo, the start of compaction (SC), the fading of pronuclei (tPNf), the appearance of morula (M), initial differentiation of trophectoderm (IDT), the start of blastulation (SB), the formation of a blastocyst (B), the initial differentiation of inner cell mass (IDICM), the onset of expansion of the blastocyst (EB), the hatching of a blastocyst (HB), the fully hatched blastocyst stage (FH), appearance of first polar body, appearance of second polar body, appearance of first pronuclei, appearance of second pronuclei, time of pronuclei alignment, start of blastocyst collapse, or start of blastocyst re-expansion. A likelihood value for each class indicates a probability, likelihood or confidence that an embryo represented in the training image I' is associated with the transition event associated with the class. The term 'associated' as used herein will be taken to mean that the image represents an embryo in a state coming before, during or after the transition event, such that the image is considered to have been acquired at a time which corresponds significantly to the range of time over which the event occurs. Once determined, a given instance of training label information Ln is assigned to training feature information Fn' determined from the given training image In'.

In some instances, a transition event, or other morphokinetic event of interest, may not be observed in the series of images, in which case the relevant event may be referred to as a 'hidden' event. That is to say, there may be an event for which no associated features are discernible in any images in the image sequence used to determine a sequence of instances of training feature information. Thus for transition events which are known to follow a sequence such that an event n is preceded by event n−1 and followed by event n+1, it may be the case that in a given sequence of images, an image k contains representations of features strongly associated with event n−1, and image k+1 contains representations of features strongly associated with event n+1. In this instance the event n can be assumed to have occurred in the intervening time between the acquisition of image k and image k+1 such that event n is 'hidden' (i.e. features associated with event n are not represented in any of the images in the sequences). When determining an instance of training label information in the case that an event n is considered to be a hidden event, the likelihood value for the class representing event n may be set to take its maximum value in the instance of feature information associated with the image in which the non-hidden event n+1 is at its maximum value. For example, an image k may show a 2-cell embryo, and an image k+1 may show a 4-cell embryo, so that the transition to a 3-cell embryo must have occurred (unless it did not occur at all due to simultaneous division) between images k and k+1. In this case, the event timing for t3 may be in effect set to the time of image k+1.

In another embodiment, an instance of training label information L associated with an instance of training feature information F' may comprise a single value indicating a general transition probability, wherein the value indicates the likelihood that an embryo represented in a training image is associated with any transition event. In one example, the general transition probability value may be assigned a value of '1' if the embryo in the training image is highly associated with a transition event (for instance, features indicative of an intra-cell-division state are observable in the training image), and the value may be assigned a value of '0' if the embryo represented in the training image is not associated with a transition event.

In other embodiments, an instance of training label information L may comprise values indicating a combination of probabilities relating to developmental/morphokinetic events such as transition events. Thus, for example, an instance of training label information L may comprise a value indicating a general transition probability and further values indicating probabilities for other specific or generalised transition events. The particular choice of events/features to include in training label information may be decided based on user judgment, experimentation and/or modelling.

As will be appreciated, what is in some cases significant is that the label information is information about one or more high-level developmental features which are useful for distinguishing between different embryos and/or the same embryo at different stages of development. Each of the classes comprising the label information may relate to any morphokinetic parameter associated with an embryo cycle, stage, event, or class. Hence classes can be associated with cell cycles, cell division events, and other stages of embryo development as described herein.

The process of determining training label information L, including associating an instance of training label information L with an instance of training feature information F', may be called annotation. Annotation may be carried out by a user, for example, an embryologist, using a general purpose computer such as computer 110 shown schematically in FIG. 3, having a graphical user interface such as display 1180 and one or more input devices such as devices 1190 and 1191. To associate training label information L to an instance of training feature information F', the user may display on a graphical display 1180 an image I' associated with the instance of training feature information F', for example, an image from which the feature information was determined, using, for example, a machine learning approach as described herein in accordance with step S5. The image may be acquired, for example using imaging apparatus 120, or by reading stored data from HDD 117.

The user next determines one or more values relating to one or more morphokinetic events that may be associated with the embryo. These values are each assigned to a respective class for the morphokinetic event. For example, a morphokinetic event determined during annotation may be a transition between two cell cycles, and a likelihood value for the event for a given embryo displayed to the user indicates a likelihood that the embryo is in a state of transition from one cycle to another. For a given image, the determination of a likelihood value for one or more morphokinetic events may involve the user reviewing images prior to and subsequent to the position of said image in the time series. Once a value for each morphokinetic event (i.e. a value for each class) has been determined based on features observed in the image (and potentially taking into account features in images prior and subsequent to the image in the time series of images), this information may be referred to as label information, be stored in a suitable data structure, for example a vector or array of numeric values, and associated with an instance of training feature information F' that is linked to the image I'. Thus in this embodiment it can be considered that training image information from which training feature information has been determined is used as a guide for annotating the training feature information.

What is in some cases significant about the annotation of training feature information is that the training label information provides information about a target state for a classification of feature information. Thus it will be appreciated that the training data may comprise a plurality of instances of training feature information F' which relate to the features of an embryo at a plurality of time points during development, and instances of training label data L respectively associated with each instance of training feature information F', which indicate the likelihood that each instance of feature information is associated with a developmental stage at which the embryo is undergoing one or more morphokinetic events (i.e. a given morphokinetic event was occurring at/near the time T with which a given instance of training feature information F' is associated). Such information can be acquired using any suitable approaches for image acquisition and annotation. The process used to carry out annotation is not of particular importance, and though a relatively user-intensive method has been described as one example, annotation could be achieved using any manual, semi- or fully-automated approach. For example, feature information previously classified using a machine learning approach, and for which information about classes associated with the feature information has thus been determined, may be used for training the machine learning approach.

A training dataset for training the machine learning approach in step S6 may comprise a sequence of instances of training feature information, such as the sequence of instances of training feature information 1820 in FIG. 21, and a corresponding sequence of instances of label information, such as the sequence of instances of label information 1830 in FIG. 21, such that each instance of training feature information is associated with an instance of label information. A training dataset used for training a machine learning approach may comprise a sub-sequence of feature objects and corresponding data label information sub-sampled from a longer parent sequence.

In one embodiment, at least one sub-series of instances of feature information may be sampled from a host series based on at least one time-point in a parent series at which a morphokinetic event of interest is determined to have occurred. For example, a parent sequence of instances of feature information may comprise 100 instances of feature information determined from 100 images of an embryo acquired at sequential times during development. During annotation, it may be determined that the 20th instance of training feature information in the parent sequence (i.e. F20') is strongly associated with a particular cell division event between cycles cc1 and cc2a. This may be determined, for example, on the basis of inspecting the training image I20' associated with the 20th instance of training feature information F20' and observing that of all the training images in the parent sequence this image shows the clearest representation of features indicating a cell division event at t2 between cycles cc1 and cc2a. Following this determination, the user may define a sub-set of the time series of instances of training feature information around the training feature information deemed to be associated with the particular cell division event (i.e. F20'), for example comprising the range from F20'−i1 to F20'+i2, where i1 and i2 where in one embodiment i1 is set to 19 and i2 is set to 20. Thus the sub-set of the time series of instances of training feature information around the training feature information F20' comprises the range of instances of feature information from the $1^{st}$ in the parent sequence to the $40^{th}$ in the parent sequence. The instances of training feature information F' in the sub-sequence may then be annotated using approaches described above. It will be appreciated that this may reduce the training time by providing as a training dataset instances of feature information that are most likely associated with target morphological event(s). Any number of sequences or sub-sequences of training data may be employed in the training stages used to configure the machine learning approach for determining morphokinetic event information.

In step 1703 the machine learning approach is initialised. In some embodiments the machine learning approach comprises a support vector machine. In some embodiments the machine learning approach comprises a graphical model such as a Markov random-field model or a Bayesian model. In some embodiments the machine learning approach comprises using feature quantification combined with a random-forest classifier. In some embodiments the machine learning approach comprises a feature clustering approach, such as K-means clustering. In some embodiments the machine learning approach comprises an artificial neural network, such as a recurrent neural network (RNN). In one embodiment, a bidirectional RNN comprising long short term memory (LSTM) building blocks is used. The machine learning approach may be configured to run on a general purpose computer such as the computer system 110 shown in FIG. 3. The machine learning algorithm may be configured to run on a CPU, such as CPU 111 shown in FIG. 3, or a GPU such as GPU 116 shown in FIG. 3. The skilled person will recognise that the machine learning approach may be configured to run within a framework known in the art, such as those provided by TensorFlow, Theano, Torch, Caffe, or the Waikato Environment for Knowledge Analysis. Alternatively the approach may be programmed using a suitable programming language, for example, Python or C++.

Also in step 1703, a configuration of operators, functions, weights, biases, and other parameters relating to the operation of the machine learning approach may be selected. For example, in one embodiment the machine learning approach comprises a recurrent neural network (RNN), and the configuration of the approach may comprise selecting a number of layers, selecting a number of nodes per layer, selecting and configuring activation functions, selecting and configuring weighting coefficients (or 'weights') selecting and configuring biasing coefficients (or 'biases'), selecting and configuring convolution/deconvolution operators, selecting and configuring pooling operators, selecting and configuring sub-sampling operators, selecting and configuring rectifying operators, selecting and configuring one or more classification layers, selecting and configuring one or more state variables. Suitable operators and parameters values may be selected, for example, based on experimentation or modelling.

In one embodiment, the machine learning approach comprises a bidirectional RNN comprising LSTM memory blocks, and one or more state parameters/variables may be configured as part of initialisation step 1703. The skilled person will appreciate that what is in some cases significant about a RNN is that the network comprises an internal memory state which stores information relating to past and/or future processing events. Thus when an input of feature information F is classified by the neural network, the classification for that input is made partly on the basis of information associated with the processing of preceding and/or following inputs. What will be appreciated about this approach is that it enables a classification of an input F to be carried out by a neural network such that a preceding and/or following pattern of inputs to the neural network partly determines the classification of current input F. In other words, the neural network classifies a current input based partly on a history or memory of past and/or future input classification events. The degree to which past and/or future inputs influences the classification of a current input may be controlled by the selection and configuration of suitable state parameters/variables.

The configuration of the machine learning approach in step 1703 will be conducted such that the output of the machine learning approach is related to the objective task of the machine learning approach. In other words, the output of the machine learning approach may be in a format which enables it to be compared to training label information. For example, if training label information is an n-dimensional vector of values where each value ranges between '0' and '1', the machine learning approach may be configured to generate an output for each input instance of feature information which is in the form of an n-dimensional vector of values ranging from '0' to '1'.

Steps 1704, 1705, 1706 and 1707 comprise a training stage, which may be iterated over a plurality of times in order to train the machine learning approach to carry out the task to an appropriate level of accuracy. In some embodiments, the objective of the training task is to minimize the error between the label information associated with an instance of training feature information F', and the output O' generated by applying the machine learning approach to the instance of training feature information. The error may be minimized with respect to a plurality of training stages applied to a single instance of training label information, and/or a plurality of training stages applied to a plurality of instances of training label information.

Figure 23:
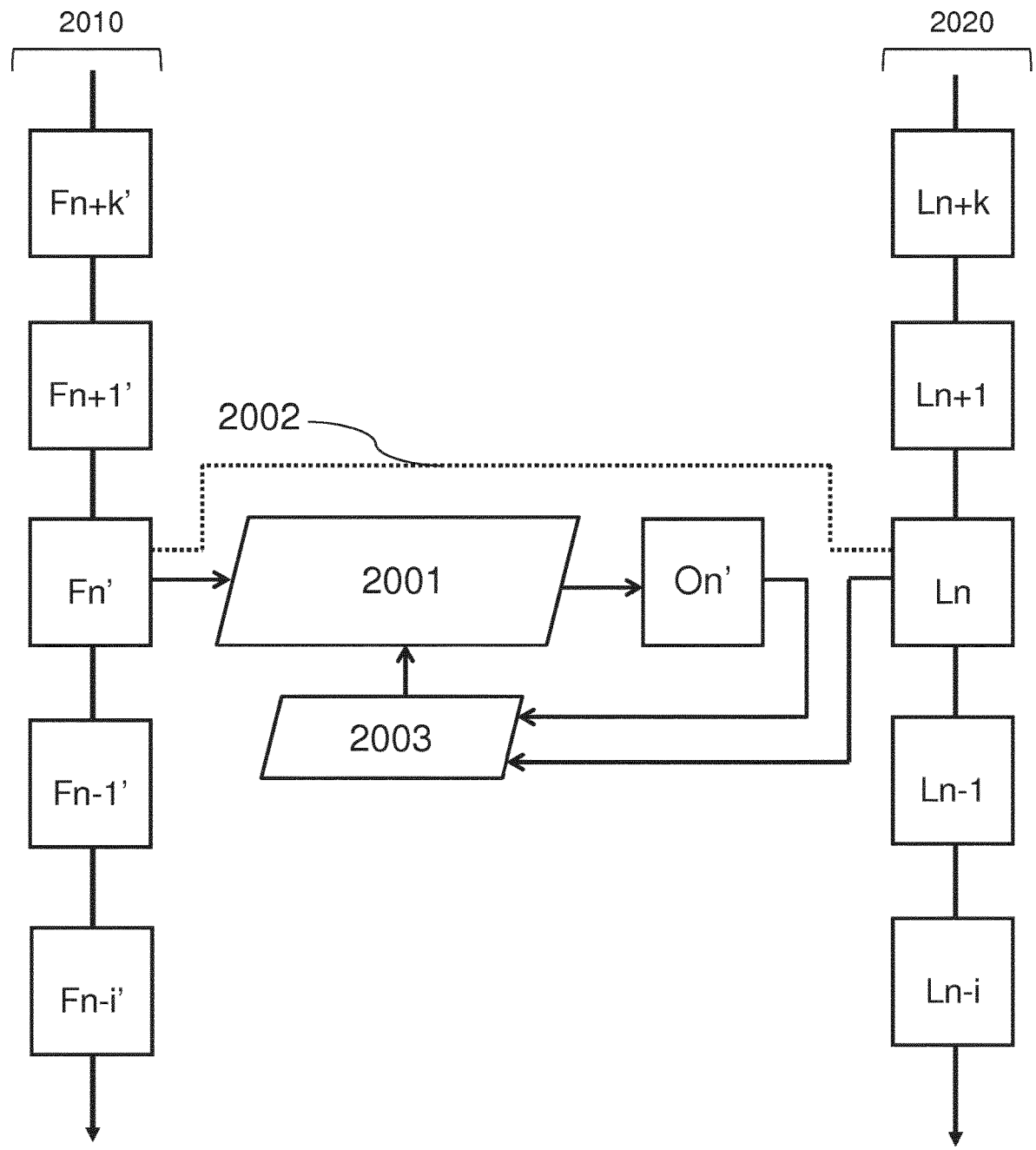
FIG. 23 schematically represents a method for training a machine learning approach to determine morphokinetic event information on the basis of a time series of feature information.

Thus in step 1704, and as shown schematically in FIG. 23, an instance of training feature information (Fn') from a sequence of instances of training feature information 2010 is applied as an input to the initialised machine learning approach 2001. For example, in one embodiment the machine learning approach is a RNN, and an instance of training feature information Fn' is supplied as an input to the input layer of the RNN 2001. The input of training feature information Fn' has been preceded by instances Fn−1', . . . , Fn−i', where i is the total number of prior instances of training feature information. The input of training feature information Fn' is followed by instances Fn+1', . . . , Fn+k', where k is the total number of future instances of training feature information. The classification of prior and/or future instances of training feature information is reflected in the current state of RNN 2001 as it processes training feature information Fn'.

In step 1705, an output is generated by applying the machine learning approach to the input of training feature information. FIG. 23 schematically shows an output On' of morphokinetic event information determined by machine learning approach 2001 on the basis of training input feature information Fn'. In one embodiment the approach 2001 comprises a RNN, and the output of morphokinetic event information O' comprises a vector of likelihood values each of which is associated with a target class. For example, a likelihood value for a class may be a numeric value between '0' and '1', where the value is related to a likelihood that the input training feature information Fn' is associated with an embryo that is in a state of undergoing a given morphokinetic/developmental event associated with that class. The particular choice of format for the output is not particularly significant. It will appreciated that what is in some cases significant about the output On' is that it provides information on the likelihood of a representation of an embryo associated with the training feature information Fn' being associated with each of one or more target classes associated with one or more respective morphokinetic events.

In step 1706, the output of morphokinetic event information On' is compared to label information Ln associated with the input instance of feature information Fn' (this association being represented by dashed line 2002). The objective of the comparison is to determine how closely the output On' of the machine learning approach 2001 matches the label information Ln. In one embodiment, this comparison is used to determine an instance of error information, which is information quantifying the degree of difference between the output and the label information. This may be achieved, for example, through use of an appropriate error function such as a cross-correlation function. FIG. 23 schematically shows training label information Ln (associated with input feature information Fn') and output On' from machine learning approach 2001 being provided as inputs to a comparison step 2003.

In step 1707, the error information determined in step 1706 is used to modify the operation of the machine learning approach 2001. FIG. 23 schematically shows the output of a comparison 2003 between training label information Ln and output On' being used as an input to modify the machine learning approach 2001. The modification is carried out such that re-applying steps 1704, 1705 and 1706 using the same training image I' and the modified machine learning approach 2001 results in a lower error between the output On' and the label information Ln, as determined by comparison 2003. For example, the machine learning approach 2001 may comprise a plurality of operators and a plurality of parameters (including, for example, weight coefficients, state parameters, classes and other variables), and any of these may be adjusted during step 1707. In another embodiment, the machine learning approach 2001 comprises one or more decision trees, and parameters associated with one or more decision trees may be adjusted during step 1707. In another embodiment, the machine learning approach comprises a neural network, and a gradient descent approach or other backpropagation method is used to update weights and/or states and/or other parameters relating to the operators of hidden layers of the neural network on the basis of error information.

As will be appreciated, what is significant about the training stage is not a particular training method, but that the method chosen for training is able to modify some characteristic(s) of the neural network in order to enable the network to generate an output for a given instance of feature information which more closely approximates the training label data for that input (i.e. reduces a measure of error between label information Ln and output On' for a given instance of training feature information Fn'). Steps 1704 to 1707 may collectively be referred to as a training stage, and a plurality of successive training stages may be carried out until the machine learning approach is considered to be fully trained. Thus in 1708 the next instance of training feature information in the time series is selected, and steps 1704 to 1707 are repeated for this next instance of training feature information. Furthermore, in some implementations the machine learning approach used may be an unsupervised machine learning approach, such as an autoencoder approach or a semi-supervised machine learning approach.

A determination of the state of training may be based on the change in error (i.e. error between label information L and output O') over successive training stages. For example, iteration through successive training stages may continue until a change in the measure of error with successive iterations effectively reaches zero. In other examples, iteration through successive training stages may continue until the change in the measure of error with successive iterations drops below a predetermined threshold. The condition whereby the change has reduced to a suitably low value may be referred to herein as a training stop condition. The determination of whether a stop condition is reached may be achieved, for example, by differentiating over the output error with respect to training stage number in order to quantify the change in error value over training stage. In some embodiments, a predetermined number of training stages is defined, and if the change in error does not reach a stop condition within the given number of stages, a further set of stages is defined and training continues. However, if the stop condition is reached within the predetermined number of training stages, training may in some instances be considered to be complete.

The determination of whether the machine learning approach is suitably trained may alternatively or in addition be based on the results of a validation stage. Some aspects of the validation stage will be recognized from the training stage and the validation stage may use a validation dataset, which may be acquired in the same manner as the training dataset (i.e. comprising a time series of instances of feature information with associated label information) but which have not been used in the training of the machine learning approach. Hence, in one embodiment, the performance of the machine learning approach is checked by incorporating a validation stage at various intervals during training, in which the partially trained machine learning approach is applied to a plurality of instances from a sequence of validation feature information and a level of error is determined on the basis of a comparison between the output of the machine learning approach for each instance of validation feature information and a respective instance of label information associated with the instance of validation feature information. The error may be averaged over multiple instances of input validation feature information, for example, over an entire time series, or over a sub-series of feature information. At each validation stage, the resulting error value may be compared to some threshold value, and training may continue until the error value as determined during the validation stage is below the threshold value. In some embodiments, a validation stage may be incorporated following a predetermined number of training stages. In other embodiments, a validation stage may be introduced once the training is considered to be complete on the basis of the change in error with successive training stages effectively reaching zero or falling below a predetermined threshold.

Figure 22:
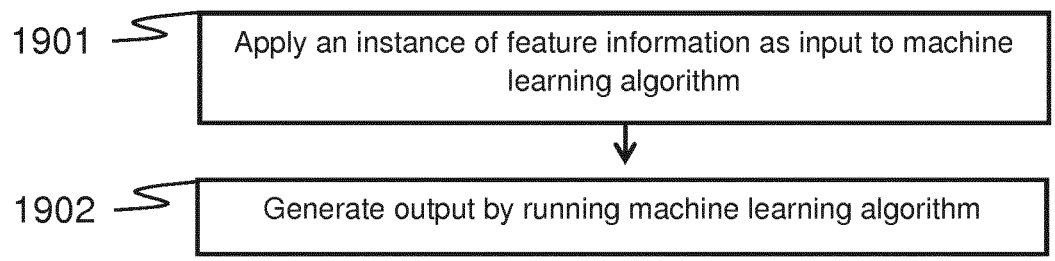
FIG. 22 schematically represents a method for applying a machine learning approach to determine morphokinetic event information on the basis of feature information.
Figure 24:
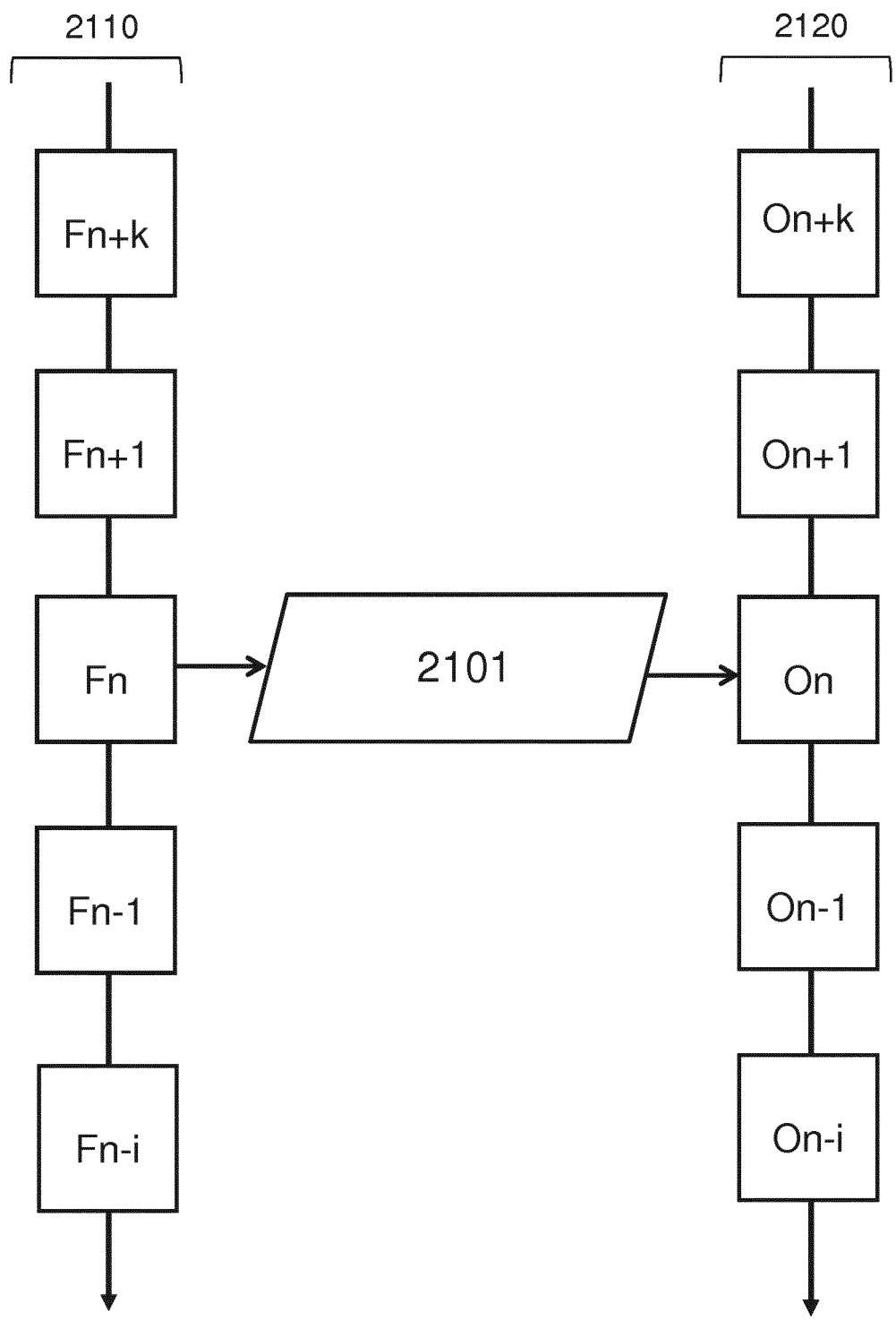
FIG. 24 schematically represents a method for applying a machine learning approach to determine a time series of morphokinetic event information based on a time series of feature information.

Following training of the machine learning approach 2001, and with reference to the schematic shown in FIG. 24, the trained machine learning approach 2101 is applied to a time sequence of instances of feature information F to generate a sequence of instances of morphokinetic event information O. With reference to the schematic shown in FIG. 22, in step 1901, an instance of feature information Fn from a time series of instances of feature information 2110 is applied as an input to a trained machine learning approach 2101. In step 1902, the trained machine learning approach 2101 is used to determine an output (On) on the basis of the input instance of feature information Fn. As shown schematically in FIG. 24, the input of feature information Fn belongs to a time series of instances of feature information 2110 which may comprise past instances Fn−1, . . . , Fn−i and may comprise future instances Fn+1, . . . , Fn+k. It will be appreciated that the determination of morphokinetic event information (On) on the basis of the current input Fn may be influenced by the history of processing of past instances and future instances of feature information in the time sequence to which Fn belongs. In other words, what may in some cases be considered significant about the machine learning approach is that a plurality of sequential instances of feature information is relevant to the determination of morphokinetic event information for a single current input of feature information. The process of determining an instance of morphokinetic event information O on the basis of an instance of feature information F may be repeated over sequential instances of feature information from a time series of any length, for example, an entire sequence of information collected for an embryo over the course of a complete developmental process from insemination to implantation, or a partial sequence for an embryo at any intermediate stage between insemination and implantation.

It will be appreciated that the trained machine learning approach 2001 may be applied to a time sequence of instances of feature information that does not represent a complete developmental sequence. For instance, though an embryo imaged for example by imaging system 120 may be imaged periodically from insemination to implantation, the steps S1 to S5 shown schematically in FIG. 4 may be applied to determine morphokinetic event information O from a time series of images which is incomplete in the sense that the embryo is still being monitored by the imaging system 120 (i.e. the time series of images representing in vitro development is still being added to at the point where morphokinetic event information O for the current time series is determined). It will be appreciated that the steps S1 to S5—through which a time series of feature information is determined on the basis of a time series of image information, and morphokinetic event information is then determined from the time series of feature information—may be carried out using a time series of images at any stage of completion. Thus, the determination of morphokinetic event information O for a given embryo, determined using the methods associated with steps S1 to S5 as described herein, may be carried out a plurality of times during development of the embryo, providing up-to-date information on embryo development which may be used to guide decisions on culturing parameters and embryo implantation, for example to facilitate a decision on when to transfer an embryo to a patient, for example whether to do so on day 3 or day 5 after fertilisation.

Furthermore, as discussed above the term mask/segmentation/label field as used herein generally refers to information associating one or more pixels comprising an image to one or more classes, such as, for example, an embryo class and a background class. Thus a mask may in some instances be used to guide cropping of an image with which the mask is associated, by, for example, enabling scaling a cropping region of interest based on the spatial distribution of pixels associated with a given class comprising the mask. In some embodiments, the borders of a cropping ROI are defined such that the cropping ROI substantially encloses the pixels in an image that are defined by an associated mask as belonging to, for instance, the embryo class as discussed above. However, it will be appreciated that a mask associated with an image may also be used to define a set of pixels in the image which are to be ignored or otherwise processed differently during a feature information determination step for which the image is used as an input. For example, an image used as an input to a feature information determination step may be associated with a mask which defines each pixel in the image as belonging to an embryo class and a background class. This mask may be determined using approaches as described herein, and may take the form of a second image with the same dimensions as the first image with which it is associated, and in which at a given pixel location the mask image takes a value of '1' if the corresponding pixel in the first image is associated with an embryo feature, and takes a value of '0' if the corresponding pixels is associated with the background. Alternatively, the mask may take the form of an array in which the pixel coordinates in the first image are recorded, along with an indication of the pixel class. A mask thus defined may be used to modify an image used as an input to a machine learning approach (such as, for instance, a feature information determination approach), which may have also have been cropped and/or rescaled using approaches as described herein. For example, the image may be modified such that pixels in the first image that are indicated on the basis of the associated mask not to belong to the embryo class are set to a value such as zero, or some other suitable value (e.g. NaN) to indicate that they should be processed differently to pixels not having said value by the feature information determination approach (for instance, comprising a neural network or other machine learning approach). In this way, the feature information determination approach may in effect be configured to disregard pixels that are not determined on the basis of the mask to correspond to embryo features. This may also be achieved without modifying the image prior to input, for example by applying the mask information as an additional input to the machine learning approach.

It will also be appreciated that a likelihood value associated with a class comprising label information as described herein may be a continuous variable, and may be assigned any value between, for example, 0 and 1, where 0 represents the lowest likelihood and 1 represents the highest likelihood (though it will be appreciated that any range could be used). Thus a user may determine a likelihood value taking any value between and including the maximum and minimum values in the range. However, in some instances the user may use a binary determination, such that the likelihood value may take one of a finite number of values, for instance, either '0' for a lower likelihood or '1' for a higher likelihood. It will further be appreciated that whereas likelihood values comprising label information may generally be assigned by a skilled user on the basis of observation, such values may equally be derived from other sources. In some embodiments, metadata (for example, values from a database) associated with training data to which training label information is to be assigned is used to determine likelihood values. In some embodiments, training data to which training label information is to be assigned may comprise data (such as images or instances of feature information) which have previously been processed by a machine learning approach to estimate likelihoods for one or more classes, and the resulting likelihoods (which may be binary indications or continuous variables) may be assigned as training label information to the training data. Thus what may be considered significant in some cases is that likelihood values comprising training label information to be associated with training data may be determined without a user manually defining such values on the basis of, for example, visual inspection of images.

In step S7 of FIG. 4, a sequence of events relating to embryo development is determined on the basis of a set of outputs of morphokinetic event information from the prior step, such as the time series 2120 shown schematically in FIG. 24. A sequence of events thus determined may be referred to as a morphokinetic event timeline, and may comprise one or more morphokinetic event classifications along with associated timing information. An event classification may be information indicating a particular morphokinetic event, such as those described herein. For example, a morphokinetic event classification may be a cleavage event between a 1-blastomere embryo and a 2-blastomere embryo, a cleavage event between a 2-blastomere embryo and a 3-blastomere embryo, a cleavage event between a 3-blastomere embryo and a 4-blastomere embryo, and more generally a cleavage event between an n-blastomere embryo and an n+1-blastomere embryo, or any other morphokinetic event discussed herein.

Morphokinetic event classifications may be determined based on a time series of output information 2120 such as that shown schematically in FIG. 24. Thus, and with reference to FIG. 25, in one embodiment, a processing step 2201 is used to determine an event timeline Te on the basis of a time series of instances of output information 2210, for example, a time series of instances of morphokinetic event information O determined using approaches such as those set out herein in relation to step S6 of FIG. 4. This may be referred to as a dynamic programming step. What is in some cases significant about this step is that morphokinetic event classifications and timings are determined comprising an event timeline, said determination being made on the basis of a time series of instances of morphokinetic event information 2210 for which timing information is known (such as an acquisition time T associated with each instance of morphokinetic event information O). For example, a set of instances of morphokinetic event information 2210 may comprise n instances, such that each instance of output information On is associated with a time Tn. The time Tn may be an acquisition time associated with the instance of feature information Fn used to determine output information On, which has in turn been determined on the basis of an image In. As discusses herein, each instance of output information On comprises likelihood information determined by a machine learning approach on the basis of a sequence of feature information Fn, and comprises likelihood values assigned to each of one or more classes, each of which is associated with a respective morphokinetic event.

In one embodiment, each instance of morphokinetic event information O comprises a plurality of classes, whereby each class is associated with a transition event, such as a cell cleavage event. Each instance of morphokinetic event information O is furthermore associated with a time T. Thus the processing step 2201 may take as an input a plurality of instances of morphokinetic event information O, along with associated timing information, and output a set of estimated event classifications and timings that is determined on the basis of the morphokinetic event information and associated timing information.

Figure 25:
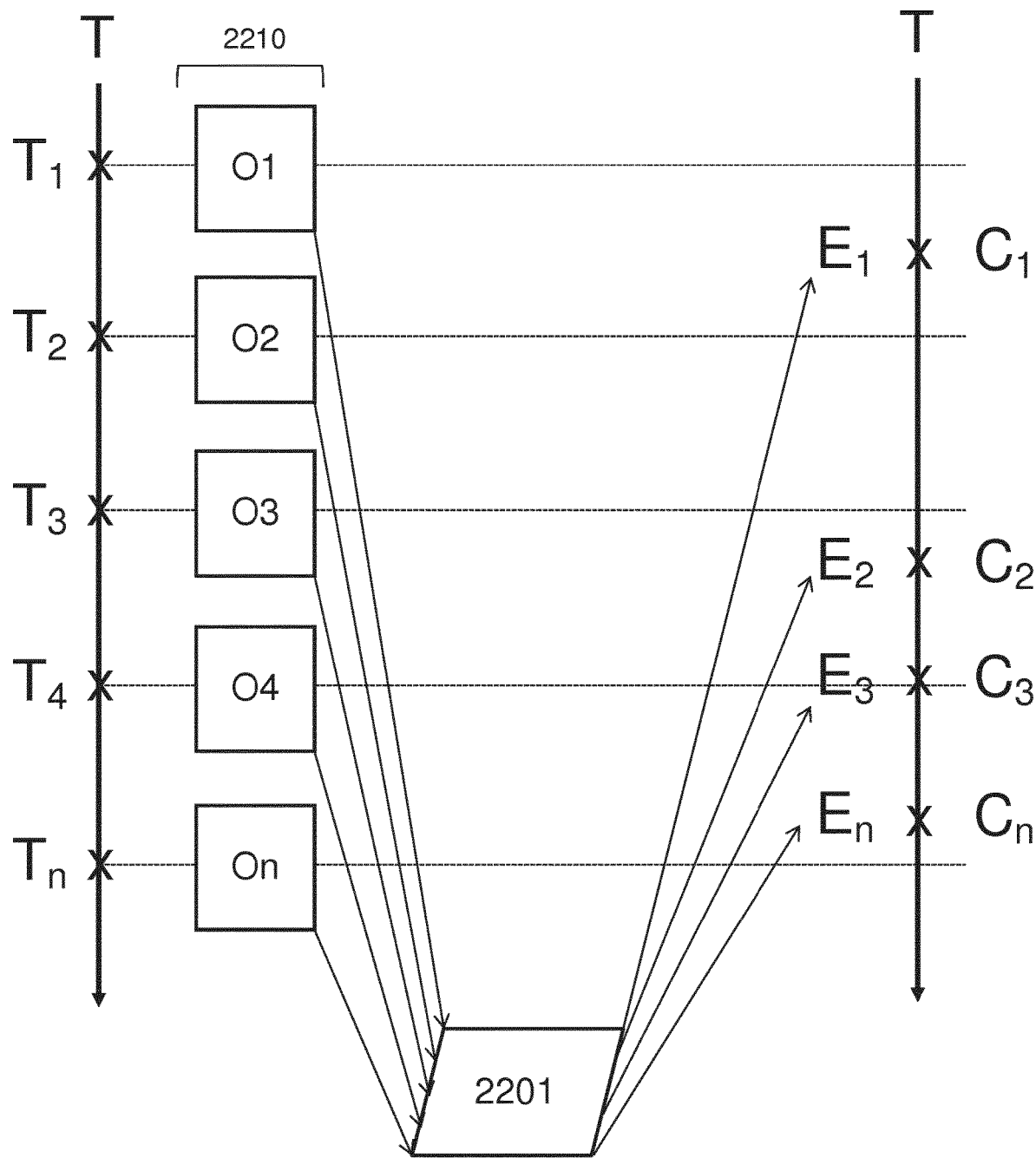
FIG. 25 schematically represents a method for determining a sequence of development events and associated confidence values on the basis of a time series of morphokinetic event information.

Thus, as shown schematically in FIG. 25, the processing step 2201 may take as an input one or more instances of morphokinetic event information O from a sequence 2210, each of which are associated with a respective acquisition time T on the acquisition timeline Ta. Thus in one embodiment, an instance of morphokinetic event information On is determined on the basis of an instance of feature information Fn which is determined on the basis of an image In acquired at a time Tn. The morphokinetic event information 2210 and the associated timing information comprise the input to the processing step 2201. The processing step 2201 determines, on the basis of these inputs, a sequence of event classifications E1, E2, E3, En with associated times indicated on event timeline Te, as shown schematically in FIG. 25. Thus in one embodiment, the morphokinetic event information O comprises n−1 classes respectively referring to a cleavage event to a 2-blastomere embryo, a cleavage event to a 3-blastomere embryo, a cleavage event to a 4-blastomere embryo, and a cleavage event to an n-blastomere embryo. A likelihood value is associated with each class, determined on the basis of the machine learning approach outlined in step S6 of FIG. 4. With respect to FIG. 25, in this embodiment event classification E1 is associated with a cleavage event to a 2-blastomere embryo, classification E2 is associated with a cleavage event to a 3-blastomere embryo, classification E3 is associated with a cleavage event to a 4-blastomere embryo, and classification En is associated with a cleavage event to an n+1-blastomere embryo. The processing step 2201 determines from the time series of morphokinetic event information 2210 the positions of event classifications E1 to En on the event timeline Te. Thus the processing step 2201 may be considered to determine a sequence of morphokinetic/developmental events and associated timings on the basis of a plurality of inputs of morphokinetic event information comprising a time-series of instances determined by a machine learning approach on the basis of a time series of feature information.

The processing step 2201 may comprise a rule-based approach, in which one or more rules are used to determine a permissible order of morphokinetic events. For instance, a rule may be defined to specify that a certain first morphokinetic event may not occur after a certain second morphokinetic event on the event timeline Te. In one example, the set of morphokinetic events to be determined comprises cleavage events, and an example of a rule would be to specify that the events cannot be so ordered in the event timeline such that a cleavage from n cells to n+1 cells precedes a cleavage from k cells to k+1 cells where n>k (thus with respect to the example given above, En−i must be before En). Rules comprising the processing step 2201 may be determined by a user, for example, an embryologist, on the basis of knowledge of patterns of embryo development known to the skilled person.

It will be appreciated that a number of approaches can be used to determine or estimate a most likely sequence of morphokinetic events based on instances of morphokinetic event information which respectively comprise information about the likelihood of incidence of one or more morphokinetic/developmental events associated with a respective instance of feature information representing the state of an embryo at a given time. For example, a graphical modelling approach may be used in some embodiments to describe permissible events and associated likelihoods given a particular state, for instance, the possible transition events (e.g. cleavage events) for an embryo, along with their associated probabilities of occurrence. For example, in some embodiments, this may take the form of a hidden Markov model (HMM) describing the set of potential morphokinetic event sequences. Determining the most likely sequence of morphokinetic/developmental events and associated timings in these embodiments may be considered to be achieved by determining the most likely path through the HMM, based on the information about developmental/morphokinetic event probabilities/likelihoods that comprises the set of morphokinetic event information 2210 determined from the time sequence of instances of feature information using the machine learning approaches described further herein. There are a number of known approaches through which such a path can be determined which may be used. Thus in some embodiments, the most likely event path (i.e. events E1 to En and associated timing information) through a graphical model representing all possible event sequences is determined on the basis of morphokinetic event information 2210 using a Viterbi algorithm. More generally, any dynamic programming algorithm may be applied to determine a highest-likelihood event sequence on the basis of morphokinetic event information 2210.

The dynamic programming step may also take into account additional information provided by a user. For instance, if it is known on the basis of observation or other approaches that a given morphokinetic/developmental event should be considered to occur at a certain position in an image sequence, this information can be incorporated in the dynamic programming step in order to constrain the determination of the highest-likelihood event sequence. Thus for example, if image n in a time sequence of images, corresponding to a time T, is determined by a user to correspond strongly to a given morphokinetic event E, a dynamic programming step used to determine the optimum event sequence may be provided by the user with an input of information specifying that the morphokinetic event E should be bound to/weighted towards time T. Thus the dynamic programming step will determine a highest-likelihood sequence of morphokinetic events and associated timings which takes into account both the morphokinetic event information determined from feature information via a machine learning approach, and additional information provided/annotated by a user. Though this is one example, what may be considered in some cases significant to this approach is that information provided by a user may be used to constrain or otherwise influence the operation of the dynamic programming operator(s) used to determine when certain events should occur in a developmental sequence on the basis of morphokinetic event information.

In step S8 of FIG. 4, a confidence value or interval C (which may be referred to as confidence information) is determined for one or more of the event classifications E determined by the processing step 2201 shown schematically in FIG. 25. Thus, in FIG. 25, event classification E1 has associated confidence information C1, event classification E2 has an associated confidence information C2, event classification E3 has an associated confidence information C3, and event classification En has an associated confidence information Cn. What is in some cases significant about the confidence information is that it represents a measure of certainty for the timing on the timeline Te determined for an associated event classification E. In other words, the confidence information is a means of quantifying the degree to which the position of an event E in a sequence, determined by the approaches described herein, represents a unique solution. Where there is uncertainty over the best determination of a given timing and/or position in a sequence of an event E, the respective confidence C should be lower, and where the determination of the event is highly certain (e.g. there are no other potential candidates for the timing and/or position in the sequence of a given event), the respective confidence should be higher.

There are various known approaches to determination of confidence information. The confidence information may, for example, be determined based on one or more of the estimated timings (e.g. if an event is estimated to have a timing that is far removed from a typical value or range, it may be associated with a relatively low confidence estimate); feature information; and/or an estimated development event likelihood for an image (i.e. a likelihood of the image being associated with a particular developmental event). In some implementations the determination of the confidence information may be done as part of the processing step 2201 (e.g. dynamic programming), and in other cases the confidence information may be determined separately from the associated event timings, for example in a machine learned approach. In one embodiment, an instance of confidence information for an event in a morphokinetic event sequence is determined on the basis of one or more residuals determined during the processing step 2201 used to estimate the timing of events comprising a morphokinetic event sequence. A residual in this case may be understood to be a value quantifying the uniqueness of the determination of a certain timing and/or position in the sequence of a given event E. An event for which a processing step 2201 (for example, a dynamic programming approach) has determined there are a range of similarly feasible solutions for timing and/or position may return a higher residual than for an event for which there is only one feasible timing or position in the sequence. In one embodiment, estimated timings of events E are determined using a Viterbi algorithm, and the residuals of the determination are used to determine an instance of confidence information for each respective event. An instance of confidence information may be a value, for instance a value between 0 and 1, where a higher value indicates a higher confidence and a lower value indicates a lower confidence. In other embodiments, the confidence information may comprise a range of values above and below a timing determined for a given event in an event sequence.

In some embodiments, confidence information may be determined using a confidence model, which may in some cases comprise a machine learning approach or a statistical approach. What may be considered significant in some cases is that confidence information may be determined from the outputs of the machine learning approach described with relation to step S4 in FIG. 4 (i.e. instances of feature information) and/or the machine learning approach described with relation to step S5 in FIG. 4 (i.e. instances of morphokinetic event information). Thus in some instances confidence information may not be determined on the basis of residuals of a dynamic programming step, but are determined using a confidence model. Thus in some embodiments, residuals derived from dynamic programming as described herein may be used as training label information in order to train or otherwise configure a confidence model to estimate confidence information on the basis of one or more inputs of feature information and/or morphokinetic event information determined using approaches as described further herein. In one embodiment, information about one or more residuals determined using a dynamic programming step (such as the processing step 2201 shown in FIG. 25) is used as training label information and associated with one or more instances of morphokinetic event information O determined by a machine learning approach such as approach 2101 shown schematically in FIG. 24. Thus, for example, one or more instances of morphokinetic event information O and associated training label information are used to train the confidence model to determine a measure of confidence on the basis of one or more instances of morphokinetic event information O. This training procedure can comprise any suitable procedure known in the art, such as approaches to training of neural networks and other machine learning approaches as described further herein. With reference to FIG. 25, once the confidence model is fully trained, instances of confidence information C1, C2, . . . , Cn may be determined for respective events E1, E2, . . . , En by applying one ore more instances of morphokinetic event information O (such as instances O1 to On in set 2210), and events E1, E2, . . . , En as inputs to the confidence model.

In the approaches discussed herein there are various parameters and values for parameters that may be selected by a user for a particular implementation. It will be appreciated these parameters and values may be selected for the particular implementation through modelling or experimentation. For example, in some implementations an iteratively performed aspect of the processing may be repeated until an error between successive iterations falls below a predetermined threshold, and in this case the predetermined threshold may be selected based on a user running the algorithm for different thresholds and identifying a threshold which provides a desired level of performance, e.g. resulting in a desired compromise between runtime and output accuracy.

Thus there has been described computer-implemented method of processing a time series of images of an embryo to determine estimated timings for a plurality of developmental events for the embryo, wherein the method comprises: determining feature information for each of the images, the feature information for each image representing the content of the image; establishing machine learned classifiers for associating each of the images with a respective likelihood of the image being associated with (i.e. representing) one or more of the plurality of developmental events based on the feature information for the image (the machine learned classifiers may be established using supervised, semi-supervised or unsupervised machine learning approaches); applying the machine learned classifiers to the feature information for each of the images to determine a respective likelihood of the image being associated with one or more of the plurality of developmental events; and determining estimated timings for the plurality of developmental events for the embryo from the respective likelihoods of the respective images being associated with respective ones of the plurality of developmental events. The method may further comprise providing output signalling representing the estimated timings, potentially also with an indication of a confidence estimate for the timings, for example by displaying an indication of the estimated timings on a computer display, such as a display associated with the computer 110 of FIG. 3 or storing an indication of the estimated timings (and in some cases an associated confidence estimate for the timings) in a stored data structure. The method may further comprise determining a development potential for the embryo from one or more of the estimated timings, for example taking account of known relationships between timings for developmental events for an embryo and embryo quality.

Further particular and preferred aspects of the present disclosure are set out in the accompanying independent and dependent claims. It will be appreciated that features of the dependent claims may be combined with features of the independent claims in combinations other than those explicitly set out in the claims.

REFERENCES

[1] US20140247972A1
What is claimed is:
1. A computer-implemented method of processing a time series of images of an embryo to determine estimated timings for a plurality of developmental events for the embryo, wherein the method comprises:
determining feature information for each of the images, the feature information for each image representing the content of the image;
establishing machine learned classifiers for associating each of the images with a respective likelihood of the image being associated with one or more of the plurality of developmental events based on the feature information for the image;
applying the machine learned classifiers to the feature information for each of the images to determine a respective likelihood of the image being associated with one or more of the plurality of developmental events; and
determining estimated timings for the plurality of developmental events for the embryo from the respective likelihoods of the respective images being associated with respective ones of the plurality of developmental events,
wherein the plurality of developmental events for the embryo comprise one or more developmental events selected from the group comprising:
(i) any cleavage event
(ii) cleavage to a 2-blastomere embryo;
(iii) cleavage to a 3-blastomere embryo;
(iv) cleavage to a 4-blastomere embryo;

(v) cleavage to a 5-blastomere embryo;
(vi) cleavage to a 6-blastomere embryo;
(vii) cleavage to a 7-blastomere embryo;
(viii) cleavage to an 8-blastomere embryo;
(ix) cleavage to an 9 or more blastomere embryo;
(x) fading of pronuclei;
(xi) start of compaction;
(xii) formation of morula;
(xiii) initial differentiation of trophectoderm;
(xiv) start of blastulation;
(xv) formation of a blastocyst;
(xvi) initial differentiation of inner cell mass;
(xvii) onset of expansion of a blastocyst;
(xviii) hatching of a blastocyst;
(xix) appearance of first polar body;
(xx) appearance of second polar body;
(xxi) appearance of first pronuclei;
(xxii) appearance of second pronuclei;
(xxiii) time of pronuclei alignment;
(xiv) start of blastocyst collapse; and
(xv) start of blastocyst re-expansion.

2. The method of claim 1, wherein the feature information for each image comprises information abstracted from the content of the image.

3. The method of claim 2, wherein the feature information for each image comprises a representation of a frequency distribution of signal values for pixels comprising the image.

4. The method of claim 2, wherein the feature information for each image is abstracted using one or more approaches selected from the group comprising:
(i) a scale invariant feature transform approach;
(ii) a machine learned feature clustering approach;
(iii) a machine learned neural network approach.

5. The method of claim 1, wherein the feature information for each image is the image itself.

6. The method of claim 1, wherein the step of determining feature information for each of the images includes cropping the images.

7. The method of claim 1, wherein the step of determining feature information for each of the images includes resealing the images.

8. The method of claim 1, further comprising segmenting the images to classify pixels in the images as corresponding to the embryo or background, and wherein the feature information for each of the images is determined by preferentially using the pixels classified as corresponding to the embryo over the pixels classified as corresponding to the background.

9. The method of claim 1, wherein the step of determining estimated timings for the plurality of developmental events for the embryo is performed using a dynamic programming approach.

10. The method claim 9, wherein the dynamic programming approach comprises a Viterbi algorithm.

11. The method of claim 1, wherein the time series of images of the embryo comprise a subset of images of the embryo selected from a larger number of images of the embryo.

12. The method of claim 1, wherein each image of the embryo comprises a plurality of frames representing the embryo at substantially the same stage of its development.

13. The method claim 1, further comprising providing output signaling representing the estimated timings.

14. The method of claim 1, further comprising determining a development potential for the embryo using the estimated timings.

15. A non-transitory computer program product bearing machine readable instructions for carrying out the method of claim 1.

16. A computer-implemented method of processing a time series of images of an embryo to determine estimated timings for a plurality of developmental events for the embryo, wherein the method comprises:
  determining feature information for each of the images, the feature information for each image representing the content of the image;
  establishing machine learned classifiers for associating each of the images with a respective likelihood of the image being associated with one or more of the plurality of developmental events based on the feature information for the image;
  applying the machine learned classifiers to the feature information for each of the images to determine a respective likelihood of the image being associated with one or more of the plurality of developmental events; and
  determining estimated timings for the plurality of developmental events for the embryo from the respective likelihoods of the respective images being associated with respective ones of the plurality of developmental events and determining a confidence estimate for respective ones of the estimated timings.

17. The method of claim 16, wherein the confidence estimate for respective ones of the estimated timings is determined based on one or more of the estimated timings; feature information; and the likelihood of an image being associated with one or more of the plurality of developmental events.

18. A computer-implemented method of processing a time series of images of an embryo to determine estimated timings for a plurality of developmental events for the embryo, wherein the method comprises:
  determining feature information for each of the images, the feature information for each image representing the content of the image;
  establishing machine learned classifiers for associating each of the images with a respective likelihood of the image being associated with one or more of the plurality of developmental events based on the feature information for the image;
  applying the machine learned classifiers to the feature information for each of the images to determine a respective likelihood of the image being associated with one or more of the plurality of developmental events; and
  determining estimated timings for the plurality of developmental events for the embryo from the respective likelihoods of the respective images being associated with respective ones of the plurality of developmental events,
  wherein each image of the embryo comprises a plurality of frames representing the embryo at substantially the same stage of its development and the plurality of frames correspond to representations of the embryo in different focal planes and/or different colors.

19. A computer apparatus for processing a time series of images of an embryo to determine estimated timings for a plurality of developmental events for the embryo, wherein the computer apparatus comprises a processor element configured to:
  determine feature information for each of the images, the feature information for each image representing the content of the image;

establish machine learned classifiers for associating each of the images with a respective likelihood of the image being associated with one or more of the plurality of developmental events based on the feature information for the image;
apply the machine learned classifiers to the feature information for each of the images to determine a respective likelihood of the image being associated with one or more of the plurality of developmental events; and
determine estimated timings for the plurality of developmental events for the embryo from the respective likelihoods of the respective images being associated with respective ones of the plurality of developmental events,
wherein the plurality of developmental events for the embryo comprise one or more developmental events selected from the group comprising:
(i) any cleavage event
(ii) cleavage to a 2-blastomere embryo;
(iii) cleavage to a 3-blastomere embryo;
(iv) cleavage to a 4-blastomere embryo;
(v) cleavage to a 5-blastomere embryo;
(vi) cleavage to a 6-blastomere embryo;
(vii) cleavage to a 7-blastomere embryo;
(viii) cleavage to an 8-blastomere embryo;
(ix) cleavage to an 9 or more blastomere embryo;
(x) fading of pronuclei;
(xi) start of compaction;
(xii) formation of morula;
(xiii) initial differentiation of trophectoderm;
(xiv) start of blastulation;
(xv) formation of a blastocyst;
(xvi) initial differentiation of inner cell mass;
(xvii) onset of expansion of a blastocyst;
(xviii) hatching of a blastocyst;
(xix) appearance of first polar body;
(xx) appearance of second polar body;
(xxi) appearance of first pronuclei;
(xxii) appearance of second pronuclei;
(xxiii) time of pronuclei alignment;
(xiv) start of blastocyst collapse; and
(xv) start of blastocyst re-expansion.

20. A computer apparatus for processing a time series of images of an embryo to determine estimated timings for a plurality of developmental events for the embryo, wherein the computer apparatus comprises a processor element configured to:
determine feature information for each of the images, the feature information for each image representing the content of the image;
establish machine learned classifiers for associating each of the images with a respective likelihood of the image being associated with one or more of the plurality of developmental events based on the feature information for the image;
apply the machine learned classifiers to the feature information for each of the images to determine a respective likelihood of the image being associated with one or more of the plurality of developmental events; and
determine estimated timings for the plurality of developmental events for the embryo from the respective likelihoods of the respective images being associated with respective ones of the plurality of developmental events and determining a confidence estimate for respective ones of the estimated timings.

21. A computer apparatus for processing a time series of images of an embryo to determine estimated timings for a plurality of developmental events for the embryo, wherein the computer apparatus comprises a processor element configured to:
determine feature information for each of the images, the feature information for each image representing the content of the image;
establish machine learned classifiers for associating each of the images with a respective likelihood of the image being associated with one or more of the plurality of developmental events based on the feature information for the image;
apply the machine learned classifiers to the feature information for each of the images to determine a respective likelihood of the image being associated with one or more of the plurality of developmental events; and
determine estimated timings for the plurality of developmental events for the embryo from the respective likelihoods of the respective images being associated with respective ones of the plurality of developmental events,
wherein each image of the embryo comprises a plurality of frames representing the embryo at substantially the same stage of its development and the plurality of frames correspond to representations of the embryo in different focal planes and/or different colors.

* * * * *